United States Patent
Carl et al.

(10) Patent No.: US 7,611,526 B2
(45) Date of Patent: Nov. 3, 2009

(54) SPINOUS PROCESS REINFORCEMENT DEVICE AND METHOD

(75) Inventors: Allen L. Carl, Slingerlands, NY (US); Dan Sachs, Minneapolis, MN (US)

(73) Assignees: K Spine, Inc., Minnetonka, MN (US); Albany Medical College, Albany, NY (US)

( * ) Notice: Subject to any disclaimer, the term of this patent is extended or adjusted under 35 U.S.C. 154(b) by 620 days.

(21) Appl. No.: 11/197,573

(22) Filed: Aug. 3, 2005

(65) Prior Publication Data
US 2006/0058790 A1 Mar. 16, 2006

Related U.S. Application Data

(60) Provisional application No. 60/598,882, filed on Aug. 3, 2004.

(51) Int. Cl.
*A61B 17/70* (2006.01)
(52) U.S. Cl. .................. 606/248; 606/257; 606/284
(58) Field of Classification Search ............. 606/248, 606/249, 257, 284; 623/17.11–17.16
See application file for complete search history.

(56) References Cited

U.S. PATENT DOCUMENTS

| | | | |
|---|---|---|---|
| 2,774,350 A * | 12/1956 | Cleveland, Jr. ............... 606/54 |
| 3,242,922 A | 3/1966 | Thomas | |
| 3,648,691 A | 3/1972 | Lumb et al. | |
| 4,024,588 A | 5/1977 | Janssen et al. | |
| 4,078,559 A | 3/1978 | Nissinen | |
| 4,369,769 A | 1/1983 | Edwards | |
| 4,805,602 A | 2/1989 | Puno et al. | |
| 5,011,484 A | 4/1991 | Breard | |
| 5,030,220 A | 7/1991 | Howland | |
| 5,092,866 A | 3/1992 | Breard et al. | |
| 5,092,867 A | 3/1992 | Harms et al. | |
| 5,127,912 A * | 7/1992 | Ray et al. ................... 606/250 |
| 5,133,716 A | 7/1992 | Plaza | |
| 5,242,443 A | 9/1993 | Kambin | |
| 5,306,275 A | 4/1994 | Bryan | |
| 5,366,455 A | 11/1994 | Dove et al. | |
| 5,397,363 A | 3/1995 | Gelbard | |
| 5,413,576 A | 5/1995 | Rivard | |
| 5,437,669 A | 8/1995 | Yuan et al. | |
| 5,437,671 A | 8/1995 | Lozier et al. | |
| 5,456,722 A | 10/1995 | McLeod et al. | |
| 5,470,333 A | 11/1995 | Ray | |
| 5,480,440 A | 1/1996 | Kambin | |
| 5,490,851 A | 2/1996 | Nenov et al. | |

(Continued)

FOREIGN PATENT DOCUMENTS

EP 0260044 3/1988

(Continued)

OTHER PUBLICATIONS

International Search Report dated Oct. 2, 2008 for PCT/US 08/65979.

*Primary Examiner*—Pedro Philogene
(74) *Attorney, Agent, or Firm*—Knobbe Martens Olson & Bear LLP

(57) ABSTRACT

A method and device for reinforcing a spinous process is provided. Also provided are devices and method for attaching devices thereto.

29 Claims, 45 Drawing Sheets

U.S. PATENT DOCUMENTS

| | | | |
|---|---|---|---|
| 5,496,318 A | 3/1996 | Howland et al. | |
| 5,498,262 A | 3/1996 | Bryan | |
| 5,549,679 A | 8/1996 | Kuslich | |
| 5,562,660 A | 10/1996 | Grob | |
| 5,562,662 A | 10/1996 | Brumfield et al. | |
| 5,569,246 A | 10/1996 | Ojima et al. | |
| 5,591,165 A | 1/1997 | Jackson | |
| 5,645,599 A * | 7/1997 | Samani | 623/17.16 |
| 5,702,395 A | 12/1997 | Hopf | |
| 5,725,582 A | 3/1998 | Bevan et al. | |
| 5,728,097 A | 3/1998 | Mathews | |
| 5,733,284 A * | 3/1998 | Martin | 606/248 |
| 5,814,046 A | 9/1998 | Hopf | |
| 5,928,232 A | 7/1999 | Howland et al. | |
| 5,989,256 A | 11/1999 | Kuslich et al. | |
| 6,015,409 A | 1/2000 | Jackson | |
| 6,136,000 A | 10/2000 | Louis et al. | |
| 6,358,254 B1 | 3/2002 | Anderson | |
| 6,364,883 B1 | 4/2002 | Santilli | |
| 6,451,019 B1 | 9/2002 | Zucherman et al. | |
| 6,551,320 B2 | 4/2003 | Lieberman | |
| 6,565,605 B2 | 5/2003 | Goble et al. | |
| 6,579,319 B2 | 6/2003 | Goble et al. | |
| 6,582,433 B2 | 6/2003 | Yun | |
| 6,589,243 B1 | 7/2003 | Viart et al. | |
| 6,610,091 B1 * | 8/2003 | Reiley | 623/17.11 |
| 6,616,669 B2 | 9/2003 | Ogilvie et al. | |
| 6,626,909 B2 | 9/2003 | Chin | |
| 6,641,585 B2 | 11/2003 | Sato et al. | |
| 6,645,207 B2 | 11/2003 | Dixon et al. | |
| 6,669,729 B2 * | 12/2003 | Chin | 623/17.11 |
| 6,709,435 B2 * | 3/2004 | Lin | 606/250 |
| 6,802,844 B2 | 10/2004 | Ferree | |
| 6,811,567 B2 * | 11/2004 | Reiley | 623/17.11 |
| 6,946,000 B2 | 9/2005 | Senegas et al. | |
| 6,966,930 B2 | 11/2005 | Arnin et al. | |
| 6,986,771 B2 | 1/2006 | Paul et al. | |
| 7,048,736 B2 | 5/2006 | Robinson et al. | |
| 7,074,237 B2 | 7/2006 | Goble et al. | |
| 7,087,056 B2 | 8/2006 | Vaughan | |
| RE39,325 E | 10/2006 | Bryan | |
| 7,220,262 B1 | 5/2007 | Hynes | |
| 7,335,203 B2 | 2/2008 | Winslow et al. | |
| 2002/0151978 A1 | 10/2002 | Zacouto et al. | |
| 2003/0040746 A1 | 2/2003 | Mitchell et al. | |
| 2003/0093117 A1 | 5/2003 | Saadat | |
| 2003/0109881 A1 * | 6/2003 | Shirado et al. | 606/61 |
| 2003/0153915 A1 | 8/2003 | Nekozuka et al. | |
| 2003/0220643 A1 | 11/2003 | Ferree | |
| 2004/0006391 A1 * | 1/2004 | Reiley | 623/17.11 |
| 2004/0097931 A1 | 5/2004 | Mitchell | |
| 2004/0106921 A1 | 6/2004 | Cheung et al. | |
| 2004/0149065 A1 | 8/2004 | Moran | |
| 2004/0167520 A1 | 8/2004 | Zuckerman et al. | |
| 2005/0043797 A1 | 2/2005 | Lee | |
| 2005/0049705 A1 | 3/2005 | Hale et al. | |
| 2005/0055096 A1 * | 3/2005 | Serhan et al. | 623/17.11 |
| 2005/0080420 A1 | 4/2005 | Farris et al. | |
| 2005/0149030 A1 | 7/2005 | Serhan et al. | |
| 2005/0203509 A1 | 9/2005 | Chinnaian et al. | |
| 2005/0203511 A1 | 9/2005 | Wilson-MacDonald et al. | |
| 2005/0209603 A1 | 9/2005 | Zucherman et al. | |
| 2005/0216004 A1 | 9/2005 | Schwab | |
| 2005/0245929 A1 | 11/2005 | Winslow et al. | |
| 2005/0261770 A1 | 11/2005 | Kuiper et al. | |
| 2005/0267470 A1 | 12/2005 | McBride | |
| 2006/0047282 A1 | 3/2006 | Gordon | |
| 2006/0271050 A1 | 11/2006 | Piza Vallespir | |
| 2007/0073293 A1 | 3/2007 | Martz et al. | |
| 2007/0233093 A1 | 10/2007 | Falahee | |

FOREIGN PATENT DOCUMENTS

| | | |
|---|---|---|
| EP | 0322334 | 6/1989 |
| EP | 0418387 | 3/1991 |
| EP | 1281361 | 2/2003 |
| FR | 2736535 | 1/1997 |
| FR | 2781359 | 1/2000 |
| FR | 2801492 | 6/2001 |
| GB | 780652 | 7/1955 |
| WO | WO 92/13496 | 8/1992 |

* cited by examiner

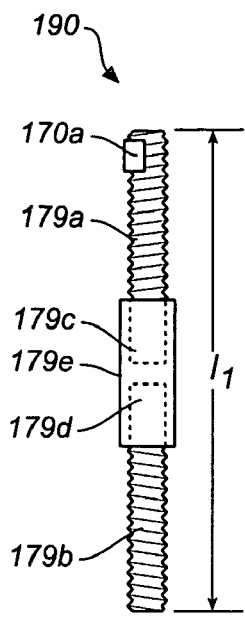 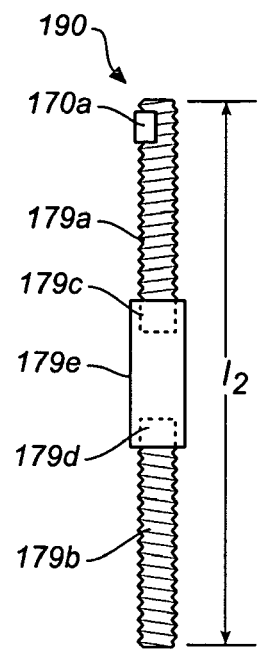 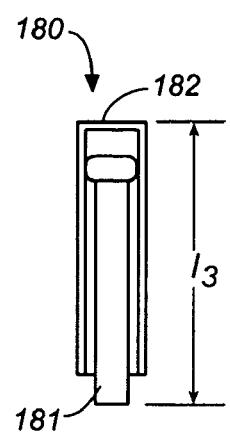 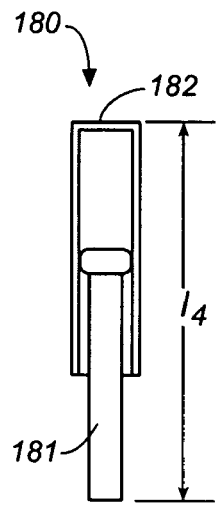
FIG. 16A    FIG. 16B    FIG. 16C    FIG. 16D
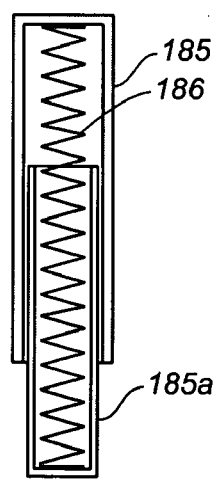 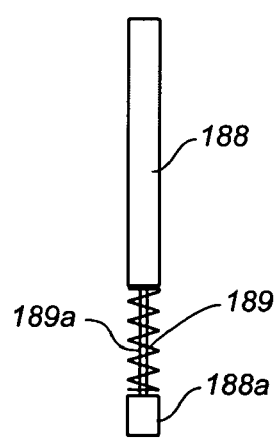
FIG. 16E    FIG. 16F

SPINOUS PROCESS REINFORCEMENT DEVICE AND METHOD

RELATED APPLICATION DATA

The present application claims the priority of Provisional Application No. 60/598,882, filed Aug. 3, 2004 and entitled: Spine Treatment Devices and Methods.

FIELD OF THE INVENTION

The invention relates to devices to treat the spine, including but not limited to spinal stabilization devices, dynamic stabilizers, spinal deformity correction devices, spinal distraction devices, facet implants and devices to treat pain associated with the spine, and other spinal treatment devices.

BACKGROUND

Certain spine conditions, defects, deformities (e.g., scoliosis) as well as injuries may lead to structural instabilities, nerve or spinal cord damage, pain or other manifestations. Back pain (e.g., pain associated with the spinal column or mechanical back pain) may be caused by structural defects, by injuries or over the course of time from the aging process. For example, back pain is frequently caused by repetitive and/or high stress loads on or increased motion around certain boney or soft tissue structures. The natural course of aging leads to degeneration of the disc, loss of disc height, and instability of the spine among other structural manifestations at or around the spine. With disc degeneration, the posterior elements of the spine bear increased loads with disc height loss, and subsequently attempt to compensate with the formation of osteophytes and thickening of various stabilizing spinal ligaments. The facet joints may develop pain due to arthritic changes caused by increased loads. Furthermore, osteophytes in the neural foramina and thickening of spinal ligaments can lead to spinal stenosis, or impingement of nerve roots in the spinal canal or neural foramina. Scoliosis may also create disproportionate loading on various elements of the spine and may require correction, stabilization or fusion.

Pain caused by abnormal motion of the spine has long been treated by fixation of the motion segment. Spinal fusion is one way of stabilizing the spine to reduce pain. In general, it is believed that anterior interbody or posterior fusion prevents movement between one or more joints where pain is occurring from irritating motion. Fusion typically involves removal of the native disc, packing bone graft material into the resulting intervertebral space, and anterior stabilization, e.g., with intervertebral fusion cages or posterior stabilization, e.g., supporting the spinal column with internal fixation devices such as rods and screws. Internal fixation is typically an adjunct to attain intervertebral fusion. Many types of spine implants are available for performing spinal fixation, including the Harrington hook and rod, pedicle screws and rods, interbody fusion cages, and sublaminar wires.

Alternatives have been proposed and tested to replace the need for spinal fusion to treat patients with back pain. These implants include artificial discs and artificial nucleus technologies that preserve motion. However, these implants do not directly address the forces borne by the facet joints.

The facet joints provide a means for load transmission, support and motion of the posterior spinal column. Disc height loss from degenerative disc disease and aging leads to increased load on the facet joints, which can lead to arthritic, painful, degenerative changes.

Often over the course of degenerative disc disease there is a narrowing of the neural foramen through which the nerves exit the spine. In addition to the degeneration of discs causing the narrowing of the foramen, there is also calcification around the foramen causing further narrowing or stenosis resulting in pain to the patient. Currently, these conditions may be treated by removing some or all of the lamina (laminectomy) or posterior bone adjacent or around the stenotic neural foramen Given that the facet joint and its environs is a source of pain for some patients, some procedures have been developed or proposed to relieve pain associated with the facet joint. Partial or complete removal of the pathological facets, and replacement with a mechanical joint that preserves motion similar to a facet has been proposed. Additionally, individual degenerative facet articulations have been replaced with caps.

It would be desirable to provide improved devices and methods for relieving pain associated with the facet joints.

Spinal stenosis pain or from impingement of nerve roots in the neural foramina has been treated by laminectomy and foraminotomy, and sometimes reinforced with rod and screw fixation of the posterior spine.

Such procedures involve removing remove bone, calcifications or other growth that closes around or impinges on spinal nerves, sac centrally, and nerve roots. Sometimes these procedures include reinforcement of the posterior spine with rod and screw fixation.

Pain due to instability of the spine has also been treated with dynamic stabilization of the posterior spine, using elastic bands that connect pedicles of adjacent vertebrae.

More recently, as an alternative to laminectomies and related procedures, implants have been proposed that distract the spine from a posterior approach. In particular, a wedge-like implant inserted between two adjacent spinous processes has been proposed to relieve pressure on spinal nerves and nerve roots. A kyphosis is induced, which opens the space of the spinal canal and neural foramen, thereby reducing the effect of spinal stenosis. However, this type of distraction of adjacent spinous processes is suboptimal for several reasons: The resulting kyphosis is non-physiologic, leading to increased load on the anterior portion of the disc and the vertebral bodies. This can increase the risk of disc degeneration and vertebral compression fracture. The implant tends to bend the spine forward. Bone may collapse around the spinous process. The implant may weaken, tear, or stretch stabilizing ligaments of the spine, such as the supraspinous ligament, interspinous ligament, ligamentum flavum, posterior longitudinal ligament, or capsule of the zygapophyseal joint. The amount of distraction is not adjustable to the specific amount of stenosis, and cannot be easily readjusted months to years after the device has been implanted.

It would accordingly be desirable to provide a distraction device that reduces or avoids some or all of these issues.

The typical techniques for fusion, distraction, decompression, and dynamic stabilization require open surgical procedures with removal of stabilizing muscles from the spinal column, leading to pain, blood loss, and prolonged recovery periods after surgery due in part to the disruption of associated body structures or tissue during the procedures. Accordingly, it would be desirable to provide less invasive devices and methods for treating pain or discomfort associated with the spinal column. It would also be desirable to provide such devices and methods that are less damaging to associated tissue.

To reduce the invasiveness of fusion procedures, some methods of fusion have been proposed that do not require the extensive stripping of muscles away from the spinal column of earlier approaches. These involve posteriorly or laterally accessing the spine and creating spaces adjacent the spine for posterior stabilization. Some of these procedures include fusion via small working channels, created with dilator type devices or an external guide to create a trajectory channel between two ipsilateral neighboring pedicle screws. Also, placing support structures between adjacent pedicle screws and across a joint requires accessing and working in an area from a difficult angle (the support structure is typically oriented somewhat perpendicular to an angle of access and through muscle and connective tissue). Furthermore, these stabilization devices typically involve the use of 4 pedicle screws (each having a risk associated with it when placed in the spine), two on each side of a motion segment, and are not ideally suited for percutaneous stabilization required across more than one or two segments. Accordingly, it would be desirable to provide a less invasive or less disruptive segmental spine stabilization procedure and implant that has a reduced risk of damage or injury to associated tissue. It would also be desirable to provide an implanted posterior spine system that may be used to stabilize more than two motion segments in a less disruptive or less invasive manner.

One method of fusing a vertebra has been proposed using bilateral screws through the lamina using a posterior approach. However, geometric placement of the device is difficult and the procedure is considered dangerous because the laminar screws could enter through anteriorly into the spinal canal and cause nerve damage.

Accordingly, it would be desirable to provide a device that reduces the difficulties risks of the current procedures. It would also be desirable to provide a device that can be placed in a less disruptive or less invasive manner than commonly used procedures.

Unintended consequences of fixation include stress shielding of bone, as well as transfer of load to adjacent, still dynamic motion segments, and eventual degeneration of adjacent motion segments. Flexible stabilization of motion segments with plastic, rubber, super-elastic metals, fabric, and other elastic materials has been proposed to provide a degree of dynamic stabilization of some joints. Many of these constructs are not load bearing. Dynamic stabilization from pedicle screw to pedicle screw along the length of the spine has been proposed. However, this device has the disadvantage of requiring placement of 4 pedicle screws and associated tissue disruption.

Due to the risks, inconvenience, and recovery time required for surgical implantation of spinal devices, some patients may continue to prefer rigid fixation of a painful or degenerative motion segment over dynamic stabilization of the joint. In addition, doctors may be reluctant to recommend dynamic stabilization for patients with back pain, because it may not alleviate pain to a patient's satisfaction.

Furthermore, even in patients who experience good relief of pain with dynamic stabilizers, it is anticipated that while the onset of arthritic changes may be deferred, many patients will still eventually proceed to develop degeneration, and require fixation of the motion segment to obtain pain relief. Repeat spine procedures to remove one implant and replace it with another are associated with complications related to bleeding, surgical adhesions, destruction of bone, and other generic risks associated with surgical procedures. Accordingly, improved devices that address these issues would be desirable.

A number of spinal deformities exist where the spine is abnormally twisted and or curved. Scoliosis is typically considered an abnormal lateral curvature of the vertebral column.

Correction of scoliosis has been attempted a number of ways. Typically correction is followed by fusion. A Harrington rod has been used where a compressing or distracting rod is attached above and below a curved arch of the deformity. The spine is stretched longitudinally to straighten the spine as the rod is lengthened. The spine is then fused. The correction force in this device and in similar devices is a distraction force that may have several drawbacks including possible spinal cord damage, as well as the high loading on the upper and lower attachment sites. Nowadays, segmental hook and screw fixation exists for distraction and derotation corrective forces.

A Luque device has been used where the spine is wired to a rod at multiple fixation points along the rod and pulls the spine to the rod. The spine is pulled to the rod with a wire and the spine is then fused. This does not provide significant adjustment over time and requires fusion. Once completed this does not provide an opportunity for delayed adjustment over time. Anterior procedures also exist in the form of fusion and newer technology involving staples across the disc space that obviate the need for fusion but still correct the deformity. The corrective force is derotation with or without compression.

Accordingly it would be desirable to provide an improved corrective device for treating scoliosis or other deformities. It would also be desirable to provide a device that may be used without fusion.

Spine surgeons commonly use metallic or polymeric implants to effect or augment the biomechanics of the spine. The implants frequently are attached or anchored to bone of the spine. Sites typically considered appropriate for boney attachment have high density or surface area, such as, for example, the pedicle bone, the vertebral body or the cortical bone of the lamina. The spinous process contains thin walls of cortical bone, and thus, has been considered as not ideal for anchoring spinal implants as they may not support the implants under physiologic loads, or the intermittent high loads seen in traumatic situations. Fixation has been attempted from spinous process to spinous process with poor results.

A translaminar facet screw as used by some surgeons goes through the base of spinous process to access the cancellous bone of the lamina. A disadvantage of this device is that it is not suitable for attaching to a pedicle screw and the depth and angle during deployment can be very difficult to track or visualize, thus increasing the possibility that the screw would extend into the spinal canal. A facet screw is screwed between opposing facets of a zygapophyseal joint.

SUMMARY

One aspect of the present invention is directed to providing a device and method for alleviating discomfort and or deformity associated with the spinal column. Another aspect of the present invention is directed to providing a minimally invasive implant and method for alleviating discomfort associated with the spinal column. Another aspect of the present invention provides an anchoring device and method that requires less surrounding tissue damage or disruption. Another aspect of the present invention provides reinforcement of the spinous process for use in various spinal systems. Another aspect of the invention provides a minimally invasive, non-invasive, or remote adjustment or lengthening of an orthopedic device. Another aspect of the invention provides a minimally invasive, non-invasive, or remote adjustment, lengthening or shortening of a stabilization device. Another aspect of the present invention also provides an implant system and device suitable for minimally invasive, minimally disruptive and/or percutaneous posterior deployment across a plurality of motion segments and more than two motion segments. Different aspects of the invention may provide distraction forces to relieve pressure on certain structures, compression forces to fix or stabilize motion across structures, shock absorbing qualities to help relieve load from certain structures, and therapeutic activity to reduce inflammation and pain. Other aspects of the invention may supplement or bear load for degenerated, painful, or surgically removed joints, e.g., the facet joint. Another aspect of the invention may provide a method and system for treating deformities such as scoliosis. Other aspects of the invention may include sensors associated with implants or implanted at or near the bones, soft tissue, or joints of the spine and may provide feedback regarding the joint on an ongoing basis. The sensors may also be part of a feedback system that alters a property of an implant in response to sensing information. Another aspect of the invention may provide a device or method for delivering therapeutic substances at or near the spine.

One aspect of the invention provides for repair or reconstruction of a dysfunctional facet joint. For example, by entering the capsule of the facet joint, creating a space between articulating facets by removing synovium, cartilage, and some bone from within the zygapophysial joint, and, then, inserting a motion preserving prosthesis. Motion preserving prostheses may include a smooth and/or curved surface, a sphere, an egg shaped/oval implant, or a self contained "ball and socket" joint. Magnetic plates with like poles facing each other may be attached to interfacing articulating portions of the facets. Attachment of the motion preserving prosthesis may involve extensions from the prosthesis that partially or completely penetrate each of the facets.

Another aspect of the invention provides for repairing the encapsulating ligaments with suture, adhesive, a patch, or other materials after a capsule of the zygapophysial joint has been invaded for tissue removal and insertion of a prosthesis. One aspect of the invention includes an elastic encapsulating wrap used to stabilize the facet joints. Another aspect of the invention provides a stabilizing or distraction rod used to keep each facet in apposition, thereby keeping the prosthesis in place. In accordance with an aspect of the invention, the stabilizing or distraction rod may be placed between ipsilateral pedicles of each articulating segment, between contralateral pedicles, between the spinous process and pedicle, or between the lamina and pedicle.

According to an embodiment of the invention, a facet distraction implant is provided for maintaining a space that is formed between the facet articulations of adjacent vertebrae when the joints are distracted. The facets may be distracted using a known distraction method or technique and an implant may be placed between the facets. A securing device according to the invention may be positioned to anchor each of the facet articulations of a facet joint to each other in distraction to maintain the opening of the corresponding neural foramen. The prosthesis may include a distraction element that exerts a distracting force on the joint.

According to another aspect of the invention, a facet joint replacement or augmentation may comprise a stabilizing prosthesis placed through a spinous process of a first vertebra associated with the facet joint to be replaced, across or adjacent the location of the removed or partially removed facet and anchored in a bony portion of an adjacent second vertebra associated with the facet joint to be replaced, i.e. pedicle, transverse process, lamina or other bony portion. The stabilizing prosthesis may include a dynamic portion that permits some movement of the stabilizing device. The stabilizing device may also be bilateral.

According to another embodiment, the facet replacement stabilizing device may be anchored to contralateral pedicles of adjacent vertebrae. The stabilizing device may also be bilateral.

According to another aspect of the invention a facet joint replacement or augmentation may comprise a distracting prosthesis placed through a spinous process of a first vertebra associated with the facet joint to be replaced or across or adjacent the location of the removed or partially removed facet and anchored in a bony portion of an adjacent second vertebra associated with the facet joint to be replaced. The distracting prosthesis may include a dynamic portion that permits some movement of the stabilizing device. The distracting device may be bilateral.

In another embodiment, a distracting device may be anchored to contralateral pedicles of adjacent vertebrae. The distracting device may also be bilateral.

In accordance with one aspect of the invention, a reinforcement structure is provided for supporting the spinous process and if desired, in addition, the lamina of a spine, e.g. for securing portions devices to the spine. The invention further provides a method and system for forming or implanting such structure in the spinous process or a region of cancellous bone in the lamina of a spine. The reinforcement system may include one or more systems of reinforcement and may be used before, during and/or after a spinal device (e.g. a stabilization, distraction or prosthetic device, etc.) is coupled to the spinous process.

Various aspects of the invention are set forth in the description and/or claims herein.

BRIEF DESCRIPTION OF THE DRAWINGS

FIG. 16A is a side schematic view of a distraction element in a first position in accordance with the invention.

FIG. 16B is a side schematic view of the distraction element of FIG. 16A in a second position in accordance with the invention.

FIG. 16C is a side schematic view of a distraction element in a first position in accordance with the invention.

FIG. 16D is a side schematic view of the distraction element of FIG. 16C in a second position in accordance with the invention.

FIG. 16E is a side schematic view of a distraction element in accordance with the invention.

FIG. 16F is a side schematic view of a distraction element in accordance with the invention.

DETAILED DESCRIPTION

Figure 1A:
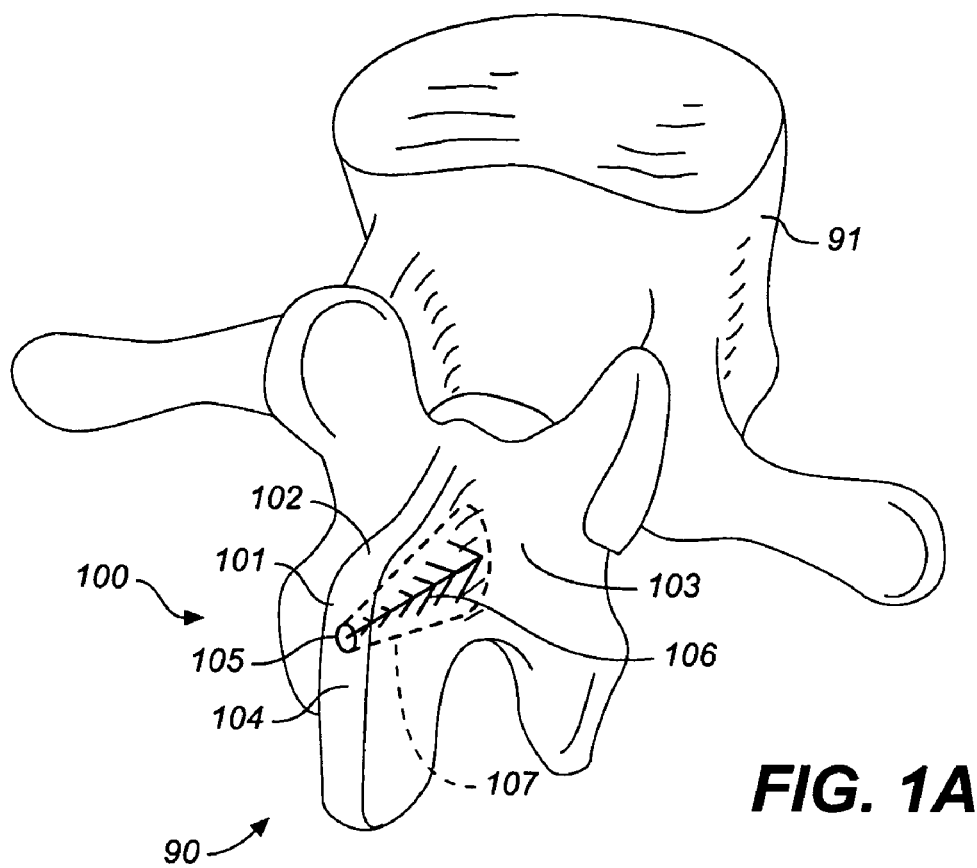
FIG. 1A is a lateral posterior view of a vertebra with a reinforcement structure in accordance with the invention.
Figure 1B:
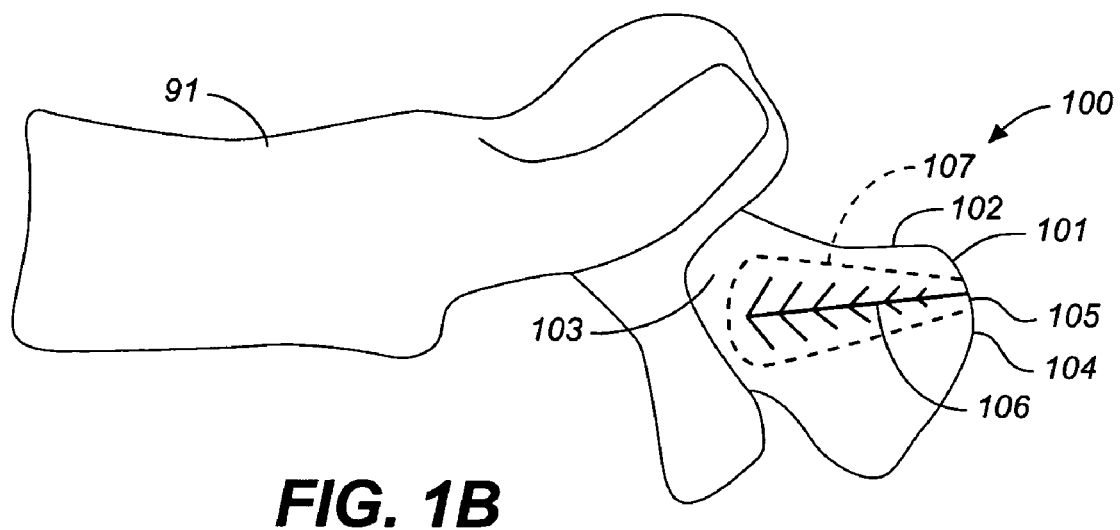
FIG. 1B is a side view of the vertebra and reinforcement structure of FIG. 1A.

FIGS. 1A and 1B illustrate a reinforced posterior arch 100 of a first vertebra 91 of a spine 90, including a spinous process 101 and lamina 103. The first vertebra 100 of the spine 90 as illustrated includes a first spinous process 101 with a superior portion 102 having a posterior ridge 104 into which a hole 105 is drilled. The hole 105 may be drilled with a drill, a trocar, a large bore IV needle or similar sharp object through the external and relatively hard cortical bone, to reach the internal cancellous bone within the spinous process 101 and adjacent the lamina 103.

Once the cancellous bone is accessed, optionally, a tool such as a balloon tamp, or other expandable member or small crushing or drilling member is used to create a cavity 107 or cavities within the cancellous bone by compressing, crushing or drilling out the bone material. X-rays may be used to determine how far to drill into the bone. The cavity 107 may be in the spinous process, through to the base of the spinous process, or through the spinous process and into the lamina. In one embodiment the cavity is cone shaped or widens as it moves anteriorly towards the lamina.

A reinforcing material is then delivered into the cancellous bone or cavity 107 of the spinous process 101 and/or within the lamina 103. The material is selected to provide reinforcing properties to the spinous process 101 and/or lamina 103 sufficient to support (whether alone or in combination with other support elements) a spine support structure, a prosthesis, or other device attached to the spinous process and or supported lamina. The material may be a bone cement or polymer with strength and hardness properties selected to provide sufficient reinforcement to the region so that the spinous process may be used at least in part, to support an implant structure for attaching to and manipulating the biomechanics of the spine. Examples include but are not limited to polymers such as acrylic cement developed for use in vertebroplasty procedures. The material may be a flowable polymer material that cures within the cavity. Suitable materials may be readily selected by one of ordinary skill in the art.

Reinforcement structures may be placed within the cavity prior to, during or after injection of flowable material for further strength properties. As illustrated, an additional support structure 106 is provided within the cavity. The support structure 106 may be inserted through a cannula and released to expand as a spring-like or self-expanding member, into the cavity. The support structure 106 provides further support of the spinous process and/or lamina. Alternatively, or additionally, one or more posts or struts may be provided within the cavity or extending out of the spinous process or lamina from the area of cancellous bone, to supplement the support of the spinous process or lamina in combination with the polymer or other curable material. The reinforcement structures may be formed of a number of different materials such as, e.g., a metal or biocompatible polymer. Such reinforcement structures may also be used in other bony areas of the spine including the vertebra, the pedicles, facets, the transverse process, etc.

Figure 2A:
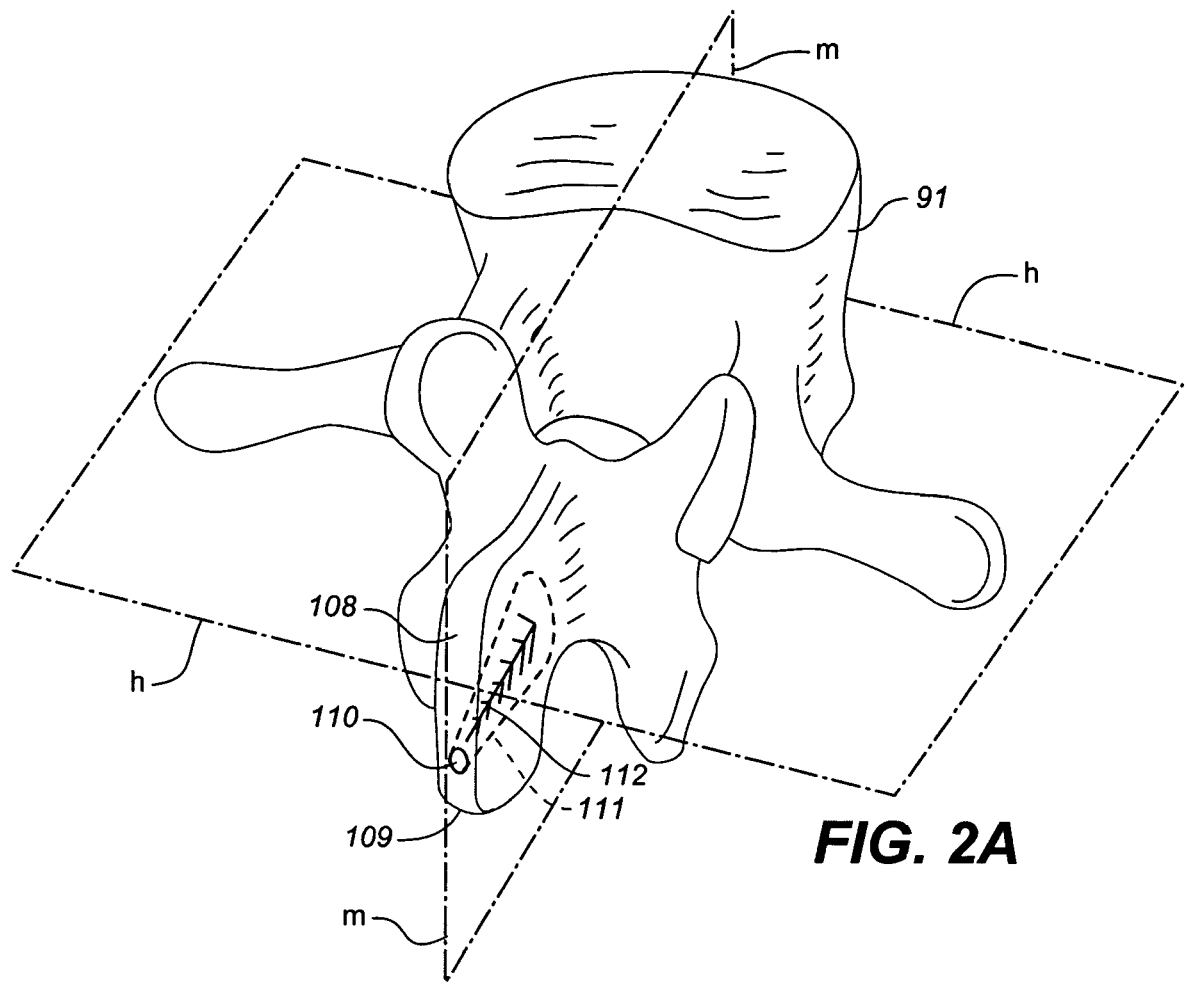
FIG. 2A is a lateral posterior view of a vertebra with a reinforcement structure in accordance with the invention.
Figure 2B:
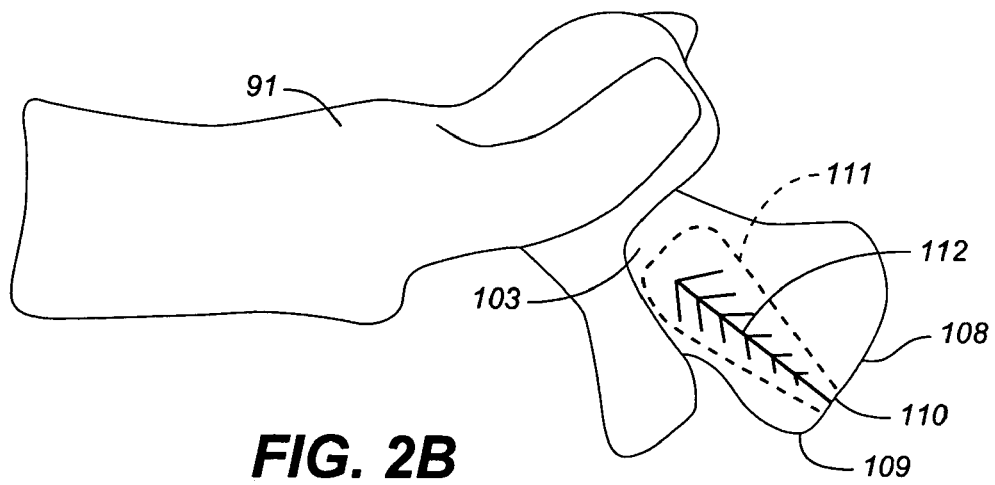
FIG. 2B is a side view of the vertebra and reinforcement structure of FIG. 2A.

As shown in FIGS. 2A and 2B, an inferior portion 109 of a spinous process 108 may also be reinforced. Similarly a hole 110 is drilled in the inferior portion of the spinous process 108 and a cavity 111 is formed. The cavity 111 is similarly filled with a curable polymer and is reinforced by reinforcing elements 112 positioned within the cavity.

The reinforcement structure may be used in a number of applications including increasing the strength of healthy bone to support the load and fixation of orthopedic implants, as well as increasing the strength of bone weakened by osteoporosis, chronic steroid use, avascular necrosis, weakened by injury and cancer involving the bone. According to one aspect, the reinforcement structure comprises a material that provides sufficient strength including but not limited to suitable polymers, e.g. PEAK, titanium, steel and carbon fiber.

The stabilizing and/or distracting devices described herein may be formed of a material that provides sufficient column strength including but not limited to suitable polymers, e.g. PEAK, titanium, steel, and carbon fiber.

Figure 3A:
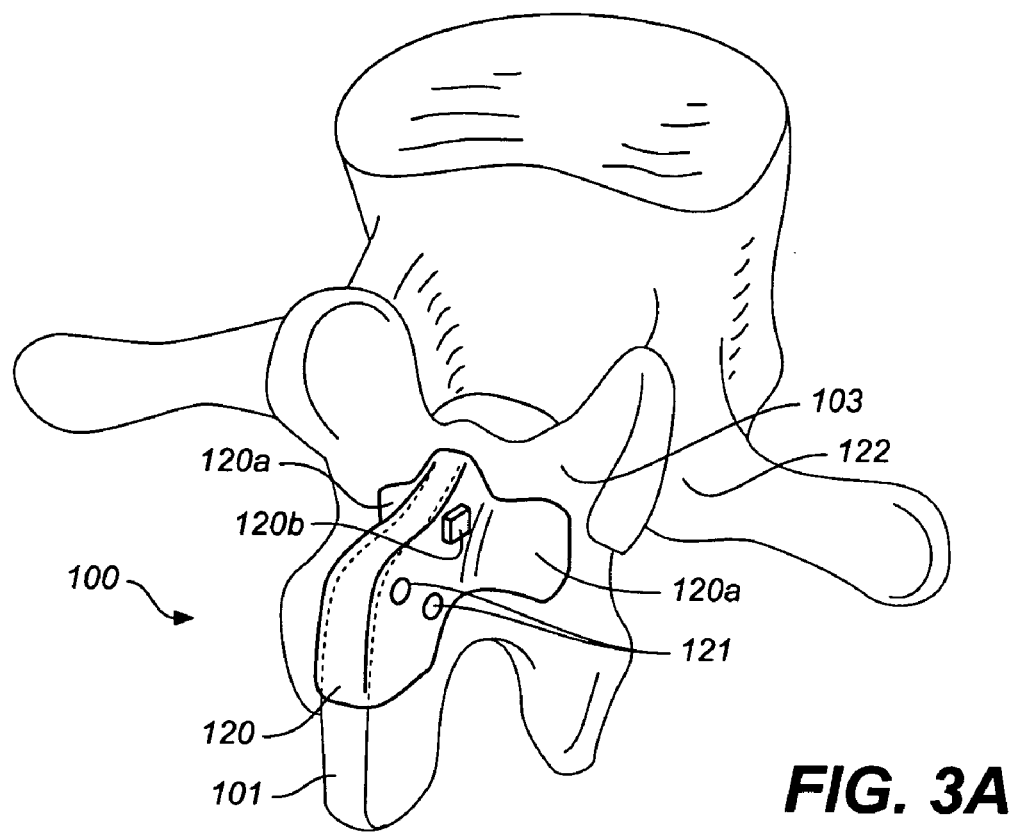
FIG. 3A is a lateral posterior view of a vertebra with a reinforcement structure in accordance with the invention.
Figure 3B:
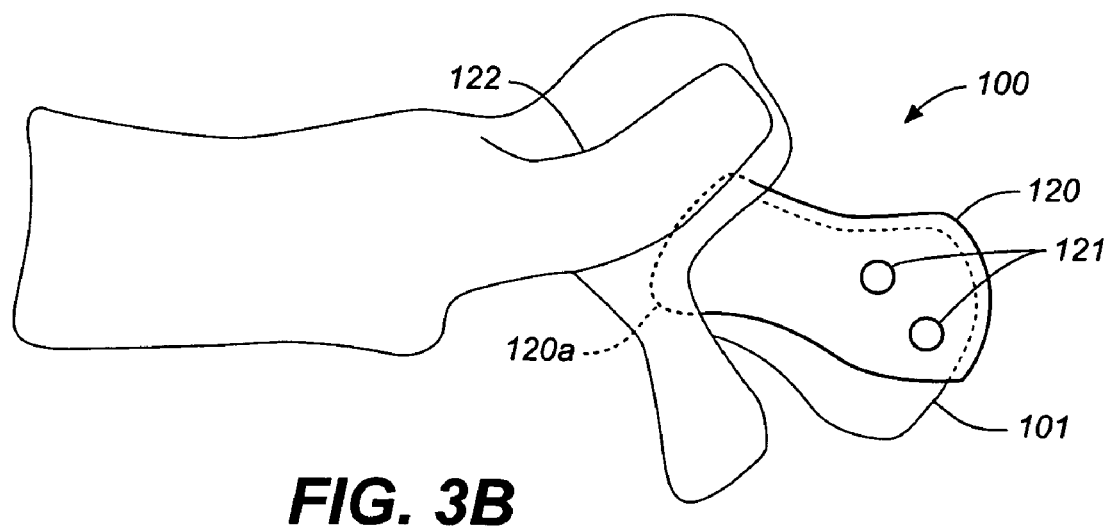
FIG. 3B is a side view of the vertebra and reinforcement structure of FIG. 3A.

Referring to FIGS. 3A and 3B, an alternative support structure 120 is illustrated. The support structure 120 allows the anchoring of implants under physiologic loads on the spinous process 101 while shielding underlying bone from loads that would normally cause the bone to fracture. (The implants may alternatively or in addition be anchored or attached to the lamina 103, e.g., with addition of small screws, barbs or adhesive that engage with the lamina while avoiding injuring the spinal cord surrounded by the lamina.) The support structure 120 comprises a hood like element positioned over the posterior arch 100, i.e., the spinous process 101 and lamina 103 of a spine 90. The support structure 120 may be made of a moldable or malleable material (e.g. putty, formable ceramic, clay-like material, or a moldable polymer or malleable alloy or metal) that cures into or forms a solid, strong structure. Heat, light, catalysts, precursors, or local pressure and force, for example, may be used to make the hood moldable or firm. The support structure of filling material to support the spinous process may be constructed or formed of moldable composites that can cure into hard material such as, e.g., ground glass powder or glass fiber fillers mixed into an acrylic matrix and activated with light or other biophysical modalities. Other cements or other curable materials may be suitable as well. The support structure 120 further comprises openings 121 to guide drill bits and/or for the placement of screws, reinforcement posts, or other instruments or supplemental support structures. The guide may insure accurate positioning of the implant. The support structure 120 may be anchored on the posterior arch by mold bending or forming the structure about the anatomy. The support structure 120 may be anchored into the lamina or spinous process by anchoring elements, such as, e.g., screws or barbs. The support structure 120 may also be anchored via screws or posts. Alternatively, the support structure 120 could be a preformed implant with contours that fit the anatomy of the posterior arch 100 or that are malleable or moldable to the anatomy. Also, the support structure 20 may be anchored into the pedicles 122 with screws, into the underlying bone with barbs, screws, bone anchors, or adhesives, over the edges of structures with hooks, or may be constructed of a plurality of pieces that may be assembled into one piece around the bone. Wings 120a of support structure may be placed over the lamina to spread the force of any device attached to the support structure 120

As illustrated in FIGS. 3A and 3B, a sensor 120*b* is positioned on the support structure 120. The sensor 120*b* may be embedded in the material. The sensor may sense stress on the support structure 120 from implants secured to it, or may sense other information that may be desirable to monitor. The sensor may include a communication element configured to communicate sensed information to an external device, e.g., when interrogated.

Figure 4A:
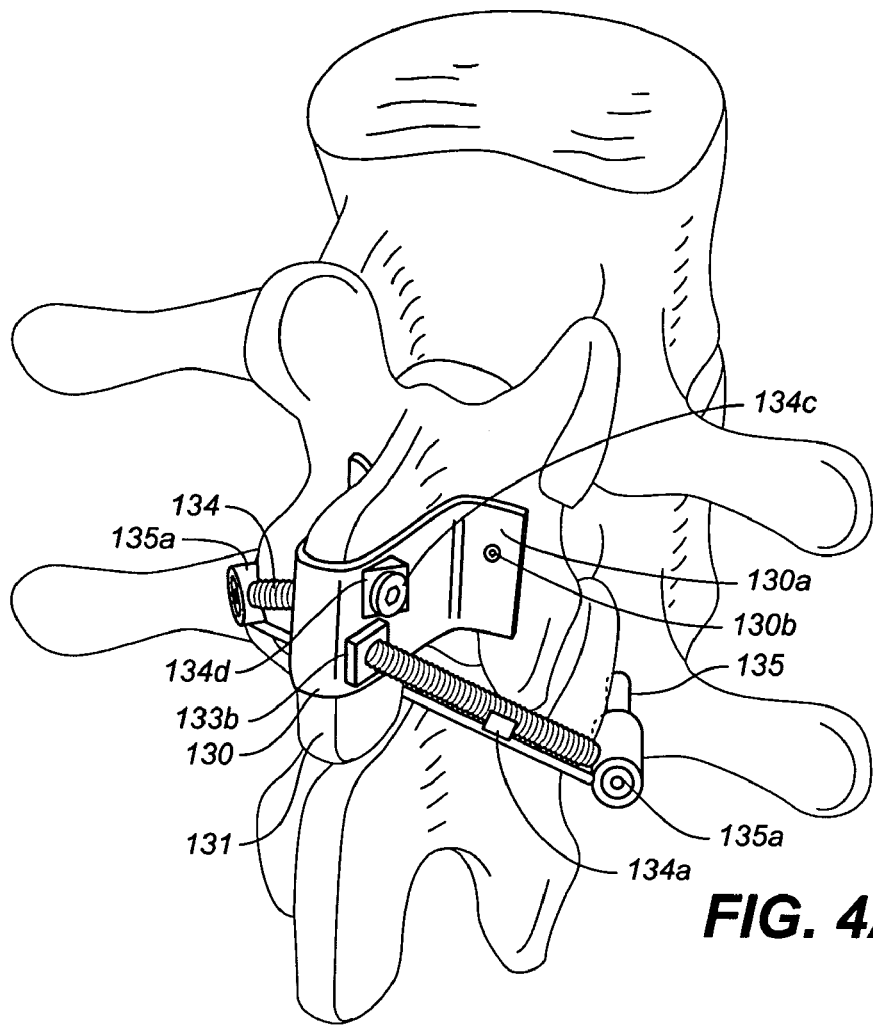
FIG. 4A is a lateral posterior view of vertebrae with a reinforcement structure and implant in accordance with the invention.
Figure 4B:
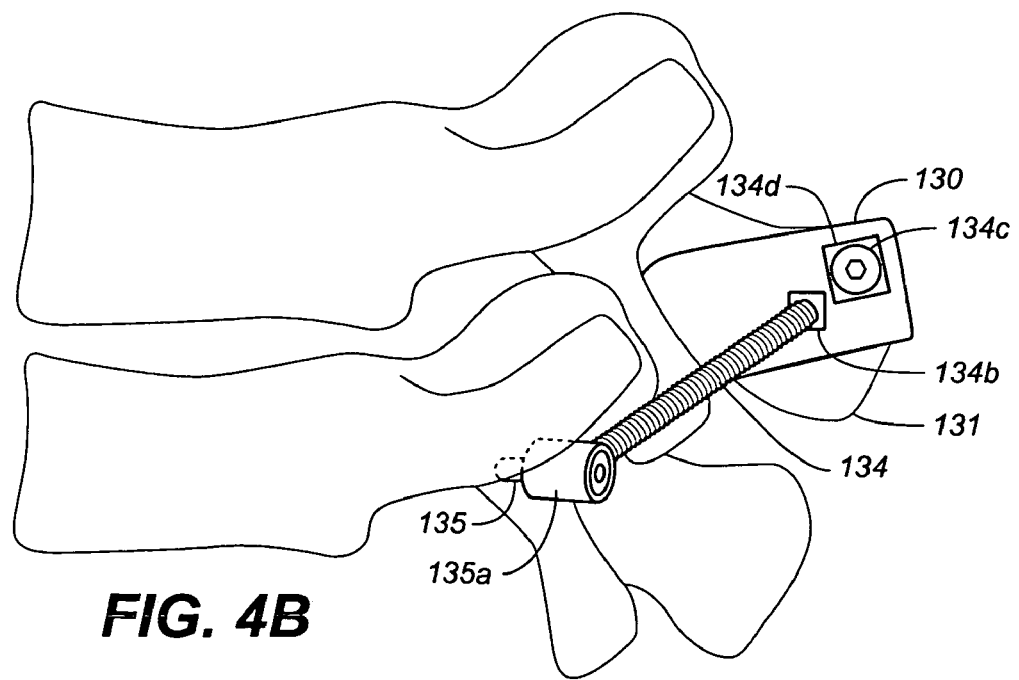
FIG. 4B is a side view of the reinforcement structure and implant of FIG. 4A.
Figure 4C:
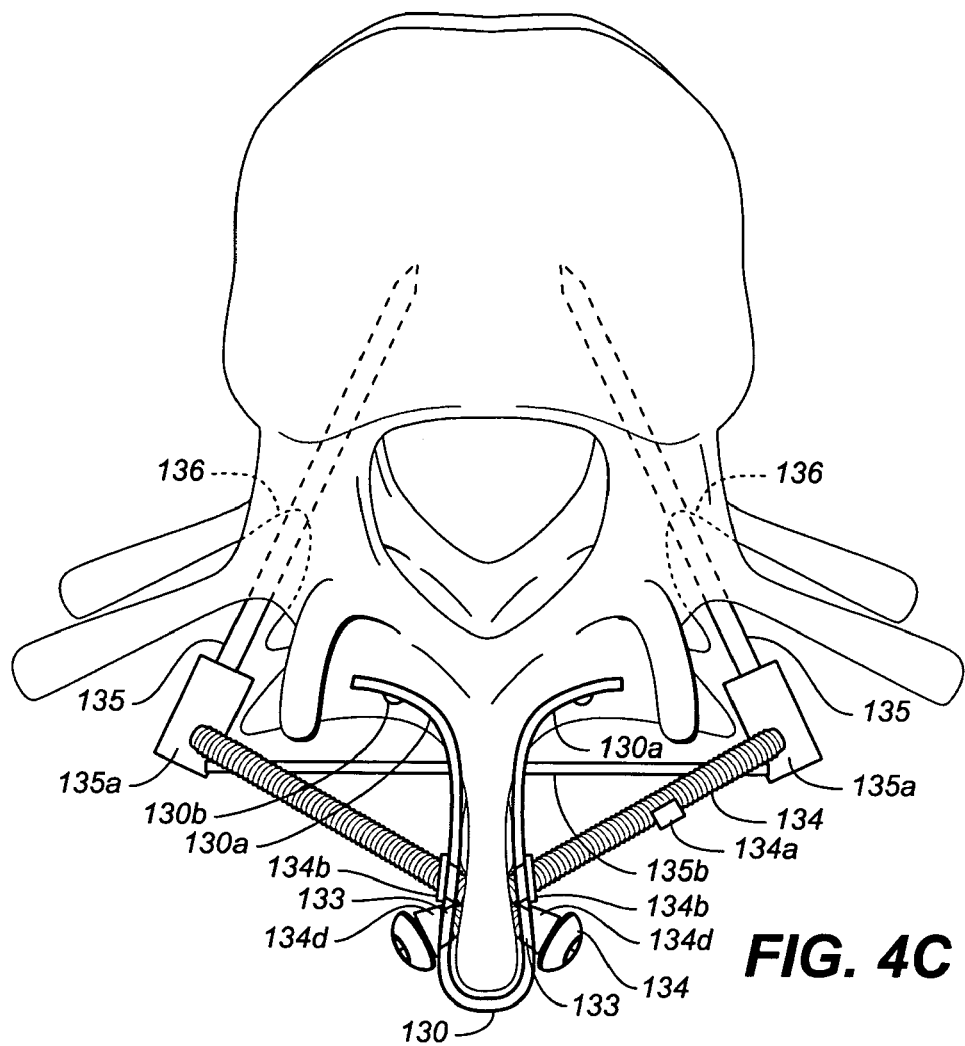
FIG. 4C is a top view of a reinforcement structure and implant in accordance with the invention.

Referring to FIGS. 4A-4D, a support structure 130 is illustrated positioned over a posterior portion 132 of a spinous process 131 with wings 130*a* over the lamina 103 including small screws 130*b* into lamina 103. Wings 130*a* may help spread the force from any devices attached or coupled to the support structure 130. Pedicle screws 135 are anchored into pedicles 136 and are further anchored into the spinous process 131 through screws 134 positioned through holes 133 in the support structure 130. As shown in FIG. 4C, the screw 134 includes a sensor 134*a* that may be used to sense loads on the device. Use of such sensors is described further herein. The pedicle screw 135 includes a screw capture device 135*a* for receiving a screw or rod of a spinous process screw or other rod. The capture device 135*a* may be a polyaxial head of a pedicle screw it may include a hole, a threaded screw hole with a washer or cap. Cross bar 135*b* is positioned across the spine between heads of pedicle screws 135 to prevent pedical screws from creeping laterally. A wedge shaped nut 134*d* between the head 134*c* of the screw 134 and the support structure. Another nut 134*b* may be positioned between support structure 120 and pedicle screw, and secure against the support structure 120. These features may be used in a similar manner in the embodiments described herein.

Figure 4D:
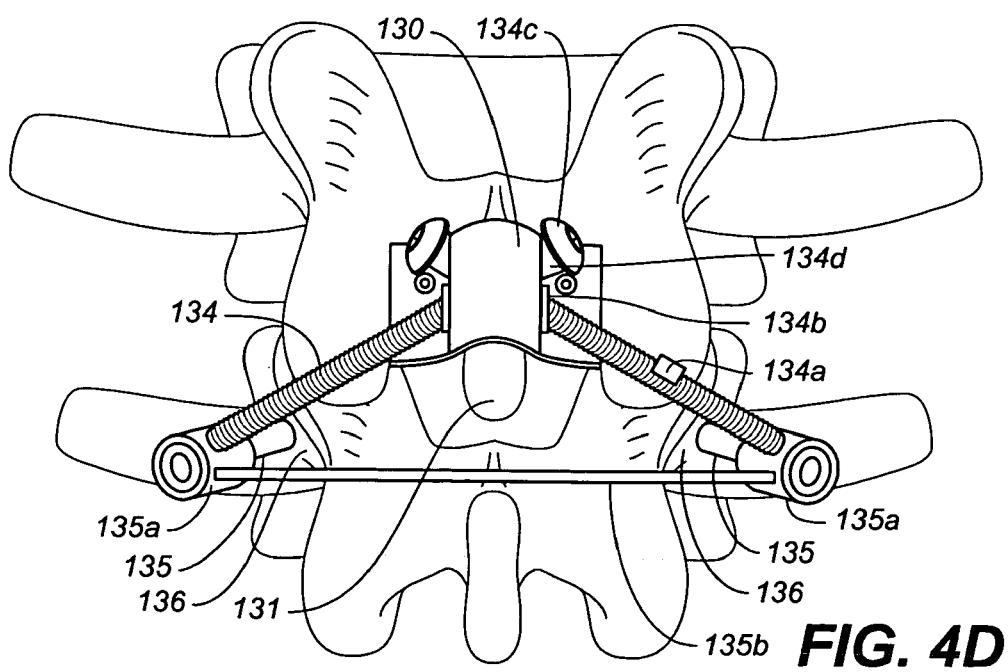
FIG. 4D is a posterior view of the reinforcement structure and implant of FIG. 4C.
Figure 5:
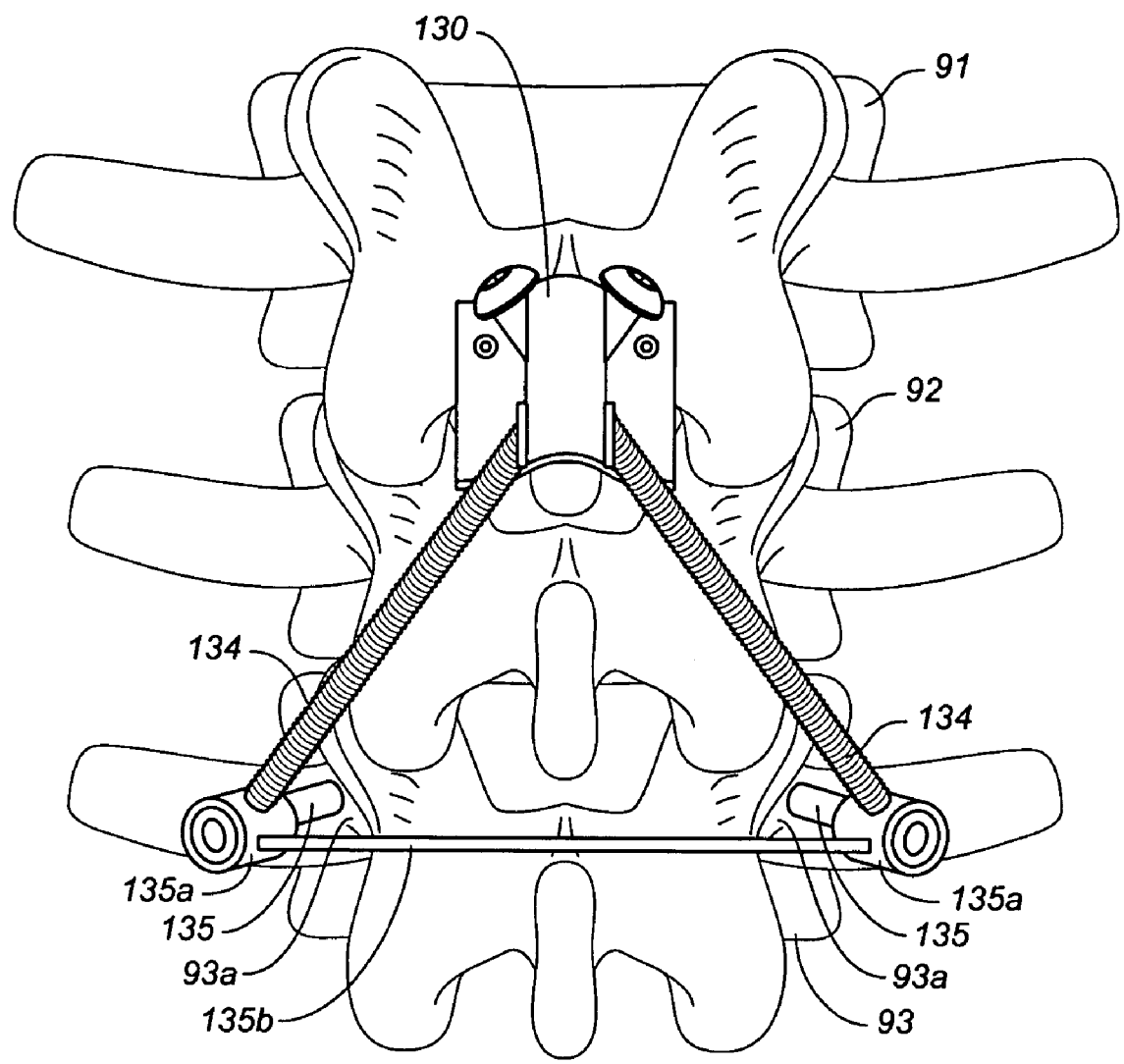
FIG. 5 is a posterior view of a reinforcement structure and implant in accordance with the invention.

FIG. 5 illustrates the spinous process screws 134 coupled to a spinous process 101 of a first vertebra 91 through a hood or support structure 130 in a manner similar to that described above with respect to FIGS. 4A-4D. The screws 134 extend bilaterally across the posterior of a second vertebra 92 and are anchored to capture elements 135*a* of pedicle screws 135 anchored into pedicles 93*a* of a third vertebra 93.

Figure 6:
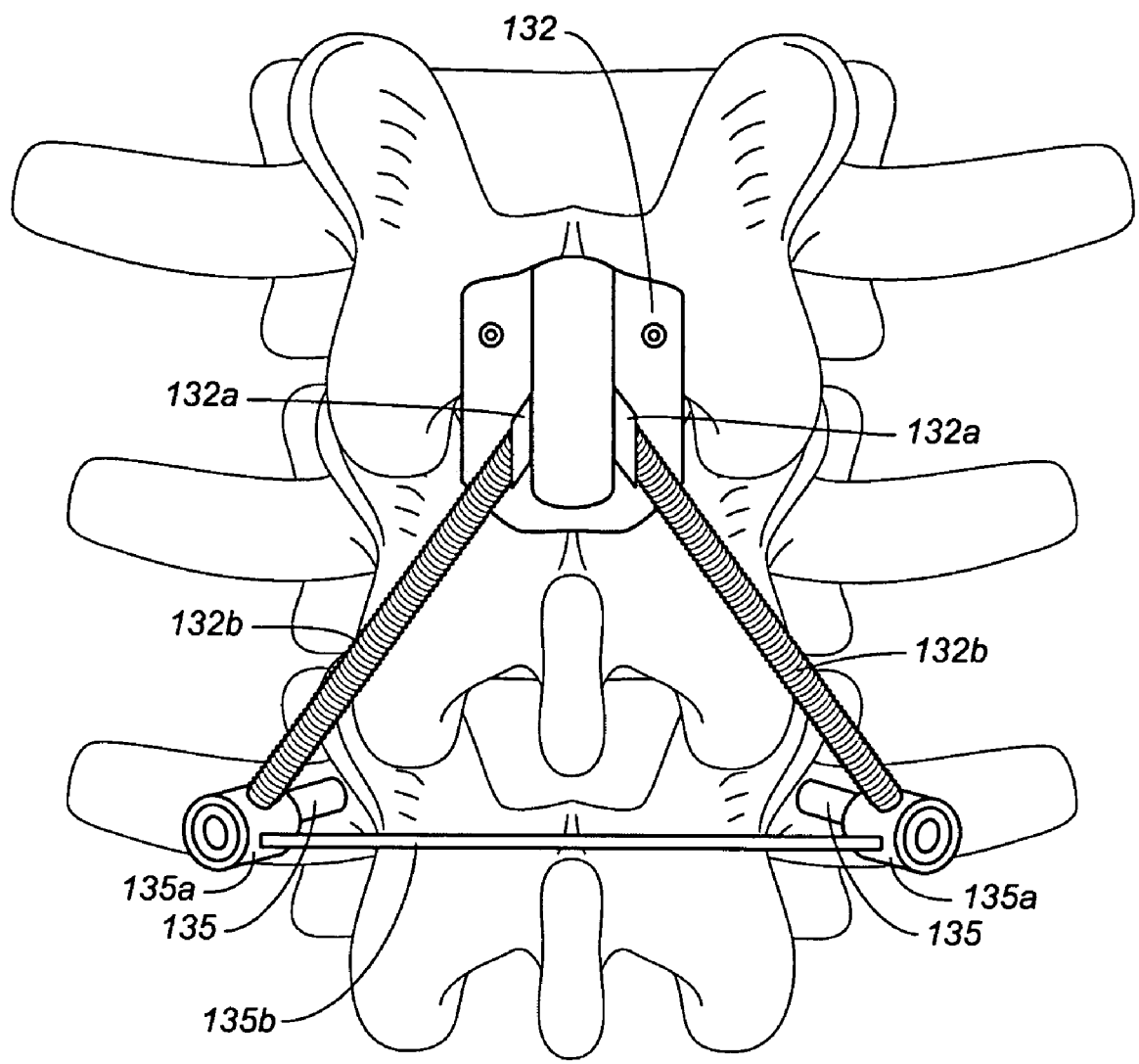
FIG. 6 is a posterior view of a reinforcement structure and implant in accordance with the invention

FIG. 6 illustrates a device for stabilizing or distracting the spine with pedicle screws 135 and cross bar 135*b* positioned as in FIG. 4D. Hood structure 132 includes openings for receiving screws 132*b* coupled to the hood 132 on one end and to the heads 135*a* of pedicle screws 135 and on the other end. The screws 132*b* do not penetrate the spinous process. Obliquely threaded nuts secure the screws 132*b* against the hood 132.

The reinforcement or supporting devices described herein may be used in conjunction with a number of different spine devices, including, for example, the various distraction, fusing or dynamic stabilizing devices described herein. The hoods or reinforcement devices herein may also be customized, for example by using stereolithography. The hoods or reinforcement devices may be used for example with a brace. The pedicle screw may be telescoping as described with respect to FIGS. 22C and 22D.

The devices described herein may be coupled to the spinous process using minimally invasive techniques. These techniques may include percutaneously accessing the spinous process and/or using dilators to access the spinous process at an oblique angle with respect to median plane m and/or horizontal plane h through the spine of the patient.

Figure 7A:
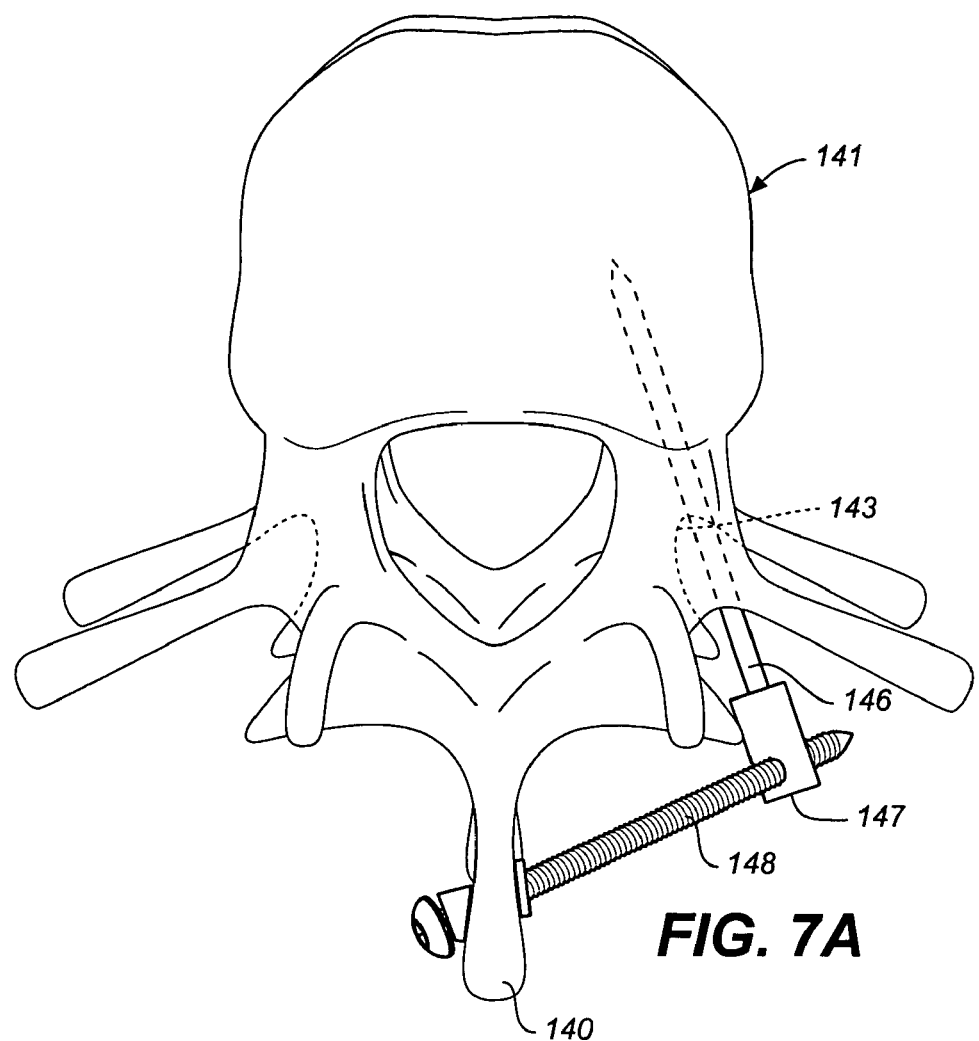
FIG. 7A is a top view of an implant implanted adjacent a motion segment in accordance with the invention.
Figure 7B:
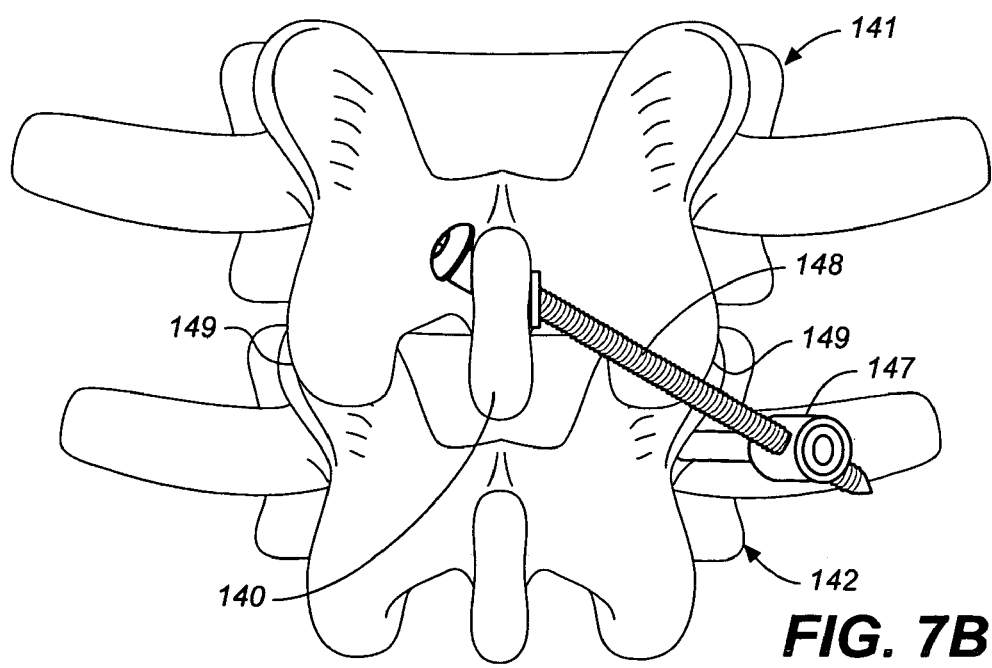
FIG. 7B is a posterior view of the implant as shown in FIG. 7A.

FIG. 7A is a side view of a joint of the spine with a fixation device percutaneously implanted to fuse adjacent vertebrae by fixation of the facet joints. Pedicle screw 146 in the pedicle 143 of the adjacent vertebral members 141, 142. As illustrated in FIG. 7B, the pedicle screw 146 has a polyaxial screw head 147 for receiving a spinous process screw 148 having a tapered tip. The spinous process screw 148 is screwed from the contralateral side of the spinous process, through the spinous process 140 of vertebral member 141, adjacent the facet joint 149 between the vertebral member 141 and vertebral member 142, and then captured or placed into the head 147 of the pedicle screw 146.

When implanted, the pedicle screws are positioned in the pedicles in a generally known manner. The facet joint or facet joints between the spinal members that are to be fused, are debrided and grafted. A flank stab wound is made to expose the base of the spinous process. The spinous process screw is then inserted and navigated through the wound to the spinous process and/or soft tissue. Tissue dilators or retractors may be used to facilitate insertion of the spinous process screw through soft tissue. The spinous process screw 148 is then placed through the spinous process 140, and into and captured by the head 147 of the pedicle screw 146. Compression across and the facet joint 149 may be provided using a nut placet in the polyaxial head of the pedicle screw. Alternatively, external compression may be used prior to placement of the oblique rod of the spinous process screw. A similar screw may also be placed from the spinous process 140 to the contralateral pedicle. The spinous process 140 may be reinforced prior to or after placing the screw 148.

Figure 8A:
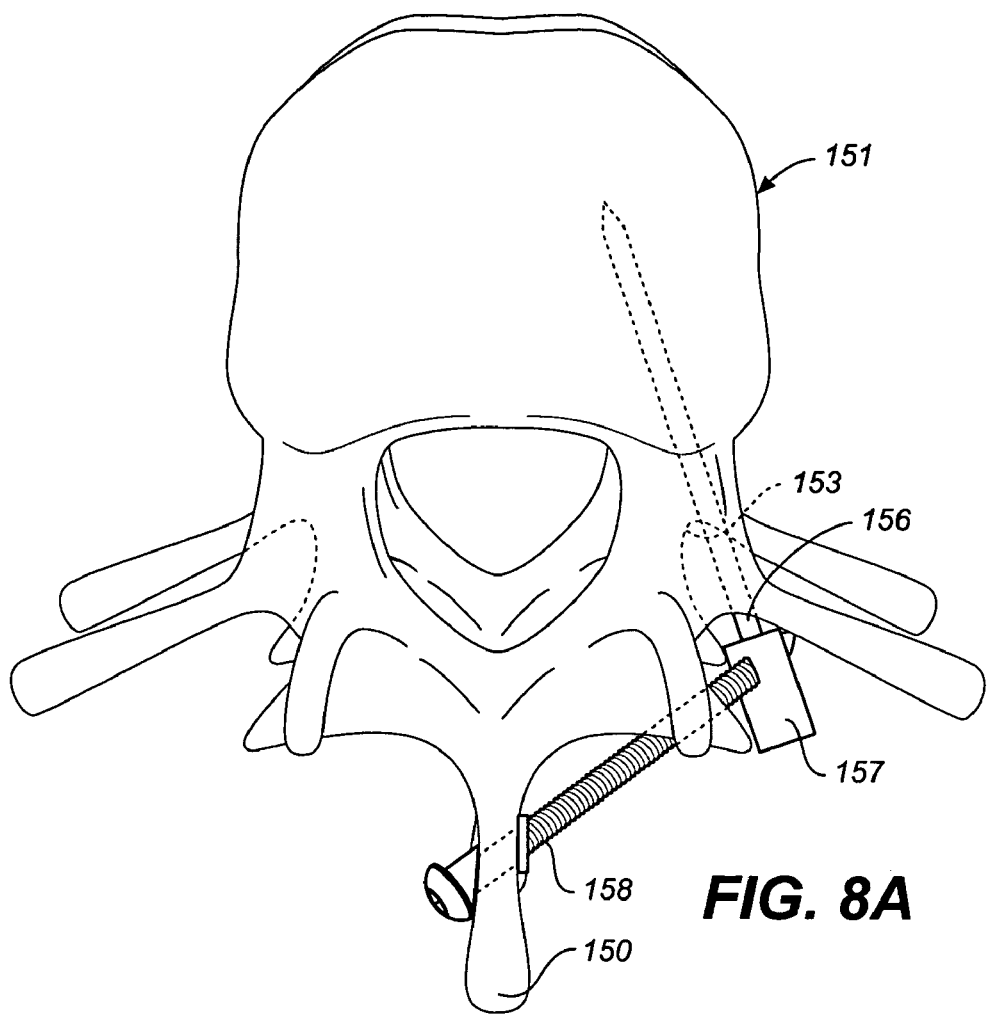
FIG. 8A is a top view of an implant implanted through the lamina and the zygapophyseal joint in accordance with the invention.
Figure 8B:
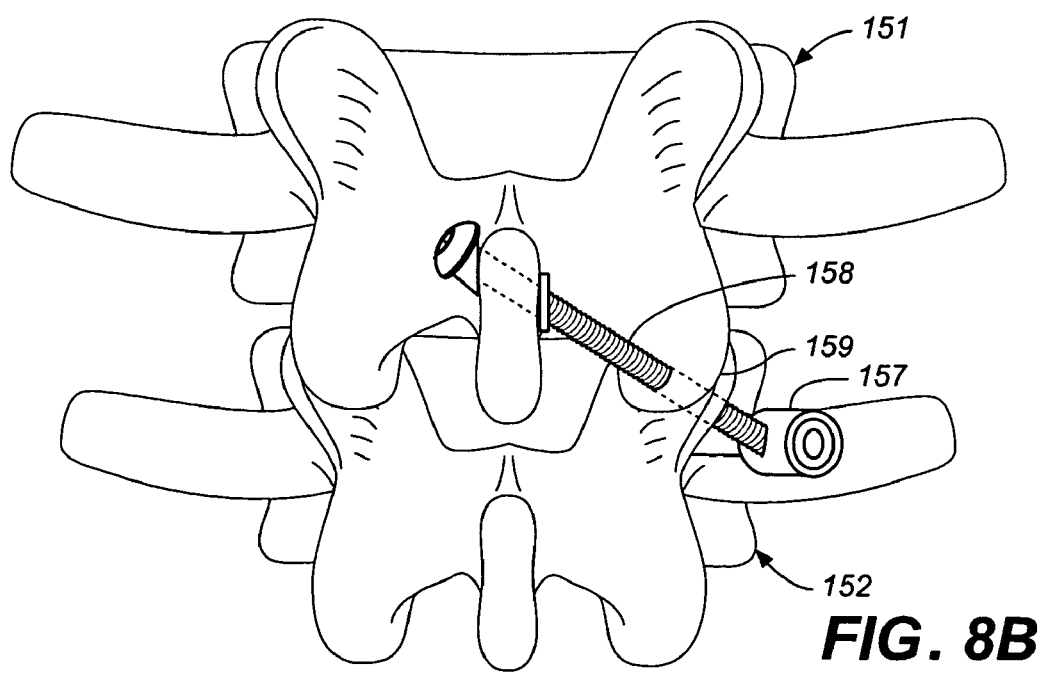
FIG. 8B is a posterior view of the implant as shown in FIG. 8A.

Referring to FIG. 8A, a similar fusion system as illustrated with respect to FIGS. 7A and 7B. Pedicle screw 156 is positioned in the pedicle 153 of the adjacent vertebral members 151, 152. The pedicle screw 156 has a polyaxial screw head 157 for receiving a spinous process screw 158 having a tapered tip. The spinous process screw 158 is screwed from the contralateral side of the spinous process 150, through the spinous process 150 of vertebral member 151, through the facet joint 159 between the vertebral member 151 and vertebral member 152 and then into the head 157 of the pedicle screw 156.

An oblique skin stab wound is made to navigate to the base of the spinous process 150, which may be exposed under direct vision. The spinous process screw 158 (or other device) is then placed through the spinous process 150, across (adjacent or through) the facet joint 159, and into the head 157 of the pedicle screw 156 (or otherwise attached to a pedicle attachment device for attaching devices to the pedicle), immobilizing the facet joint 159. A similar screw may also be placed from the spinous process 150 to the contralateral pedicle. The spinous process may be reinforced prior to or after placing the screw or other device. The other devices attached or coupled to the spinous process as described herein may be similarly deployed.

The devices described herein may be coupled to the spinous process using minimally invasive techniques. These techniques may include percutaneously accessing the spinous process and/or using dilators to access the spinous process at an oblique angle with respect to median plane and/or horizontal plane through the spine of the patient.

Figure 9A:
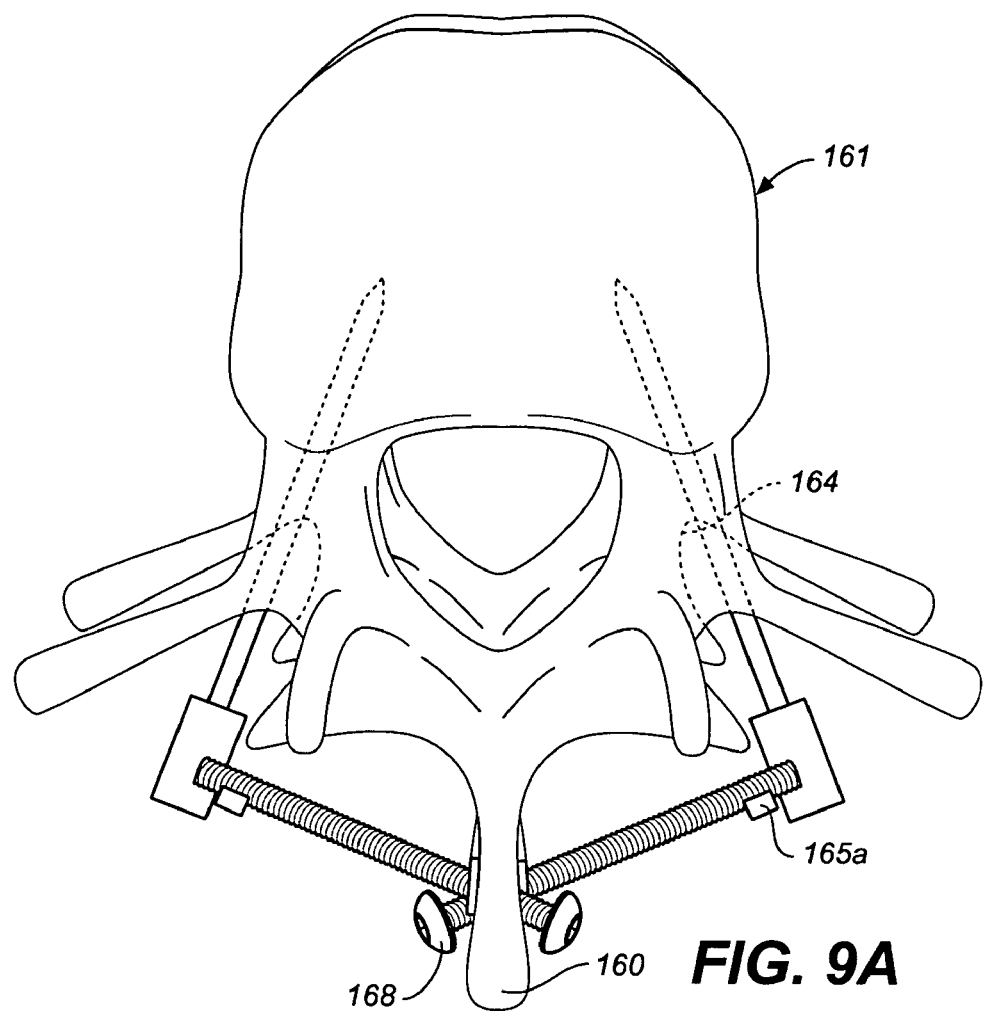
FIG. 9A is a top view of a dynamic implant in accordance with the invention.
Figure 9B:
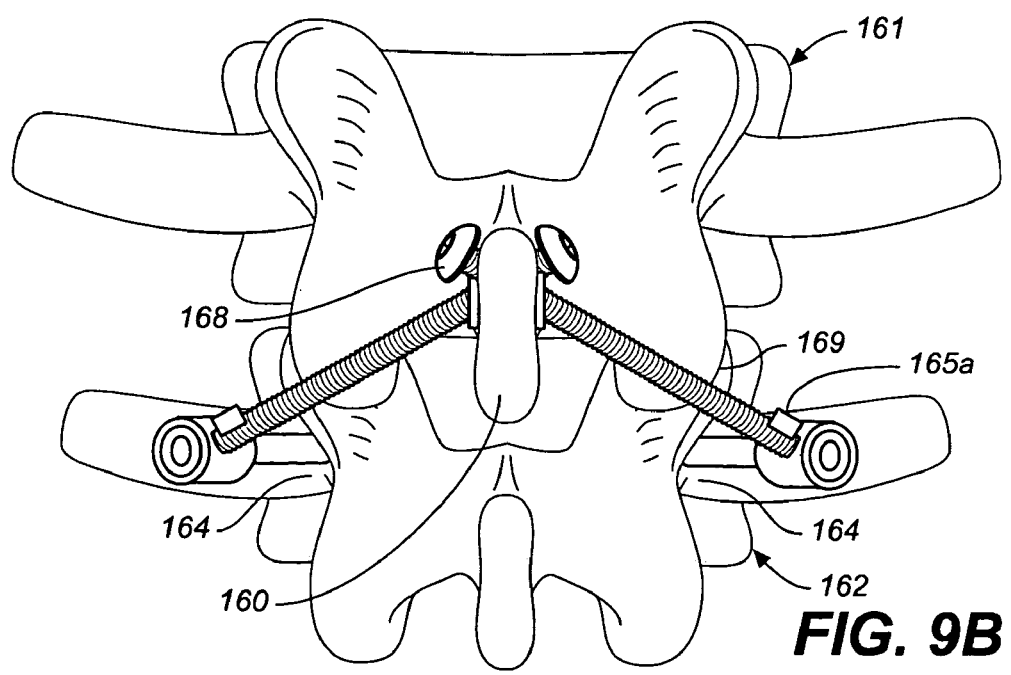
FIG. 9B is a posterior view of the implant as shown in FIG. 9A.

Referring to FIGS. 9A and 9B, a spine is illustrated with a spinal fusion system in place. A spinous process screw 168 is placed from the contralateral side of the spinous process 160, through the spinous process 160 of a first vertebra 161 and across the facet joint 169 between the first vertebra 161 and adjacent second vertebra 162, and into the pedicle 164 of the second vertebra 162.

Another feature of the spinous process screw of FIGS. 9A-9B is that it may be configured to exert flexible, stabilizing, nonfusion forces to the motion segment. For example, this may be used in the event that patient suffers from pain due to laxity or other dysfunction of the spinal structures (e.g. degenerative spondylolisthesis). In other words, the looseness or other dysfunction of the joint and surrounding tissue may cause pain. The present invention provides a device and method for dynamically stabilizing (or reducing) such a joint while allowing some flexibility and movement. The device and method provide such stabilization on an oblique angle with respect to the rotational axis of the spine, i.e. at an oblique angle with respect to the median and horizontal planes of the spine. The spinous process and a pedicle could also be used to anchor a device exerting a stabilizing or compression or contractile force between the two anchors on an oblique angle. Devices that may be used to exert such a contractile force may include, for example, polymeric materials, super elastic metals, and fabrics. The spinous process screw 168 includes a sensor 165a that may be used to sense motion of the distraction device. The forces or stresses on the device may be monitored and used to determine if it is necessary to convert the device to a fusion type device or to otherwise reduce or alter motion. The sensor may also be used as a diagnostic device to measure the amount of joint motion upon insertion of the implant or over time.

The system illustrated in FIGS. 9A and 9B may also be used for the treatment of spondylolysis, to attain stability across the pars interarticularis.

The spinous processes 140, 150, 160 may be reinforced in a manner as described herein. The various rods or screws through the spinous processes 140, 150, 160 may also be positioned through a posterior arch reinforcing member as described herein.

Figure 10:
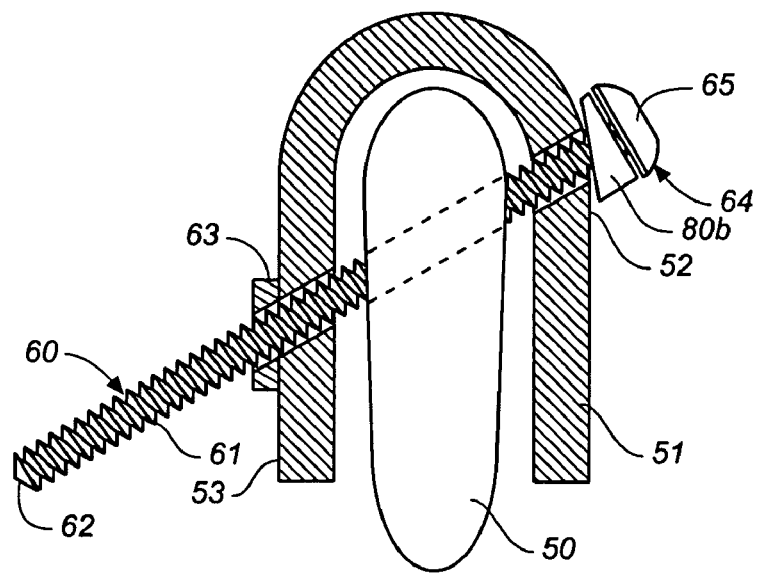
FIG. 10 is a schematic posterior portal cross sectional view of a reinforcement device and implant in accordance with the invention.

FIG. 10 illustrates a spinous process rod or screw 60 in accordance with the invention. The spinous process rod or screw 60 comprises an elongate portion 61 configured to extend through the reinforcement hood 51 (for example, as described in further detail herein with reference to FIGS. 3A-4D) positioned around spinous process 50 and into an adjacent element such as, e.g. a pedicle screw. The spinous process rod or screw 60 may include threaded portions. The distal end 62 of the rod may be threaded or otherwise configured to engage an adjacent element. The spinous process screw or rod 60 further comprises a proximal securing element 65 located on the proximal portion 64 of the spinous process screw or rod 60. The proximal securing element 65 is configured to engage a first wall 52 portion of the spinous process 60 or reinforcement hood 51. ("Engage" as used herein means to either directly or indirectly engage.) As illustrated, the distal securing element 63 comprises an obliquely threaded nut that is configured to receive screw 61 which is coupled to the hood 51 at an oblique angle with respect to the wall 53. The oblique threaded nut may be used in other applications where a screw is oblique with respect to the abject to which is engaged, coupled or attached. The obliquely threaded nut may have a predetermined angle at which it directs the screw with respect to the hood to guide the desired angle or directions of the screw placement. This may be predetermined base on imaging of a particular patient's anatomy. A distal securing element 63 is provided more distal of the proximal securing element 65. The distal securing element is configured to engage a second wall portion 53 generally opposite the first wall portion 52 so that the spinous process element is secured or fixed to the hood and spinous process. (The term "fix" as used herein means either directly or indirectly fix to and may include dynamic elements.)

Figure 11:
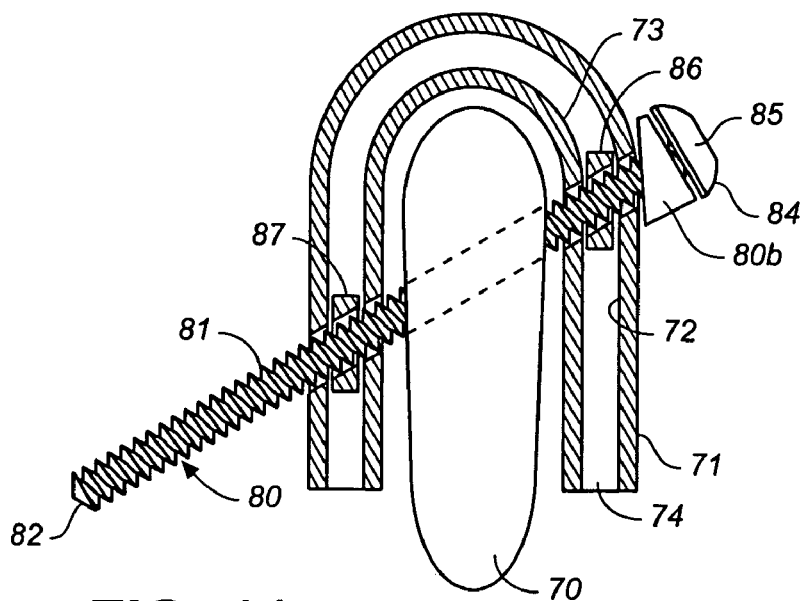
FIG. 11 is schematic posterior partial cross sectional view of a reinforcement device and implant in accordance with the invention.
Figure 12A:
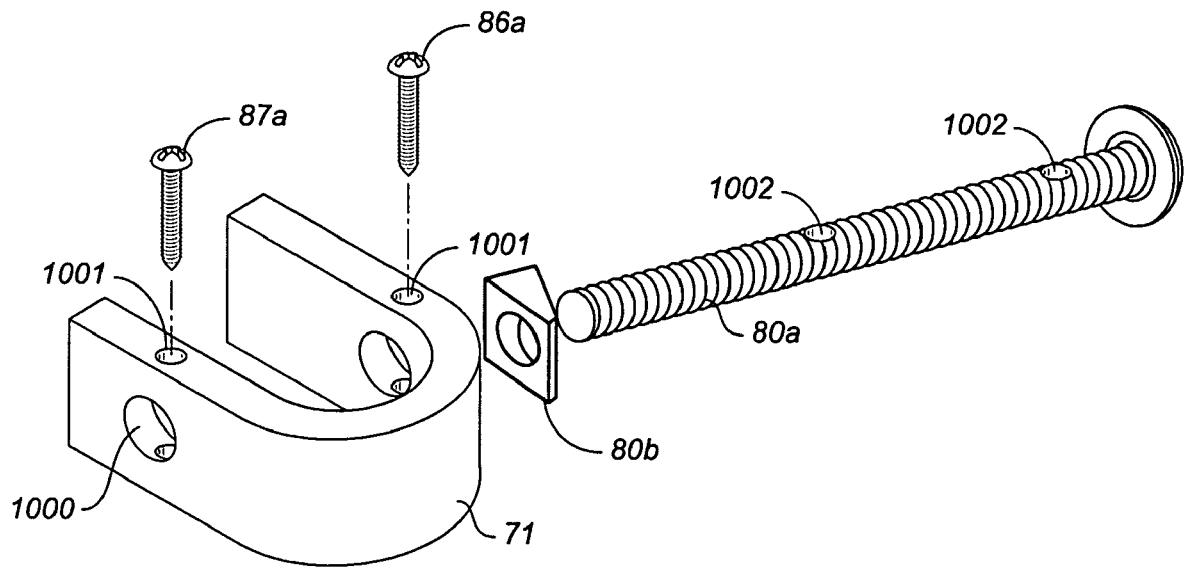
FIG. 12A is an exploded perspective view of a reinforcement device and implant in accordance with the invention.
Figure 12B:
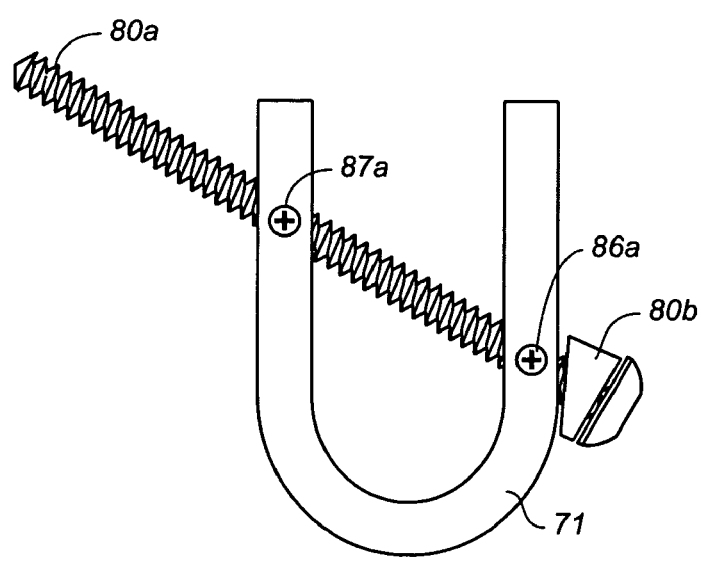
FIG. 12B is a top view of the reinforcement device and implant of FIG. 12A.
Figure 13A:
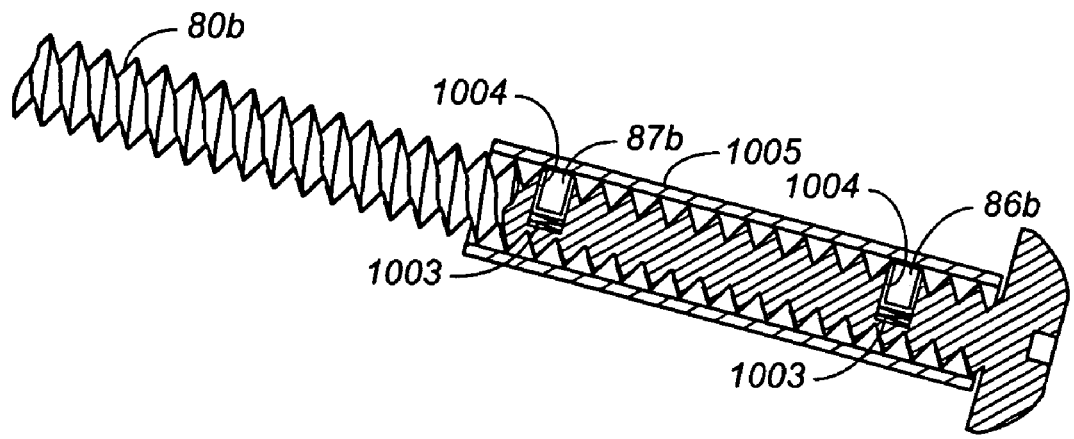
FIG. 13A is a schematic partial cross sectional view of an implant in accordance with the invention in a first position.
Figure 13B:
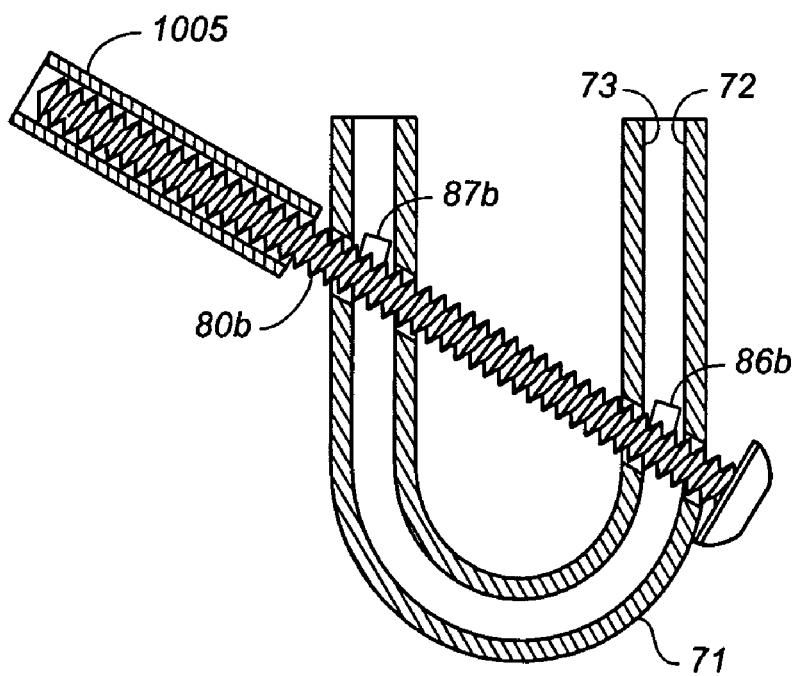
FIG. 13B is a schematic partial cross sectional view of the implant of FIG. 13A in a second, and implanted position.

FIG. 11 illustrates a spinous process rod or screw 80 in accordance with the invention. The spinous process rod or screw 80 comprises an elongate portion 81 configured to extend through the reinforcement hood 71 (for example, as described in further detail herein with reference to FIGS. 3A-4D) positioned around spinous process 70 and into an adjacent element such as, e.g. a pedicle screw. The spinous process rod or screw 80 may include threaded portions. The distal end 82 of the rod may be threaded or otherwise configured to engage an adjacent element, e.g. with a connecting member, including but not limited to connecting members described herein. The spinous process screw or rod 80 further comprises a proximal securing element 85 located on the proximal portion 84 of the spinous process screw or rod 80. The proximal securing element 85 is configured to engage a first wall 72 portion of the spinous process 70 or reinforcement hood 71. ("Engage" as is used herein to mean either directly or indirectly engage.) A hollow space or chamber 74 is formed in the reinforcement hood 71 so that the hollow chamber may engageably receive one or more securing elements, e.g. first and second securing elements 86, 87 therein. The securing elements 86, 87 may be positioned on either or both sides of the spinous process 70 through which the screw or rod 80 is positioned. As illustrated in FIG. 11, securing element 86 is positioned on the proximal portion 84 of the screw 80 while securing portion 87 is positioned on the distal portion 82 of the screw 80. Securing elements 86, 87 may be obliquely threaded nuts, for example, as described with respect to nut 80b in FIG. 3E. Securing elements may be attached a variety of ways, for example as illustrated in FIGS. 12A-12B and 13A-13B. FIGS. 12A-12B illustrate manual insertion of securing elements in accordance with the invention. Spinous process screw 80a is placed through both wings of the hood 71 while passing through holes 1000 as shown. Securing elements 86a and 87a are inserted into receiving holes 1001 within the hood 71 and receiving holes 1002 within the spinous process screw 80a. Securing elements 86a, 87a prevent movement of the spinous process screw 80a. FIGS. 13A-13B illustrate automatic deployment of securing elements in accordance with the invention. The securing elements 86b and 87b could be positioned in recesses 1004 in the spinous process screw 80b and spring loaded with springs 1003 attached inside of the recesses 1004. An external sheath 1005 is positioned around the spinous process screw 80b. The screw 80b is positioned through a spinous process and a hood. The securing elements are then deployed upon removal of an external sheath 1005. The securing element 86, 86a, or 86b is configured to engage the first wall portion of the spinous process (or hood) from within the hood 71. The securing element 87, 87a, or 87b is configured to engage a second wall portion 73 generally opposite the first wall portion 72 so that the spinous process element is secured to the hood and spinous process.

One aspect of the present invention provides a distraction device that distracts the joint in an upward or in less of a forward bending manner diminishing kyphosis formation. A distraction device in accordance with the invention lessens spinal stenosis and reduces stress on the facet joints. In accordance with one aspect of the invention, narrowing or stenosis of the neural foramen may be treated using a device configured to distract the facet joint.

In accordance with one aspect of the invention, a distraction system is provided where the system is anchored on opposite sides of a motion segment that would benefit from distraction. According to an embodiment, on opposite lateral sides of the motion segment, an expandable rod, screw, or other columnar support structure is attached. The length of the support structure may be adjusted to determine the degree or amount of distraction. Additionally, a spring or shock-absorbing element may be included in the distraction device. In accordance with one aspect of the invention, such distraction device may provided with screws 134 as illustrated in FIGS. 4A and 4D.

One aspect of the invention contemplates use of orthopedic implants that can be remotely lengthened after surgery, as needed. For example, the gait of patients after hip replacement surgery may be effected if the leg length of one limb is longer or shorter than the other. This invention would allow doctors to change the implant's length over time as needed to help restore normal gait. Other indications include surgical procedures where an external fixator is used in long bone fractures. According to the invention a distractor as described may be affixed at opposite ends, to opposite sides of other structures of the body, including, for example a hip joint. The distractor may be remotely actuated or less invasively accessed for distraction adjustments, including, e.g., post operatively, over the life of the prosthetic implant, or over time.

A variety of distraction systems are contemplated for distracting the adjacent vertebrae (including but not limited to the distractions systems disclosed herein), e.g., an expandable screw or rod or plate, telescoping implant, a distraction jack, an inflatable column, a column that lengthens when exposed to heat, fluids, ultrasound, or other biological, physical, or chemical catalysts (using, for example, a device constructed of a shape memory alloy or rheostatic fluids). The amount of distraction may be controlled remotely, by radiofrequency, electromagnetic energy, electrical, heat, ultrasound, and other means. The distracting member for example may comprise a remotely actuated realignment device or solenoid. The distraction may also be adjusted percutaneously or remotely according to one of these variations. The adjustments may be made over time, particularly if the disease progresses or other anatomical changes occur. This would allow adjustment of the amount of distraction as needed to a patient's symptoms long after surgery. The distraction adjustment may also be done with patient feedback. The distraction devices may also include a variety of different types of sensors that sense changing loads on the spine or on the device. For example, the distraction device may include a pressure sensor or a strain gauge. As noted above, the distraction device with spring properties may include a freeze or lock (for example, as described with respect to FIGS. 41-40 herein) that permits the device to be immobilized should a fusion type procedure be necessary to immobilize a patient's spine, for example at a later date with further wear or progression of disease. The flexibility or stiffness of the device may also be incrementally or progressively adjusted as described with respect to FIGS. 41-40 herein.

The distraction device may also include a fuse like feature or a predetermined failure feature so that the device breaks first before a bone fractures from stresses related to the device implant. This may be accomplished by determining the approximate failure properties of the bones at the location of implant and by designing the distraction rod to fail at a force below the force required to fracture the bone.

Figure 17:
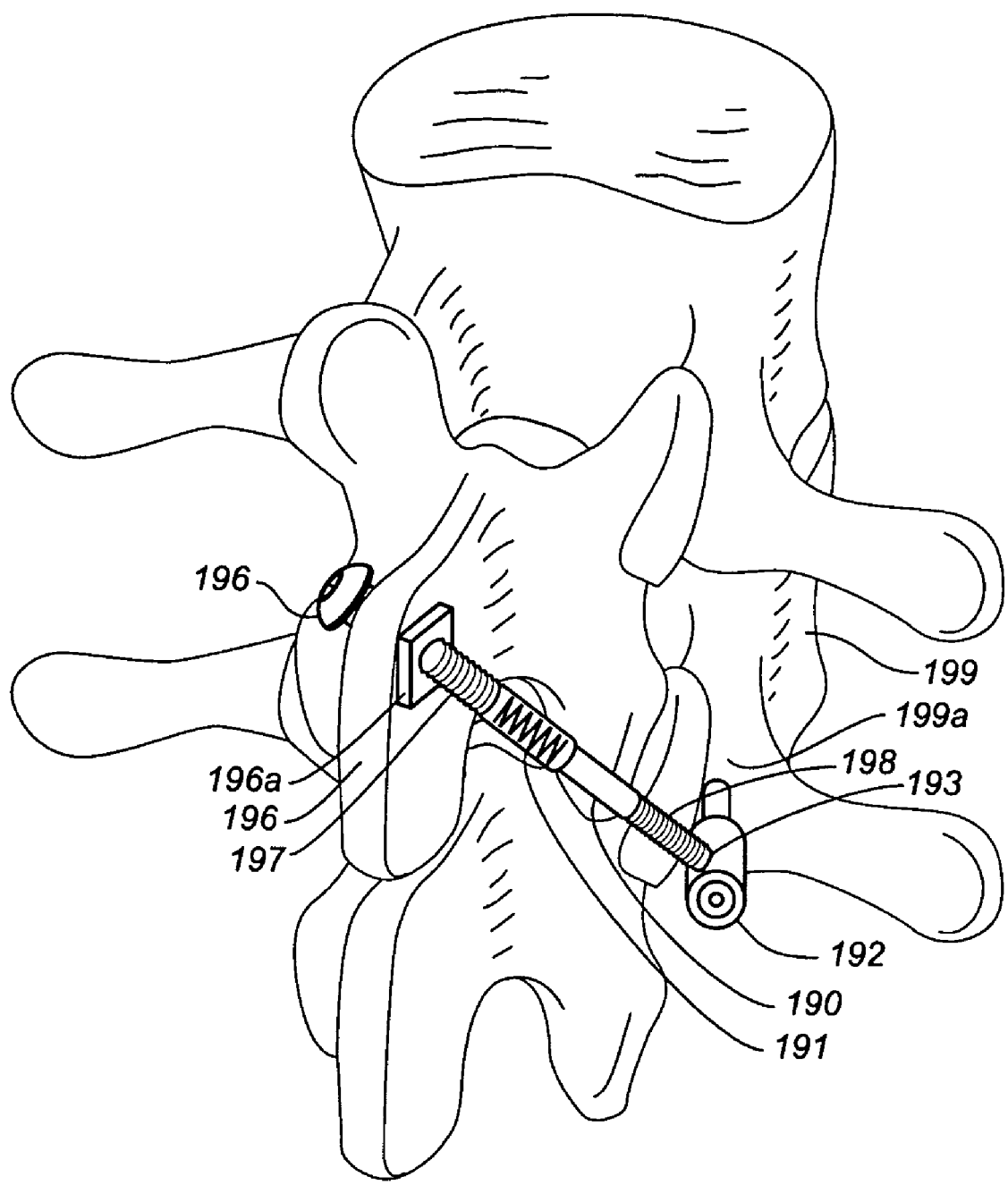
FIG. 17 is a posterior lateral perspective view of an implant implanted in accordance with the invention.

Referring to FIG. 17, a distraction system in accordance with the invention is illustrated where the distraction device is anchored to a pedicle from one level and a spinous process of an adjacent level. In this particular embodiment, the distraction system is positioned from the spinous process of a superior vertebra to the pedicle of a lower or inferior vertebra. The distraction system of an embodiment includes a rod attached or fixed to a spinous process and coupled to a pedicle attachment device that is attached to the pedicle. The pedicle attachment device illustrated in this embodiment comprises a pedicle screw. However, other pedicle anchors or pedicle attachment devices or mechanisms are contemplated herein. The distraction rod 190 may include any of the features of the various distraction rods described herein, for example, the distraction rod may include a distraction element, the distraction rod 190 may adjustable in length in various ways, may be adjustable by different mechanisms including remotely or minimally invasively, and/or the distraction rod 190 may include shock absorbing features or locking features features. The distraction system includes a pedicle screw 192 with a threaded opening 193 for receiving the distraction rod 191. The distraction rod 191 is configured to be anchored to the spinous process 194 of a first vertebra 195 by a rod portion (or screw) 197 extending through the spinous process 194 and having a head 196 holding the rod portion 197 on to the spinous process 194. The a threaded distal end 198 of the rod portion 197 extends into the threaded opening 193 of the pedicle screw 192 which is implanted in the pedicle 199a of a second vertebra 199, and thereby mechanically coupling the first and second vertebrae 195, 199. The distraction rod 190 is implanted so that there is an oblique (i.e., with respect to a median and/or horizontal plane) exertional force between the spinous process 194 of the first vertebra 195 and the pedicle 199a of the second vertebra 199. The distraction rod 190, when in position, operates to exert a separating force in a direction that separates the two vertebrae 195, 199. The distraction rod 190 may be attached to the pedicle screw 192 either before, during or after distraction occurs. An obliquely threaded nut 196a such as nut 80b described with respect to FIG. 10, may tighten screw against the spinous process 194. The spinous process 194 may be reinforced in a manner as described herein. The distraction rod 190 may also be positioned through a posterior arch reinforcing member as described herein. A second distraction rod (not shown) is positioned on the contralateral side of the spinous process 194 and through the contralateral pedicle of the second vertebra 199. The distraction rod 190 is positioned at an oblique angle such that it relieves load from the facet joint between the vertebrae 195, 199. It is believed that relieving the load will decrease pain, slow degeneration of the spine, and reduce formation of osteophytes. Sensors and fracture points may be included with the distraction rod 190 in a similar manner as distraction rod 185 herein.

Figure 18:
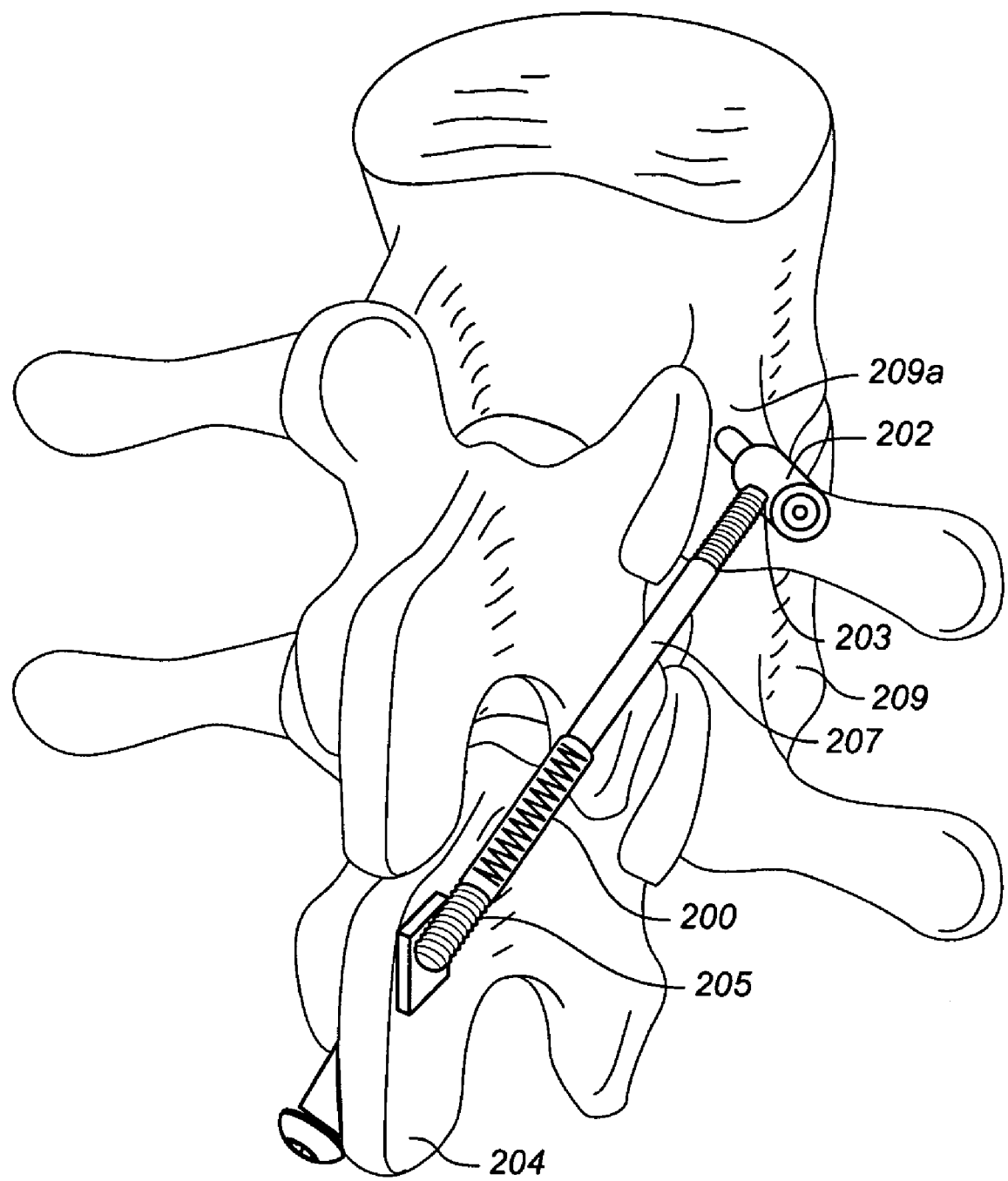
FIG. 18 is a posterior lateral perspective view of an implant implanted in accordance with the invention.

Referring to FIG. 18, a distraction system in accordance with the invention is illustrated where the distraction device is anchored to a pedicle from one level and a spinous process of an adjacent level. As opposed to the distraction system in FIG. 17, in this particular embodiment, the distraction system is positioned from the spinous process of an inferior or lower vertebra through the pedicle of a superior vertebra. The distraction system of one embodiment includes a rod attached or fixed to a spinous process and coupled to a pedicle attachment device that is attached to the pedicle. The location and angle of the distraction rod may be selected depending on the desired load bearing properties of the distraction system, i.e., depending upon the anatomy the symptoms or prognosis of the patient. The distraction rod 200 may include any of the features of the various distraction rods described herein, for example, the distraction rod 190 may adjustable in length in various ways, may be adjustable by different mechanisms including remote or minimally invasively, and/or the distraction rod 200 may include shock absorbing features or locking features features. The distraction system includes a pedicle screw 202 with a threaded opening 203 for receiving the distraction rod 200. The distraction rod 200 is configured to be anchored to the spinous process 204 of a first vertebra 205 by a rod portion (or screw) 207 extending through the spinous process 204 and having a head 206 holding the rod portion 207 on to the spinous process 204. The a threaded distal end 208 of the rod portion 207 extends into the threaded opening 203 of the pedicle screw 202 which is implanted in the pedicle 209a of a second vertebra 209, and thereby mechanically coupling the first and second vertebrae 205, 209. The distraction rod 200 is implanted so that there is an oblique exertional force between the spinous process 204 of the first vertebra 205 and the pedicle 209a of the second vertebra 209. The spinous process 204 may be reinforced in a manner as described herein. The distraction rod 200 may also be positioned through a posterior arch reinforcing member as described herein. A second distraction rod (not shown) is positioned on the contralateral side of the spinous process 204 and through the contralateral pedicle of the second vertebra 209. The distraction rod 200 is positioned at an oblique angle such that it relieves load from the facet joint between the vertebrae 205, 209. It is believed that relieving the load will decrease pain and reduce formation of osteophytes and increases space for nerves. Sensors and fracture points may be included with the distraction rod 200 in a similar manner as distraction rod 185 herein.

The distraction rods as disclosed herein may also be anchored at oblique angles to different portions of the bony posterior of a vertebra, including but not limited to the lamina, pedicle spinous process and transverse process.

FIGS. 16A and 16B illustrate an enlarged view of the distraction rod 190 of FIG. 17. The distraction rod 190 in which distracting element 179n comprises two opposing rods 179a, 179b with abutting ends 179c 179d and an adjusting device 179e connecting the threaded abutting ends 179c, 179d. In FIG. 9A the ends 179c, 179d of the opposing rods are immediately adjacent each other and the length $l_1$ of the rod is relatively shorter. In FIG. 16B, the extension by the adjusting device 179e has moved relatively longer. The ends 179c 179d apart from each other and the length $l_2$ of the distraction rod 179 is distraction rod 190 is operable to be extended and locked into an extended position whereby a joint is distracted. The distraction rod 190 may be extendable after implanted to slowly distract the joint until a desired result (e.g., reduction of patient pain or discomfort) is achieved or degree of release of stress on a joint is achieved. This can be visually determined, determined according to patient feedback or determined by a sensor 170a positioned on or adjacent the implanted distraction system 170. (Here it is near the attachment site to the bone.) The sensor 170a may be a strain gauge, an accelerometer, a a piezo-electric film or other sensor that can be used, positioned or configured to determine a mechanical load on the distraction device. The sensor 170a may also be a stand alone sensor positioned in or adjacent a distracted joint and configured to sense a parameter indicative of forces at the joint. The sensor may include an electronic circuit that is configured to telemetrically send a signal containing information correlated to such sensed forces. The electronic circuit may be a passively powered device from an external power source where the external device may interrogate the sensor for information. The electronic circuit may also include signal processing circuits or memory. The distraction rod 190 may include a remotely actuable length adjusting device. For example, the distraction rod 190 may include a mechanical, magnetic or other adjusting device such as a small machine (e.g. a solenoid, a piezoelectric motor or other electromechanical device) that may actuate or move the rod to adjust the degree of distraction. The adjusting device 179e may be actuable by the patient or provider or may automatically adjust, may be adjusted by circuit 179f (that may be telemetrically controlled and/or powered) or may adjust the distraction on demand based at least in part on information sensed by the sensor 170a via control signal through electronic circuit 179f. The distraction rod 190 may also include a predetermined mechanism that is designed to break or fail when a certain force is applied to the device. One or ordinary skill in the art may design the device to release, disengage, fail or break with application of a predetermined or selected force by creating a release mechanism or faults in the material or selecting material or structure specifications. For example the device may be constructed to operate under given normal operating forces but to release, disengage, fail or break prior to a force sufficient to fracture the bone.

FIGS. 16C and 16D illustrate an enlarged view of a variation of a distraction element that may be used with any distraction device or rod described in accordance with the invention. The distraction element 180 comprises opposing rods 181, 182 with rod 181 slidably positioned at least partially within rod 182. The rods 181, 182 longitudinally slide with respect to one another to vary the total length of the distraction element 180. The inner wall of the rod 182 and outer wall of the rod 181 are configured to engage with a detent mechanism, cammed surface or other interference type fit mechanism, when the rods 181, 182 are rotated or actuated or distracted with respect to each other to thereby fix the length of the distraction element 180. FIG. 16C illustrates the distraction element 180 with a relatively shorter length of $l_3$ and FIG. 16D illustrates the distraction element 180 with a relatively longer length of $l_4$. The rods 181, 182 may also be simple telescoping tubes that can be crimped or welded or ratcheted together when a desired distraction length is determined.

Referring to FIG. 16E a distraction element 185 that may be used with a distraction device, is illustrated containing a coil or spring-like member 186 where the spring is longitudinally biased so that the coil tends to lengthen, providing a distraction type force. shock absorbing properties. The distraction element 185 may be converted into a rigid or less flexible distraction rod or may be adjusted in flexibility in a manner as described with respect to the devices illustrated in FIGS. 41-40 herein.

Referring to FIG. 16F a distraction element 188 that may be used with a distraction device in accordance with the invention, is illustrated with a spring 189 on one end. The spring 189 is longitudinally biased in a lengthening direction as the spring member 186 described herein with reference to FIG. 16E. The spring 189 is configured to permit movement in a plurality of directions and/or planes. A rubber member 189a is positioned inside the coil and acts to dissipate energy or absorb shock. Thus, the distracting rod 188 provides a distracting force in combination with shock absorbing properties. The rod 188 may also be converted to a rigid distraction rod in a manner described above with reference to the distraction rod 185.

Figure 31A:
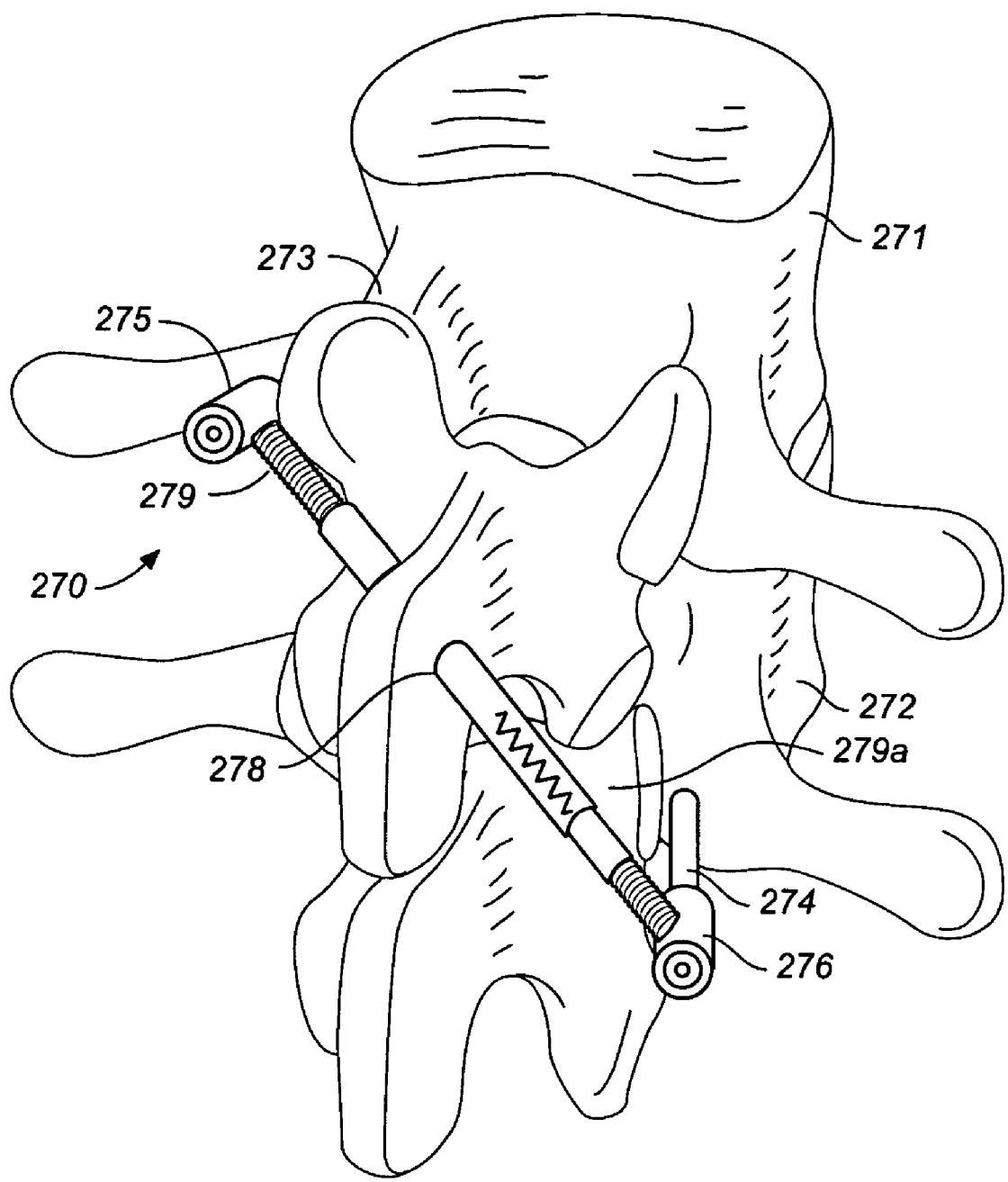
FIG. 31A is a posterior lateral perspective view of an implant adjacent a removed joint segment in accordance with the invention.
Figure 31B:
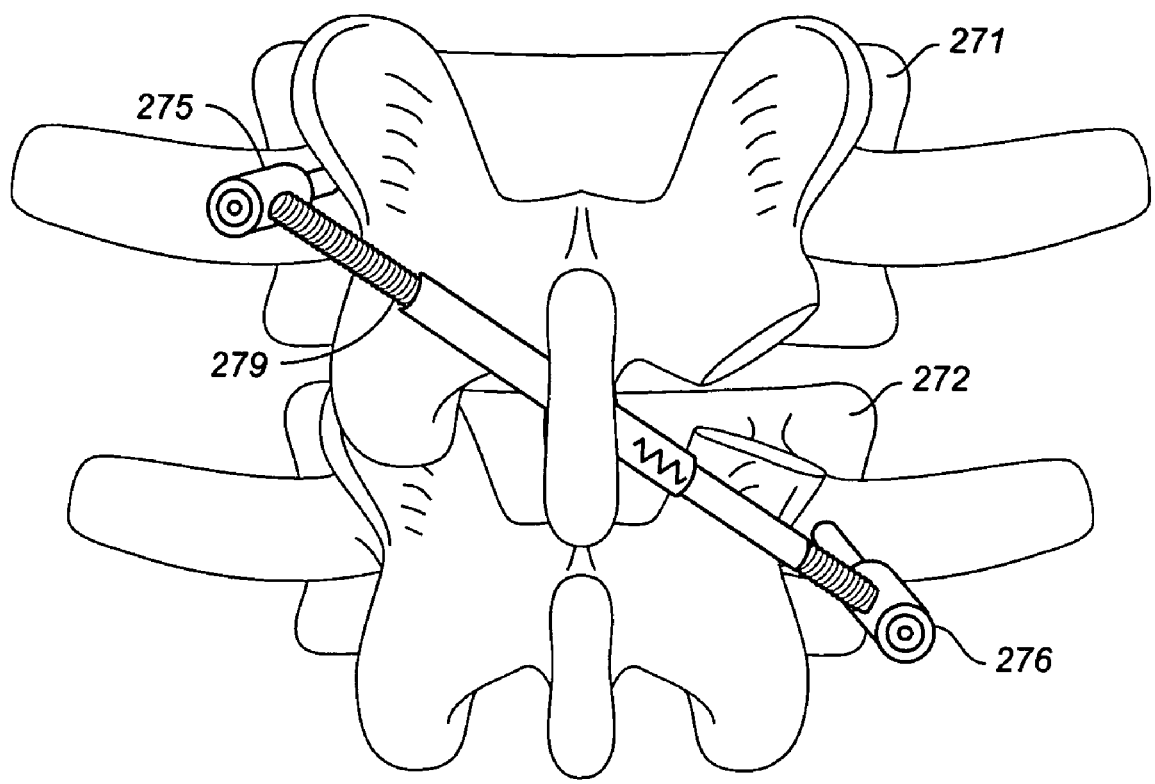
FIG. 31B is a posterior view of the implant implanted as shown in FIG. 31A.

FIGS. 31A and 31B illustrate a support prosthesis configured to provide support of the spine where a facet has been removed in whole or in part. The support prosthesis 270 comprises a support rod 279 anchored into a pedicle 273 of a first vertebra 271 through a screw head of a pedicle screw 275. The support rod 279 extends through an opening 278 in the spinous process 277 to a pedicle screw 276 anchored in contralateral pedicle 274 of a second vertebra 272. The support rod 279 is oriented at an oblique angle with respect to a median and/or horizontal plane intersecting the first vertebra, and over the region 279a from which the facet was removed. The support rod 279 may include a distraction element and/or shock absorbing properties, for example as discussed above with reference to FIGS. 16A-16F. The rod 279 at least in part supports the load that was previously borne by the removed facet joint when it was intact. The support rod 279 also provides distraction for the joint. The spinous process 277 may include reinforcement or a support structure such as described herein. The rod 279 may be constructed of a materiel that permits flexing and twisting motions, such as, e.g., a suitable polymer material. The superior part of the rod 279 may alternatively be anchored in the lamina, spinous process or attachments to the posterior elements of the vertebra. The bar 279 may also be positioned over the region 279a in a generally parallel position with respect to the rotational axis of the spine.

Figure 15A:
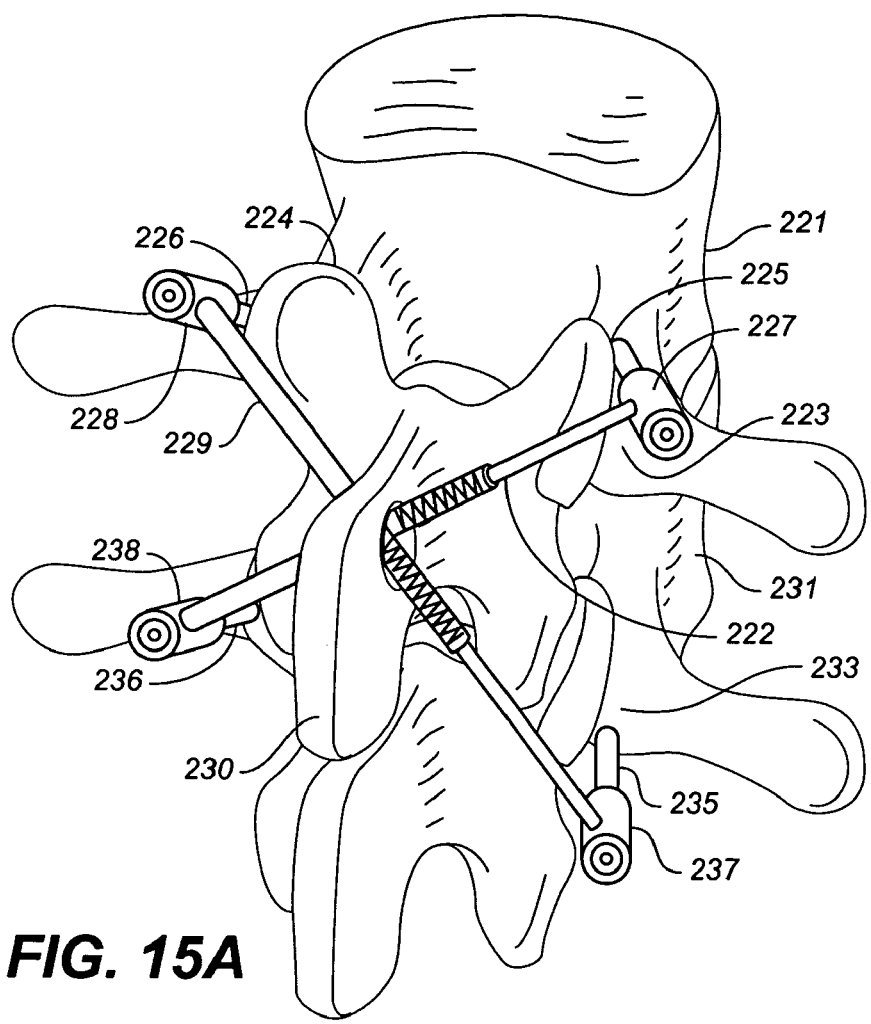
FIG. 15A is a posterior lateral perspective view of a distraction system implanted in a spine in accordance with the invention.
Figure 15B:
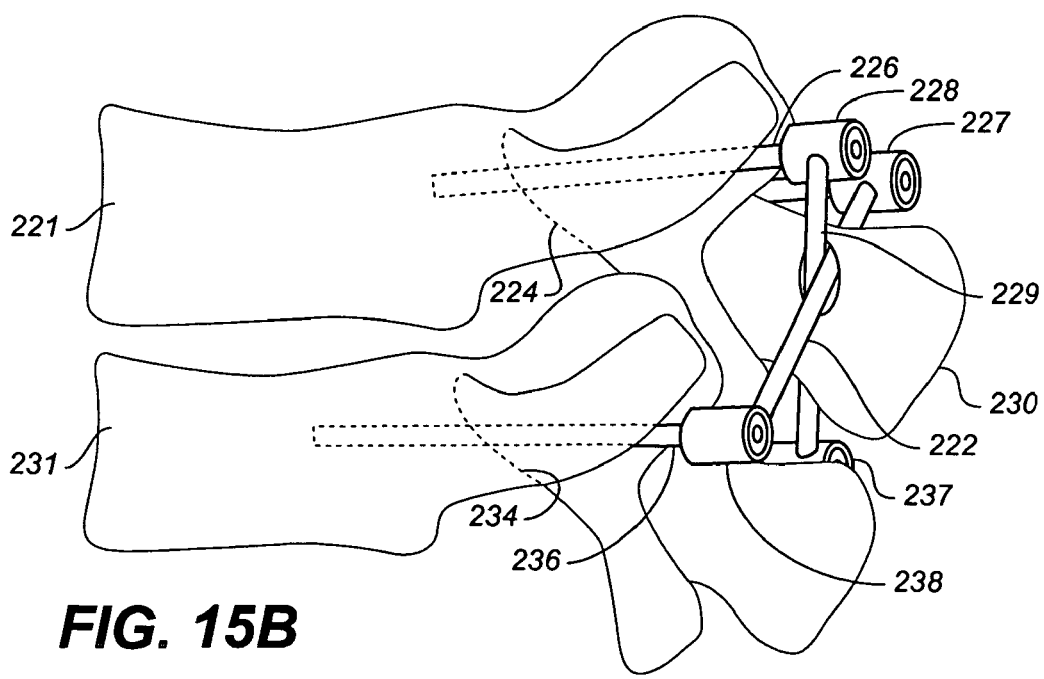
FIG. 15B is a side perspective view of the distraction system implanted in a spine as shown in FIG. 15A.
Figure 15C:
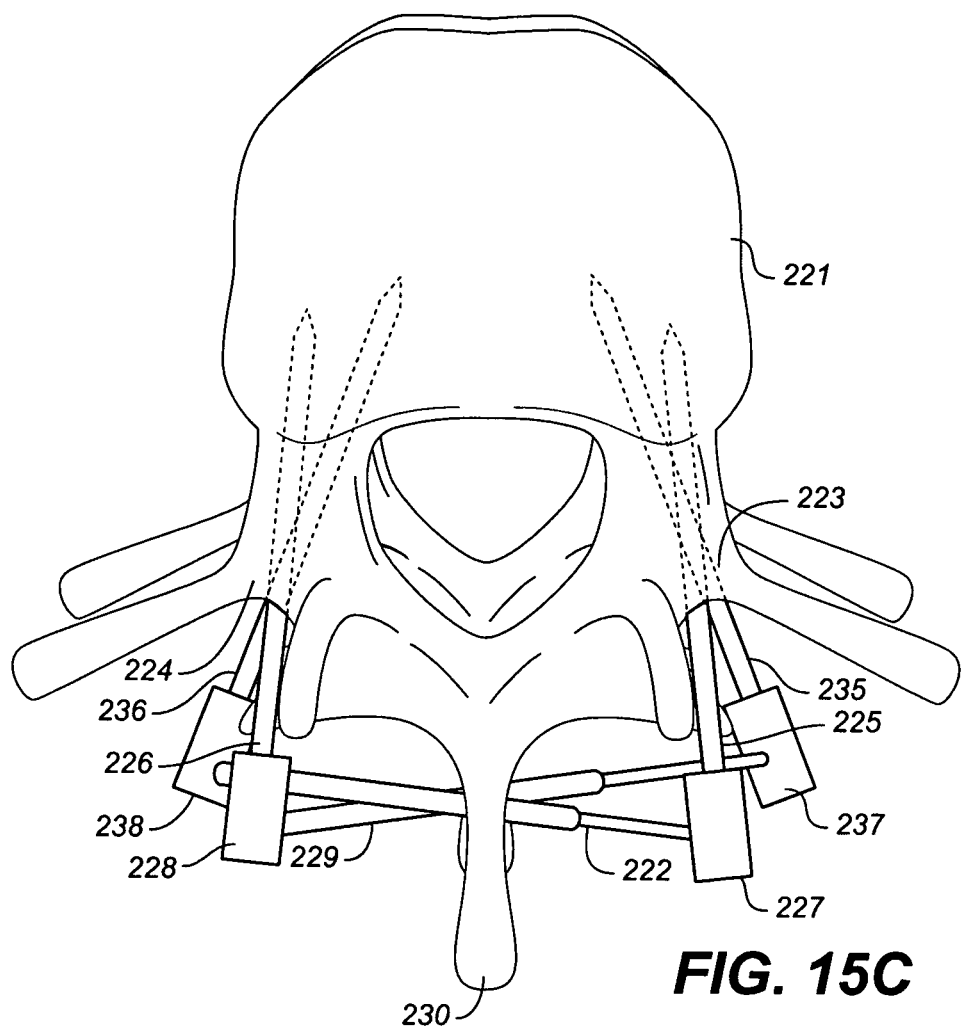
FIG. 15C is a top view of the distraction system implanted in a spine as shown in FIG. 15A.
Figure 15D:
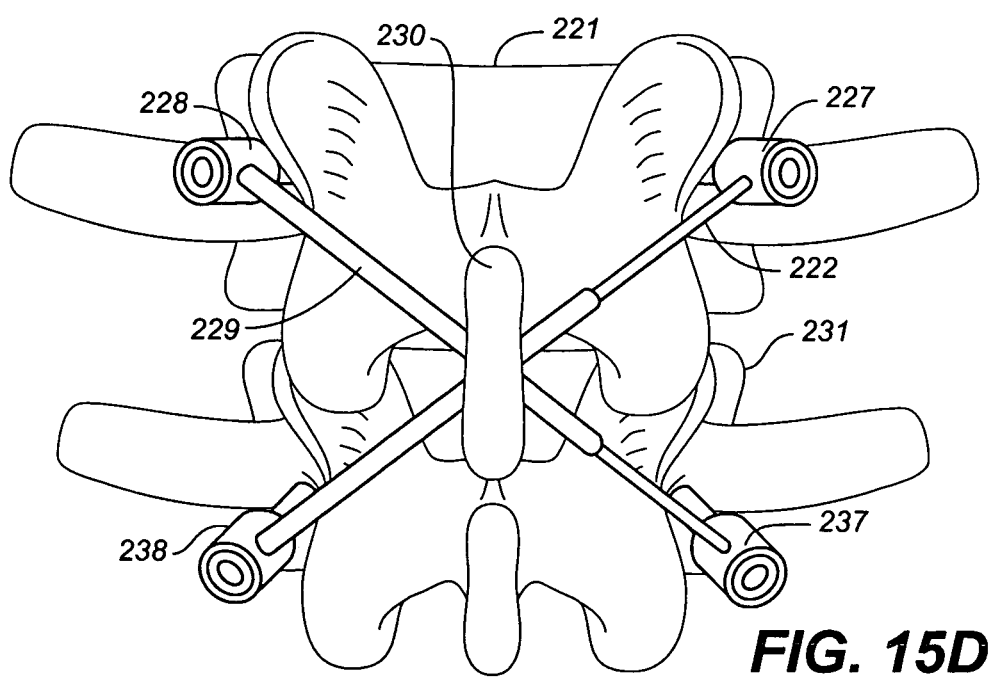
FIG. 15D is a posterior perspective view of the distraction system implanted in a spine as shown in FIG. 15A.

FIGS. 15A-15B illustrate a pedicle to pedicle positioning of a distraction system in accordance with the invention. A pedicle screw 225 is implanted in the pedicle 223 of a first vertebra 221. A pedicle screw 236 is implanted in the pedicle 234 on the contralateral side of a second vertebra 231. A distraction rod 222 is positioned between the pedicle screw 225 on the first vertebra 221 and the pedicle screw 236 on the second vertebra 231 at an oblique angle with respect to the rotational axis along the length of the spine, (or with respect to a median plane and/or a horizontal plane) between the vertebrae 221, 231. The first end of the distraction rod 222 is fixed into a head 227 of the pedicle screw 225 and the opposite end of the distraction rod 222 fixed into a head 238 of the pedicle screw 236. The distraction rod 222 passes through the spinous process 230. The distraction rod 222 includes a distraction element, for example as described above with respect to FIGS. 16A-16E. The spinous process 230 may be reinforced as described herein. Alternatively, the spinous process 230 may be removed to implant the distraction system. A similar distraction rod 229 including a distraction element is affixed on the contralateral pedicles 224, 233 respectively to pedicles 223, 234. A pedicle screw 226 is implanted in the pedicle 224 of a first vertebra 221. A pedicle screw 235 is implanted in the pedicle 233 on the contralateral side of a second vertebra 231. A distraction rod 229 is positioned between the pedicle screw 226 on the first vertebra 221 and the pedicle screw 235 on the second vertebra 231 at an oblique angle with respect to the rotational axis along the length of the spine between the vertebrae 221, 231 (or with respect to a median plane and/or a horizontal plane). The first end of the distraction rod 229 is fixed into a head 228 of the pedicle screw 226 and the opposite end of the distraction rod 229 fixed into a head 237 of the pedicle screw 235. The distraction rod 229 also passes through the spinous process. Or, the spinous process 230 may be removed to implant the distraction system. The distraction rods 222, 229 when in position operate to exert a separating force in a plurality of oblique directions (in this particular instance in opposing directions that are substantially normal with respect to one another, the oblique angle being with respect to a median and/or horizontal plane passing though a vertebra) that separate the two vertebrae 221, 231. The distraction rods 222, 229 may be attached to the pedicle screws 223, 234 and 224, 233 respectively, either before, during or after distraction occurs. Sensors may be included with the distraction rod 222 in a similar manner as distraction rod 185 herein.

Figure 19:
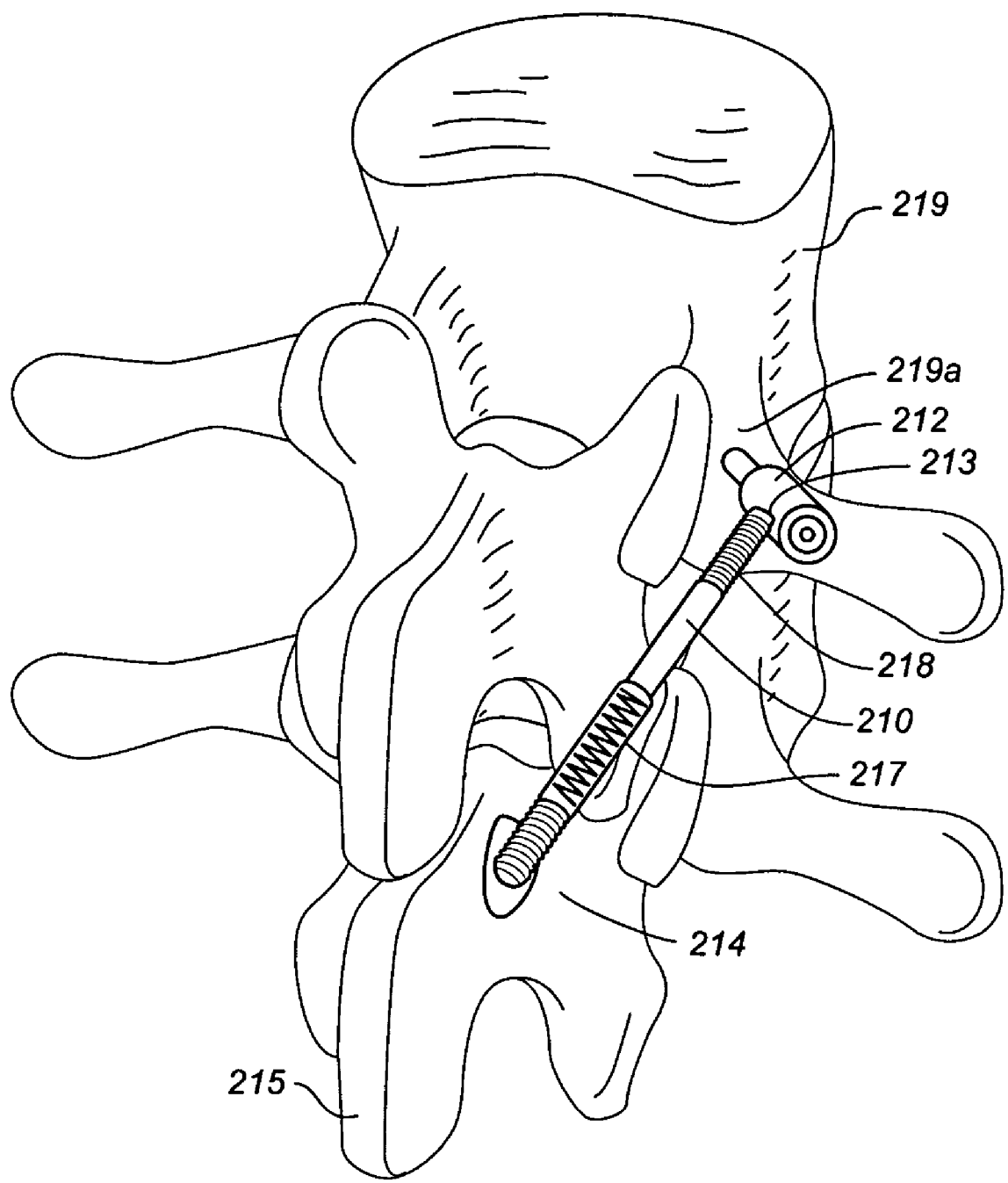
FIG. 19 is a posterior lateral perspective view of an implant implanted in accordance with the invention.

Referring to FIG. 19, a distraction system in accordance with the invention is illustrated where the distraction device is anchored to a pedicle from one level and a lamina of an adjacent level. In this particular embodiment, the distraction system is positioned from the lamina of an inferior or lower vertebra through the pedicle of a superior vertebra. The system may alternatively be positioned form the lamina of a superior vertebra through the pedicle of an inferior vertebra. The location and angle of the distraction rod may be selected depending on the desired load bearing properties of the distraction system, i.e., depending upon the anatomy the symptoms or prognosis of the patient. The distraction rod 210 may include any of the features of the various distraction rods described herein, for example, the distraction rod 210 may adjustable in length in various ways, may be adjustable by different mechanisms including remote or minimally invasively, and/or the distraction rod 210 may include shock absorbing features or locking features. The distraction system includes a pedicle screw 212 with a threaded opening 213 for receiving the distraction rod 210. The distraction rod 210 is configured to be anchored to the lamina 214 of a first vertebra 215 by a rod portion (or screw) 217 extending through the lamina 214 and having a head 216 holding the rod portion 217 on to the lamina 214. The threaded distal end 218 of the rod portion 217 extends into the threaded opening 213 of the pedicle screw 212 which is implanted in the pedicle 219a of a second vertebra 219, and thereby mechanically coupling the first and second vertebrae 215, 219. The distraction rod 210 is implanted so that there is an oblique exertional force between the lamina 214 of the first vertebra 215 and the pedicle 219a of the second vertebra 219. The lamina 214 may be reinforced in a manner as described herein. The distraction rod 210 may accordingly be positioned through a reinforced lamina as described herein. A second distraction rod (not shown) is positioned on the contralateral side of the lamina 214 and through the contralateral pedicle of the second vertebra 219. The distraction rod 210 is positioned at an oblique angle such that it relieves load from the facet joint between the vertebrae 215, 219.

Figure 22:
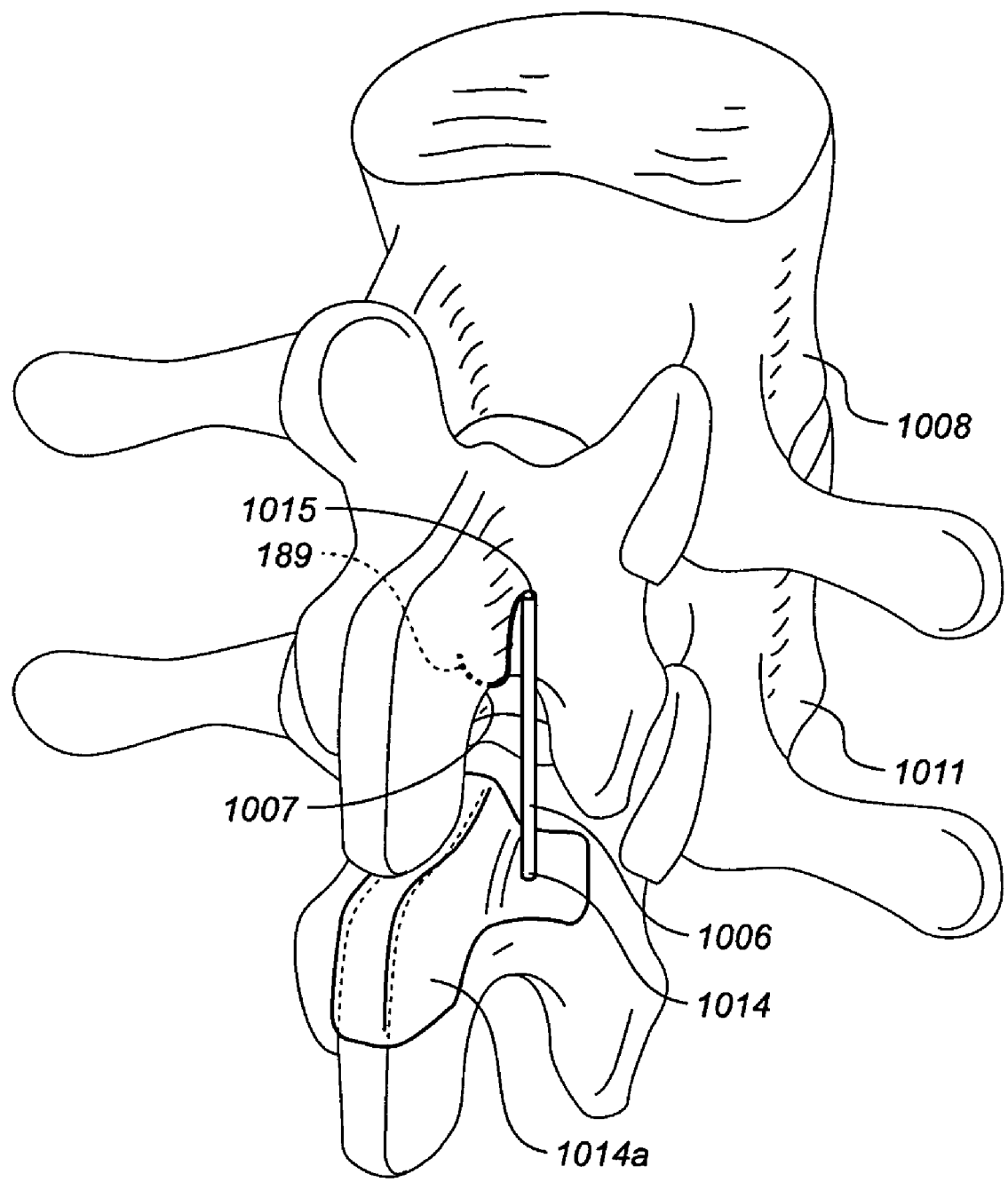
FIG. 22 is a posterior lateral perspective view of an implant in accordance with the invention.

FIG. 22 illustrates a spinal distraction system with a distracting rod 1006 anchored at one end (the cephalic end 1015) to the inferior lip 1007 of a superior vertebra 1008 via a hook 1009, and anchored at the other end (the caudal end) 1014 to hood 1014a configured to secure the rod 1006 to the lamina 1010 of an inferior vertebra 1011.

FIGS. 20A-20I illustrate a spinal distraction system 440 and method of implanting in accordance with the invention. The system 440 comprises pedicle screws 441, 442, fixed to contralateral pedicles 443,444 of a first vertebra 449 and pedicle screws 445, 446 fixed to contralateral pedicles 447, 448 of a second vertebra 450. The system further comprises removable pedicle screw extenders 451, 452, 455, 456 with threaded connector ends. Each of the pedicle screws 441, 442, 445, 446 comprise threaded screw heads 441a, 442a, 445a, 446a configured to receive threaded heads of the pedicle screw extenders 451, 452, 454, 456, respectively. In use, the pedicle screw extenders 451, 452, 455, 456 are coupled to the pedicle screws 441, 442, 445, 446 by way of threaded screw heads 441a, 442a, 445a, 446a. The pedicle screw extenders 451, 452, 455, 456 extend from the pedicle screws 441, 442, 445, 446 at the spine to position just at or outside of the subcutaneous tissue. The pedicle screw extenders 451, and 455, and pedicle screw extenders 452 and 456, are respectively separated from each other to distract the joint motion segments between the first vertebra 449 and the second vertebra 450. This may be done while the patient is awake and standing. The provider may manipulate the screw extenders until the patient reports relief from the pain e.g. of spinal stenosis. Distraction bars 457, 458 are respectively positioned between and coupled to pedicle screw extenders 451, and 455, and pedicle screw extenders 452 and 456 to maintain distraction as described herein with reference to FIG. 20B-20J. The pedicle screw extenders 451, 452, 455, 456 may be unscrewed and removed. A wire may extend from each for the pedicle screws 441, 442, 445, 446 through a lumen in the pedicle screw extenders 451, 452, 455, 456 so that when they are unscrewed and removed, a wire remains in place. If additional adjustment is necessary, the wires may act as guidewires guiding the pedicle screw extenders 451, 452, 455, 456 to the respective pedicles 441, 442, 445, 446 to adjust the distraction level.

Figure 20A:
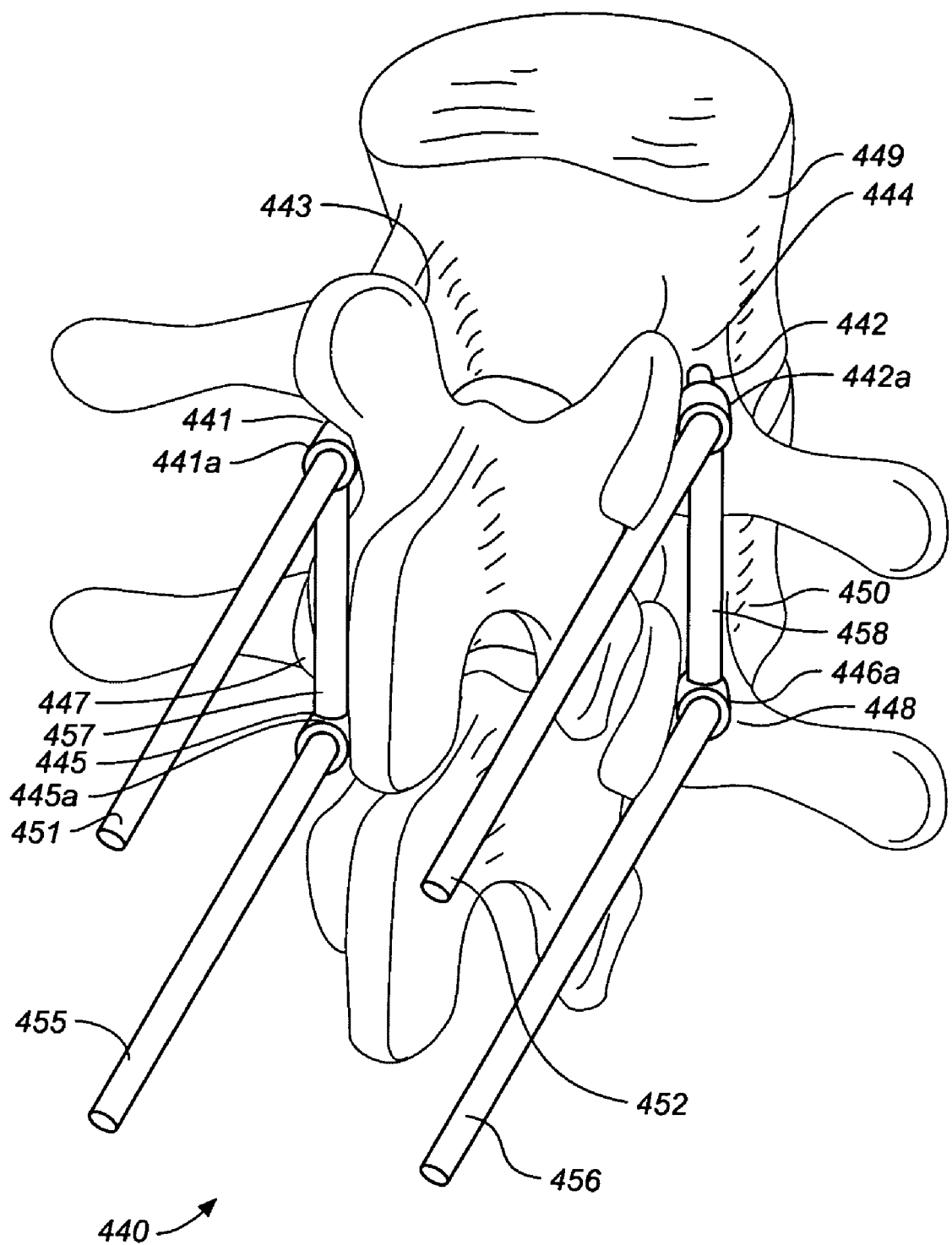
FIG. 20A is a posterior lateral view of a distraction system in accordance with the invention.
Figure 20B:
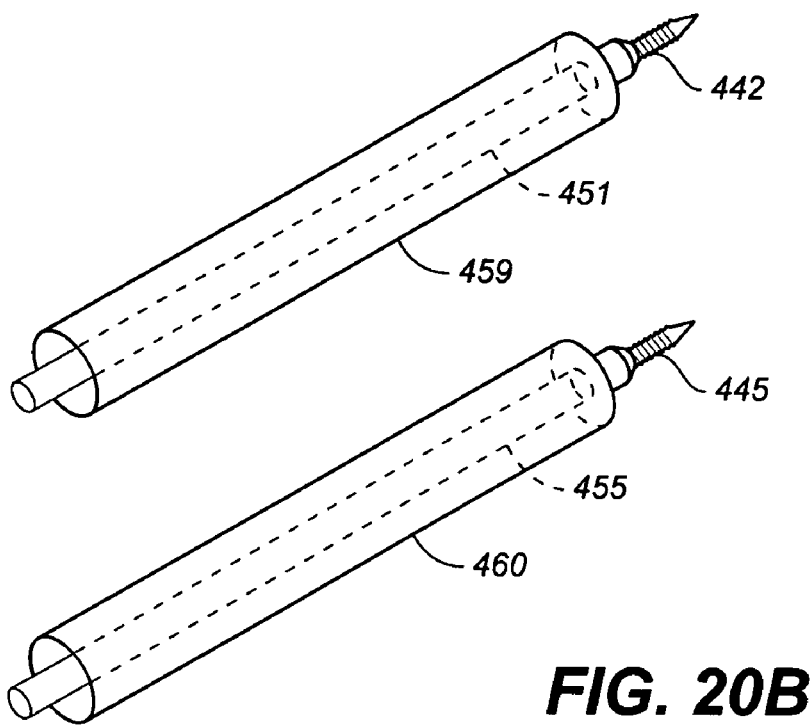
FIGS. 20B-20I are a schematic illustration of a method of implanting the distraction system of FIG. 20A.
Figure 20C:
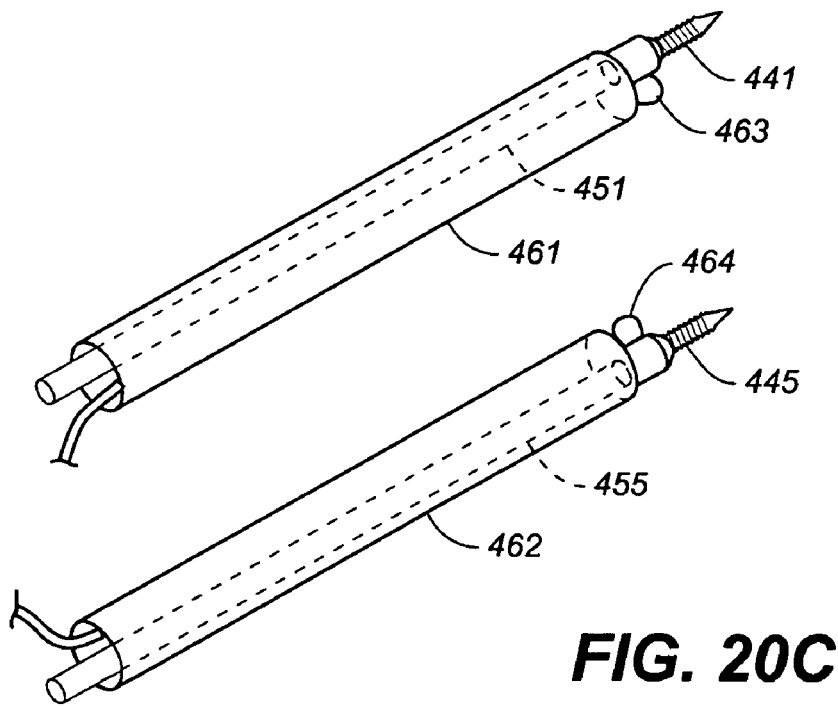
Figure 20D:
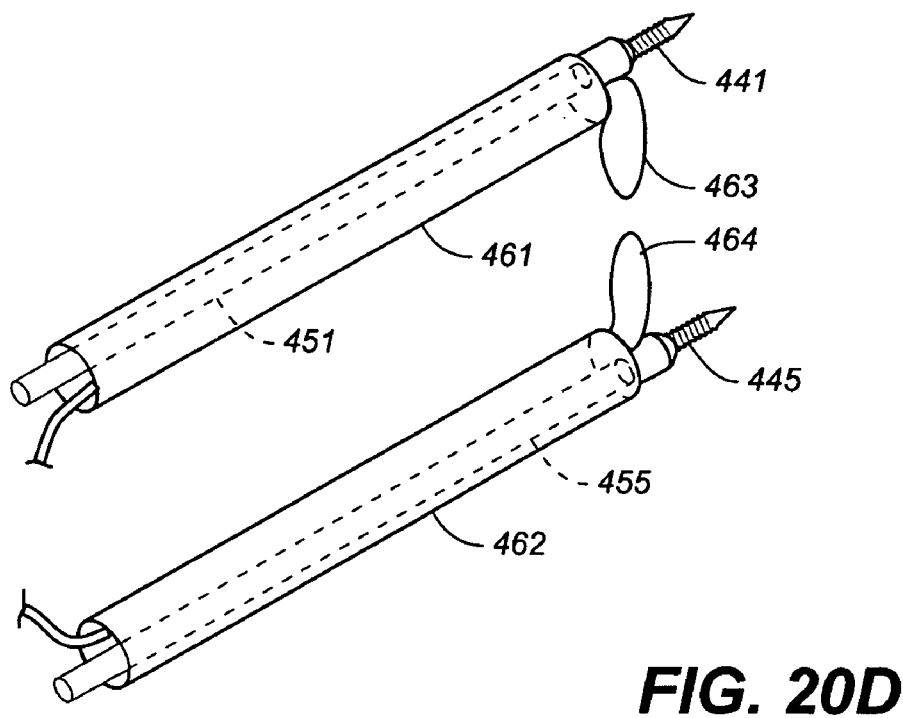
Figure 20E:
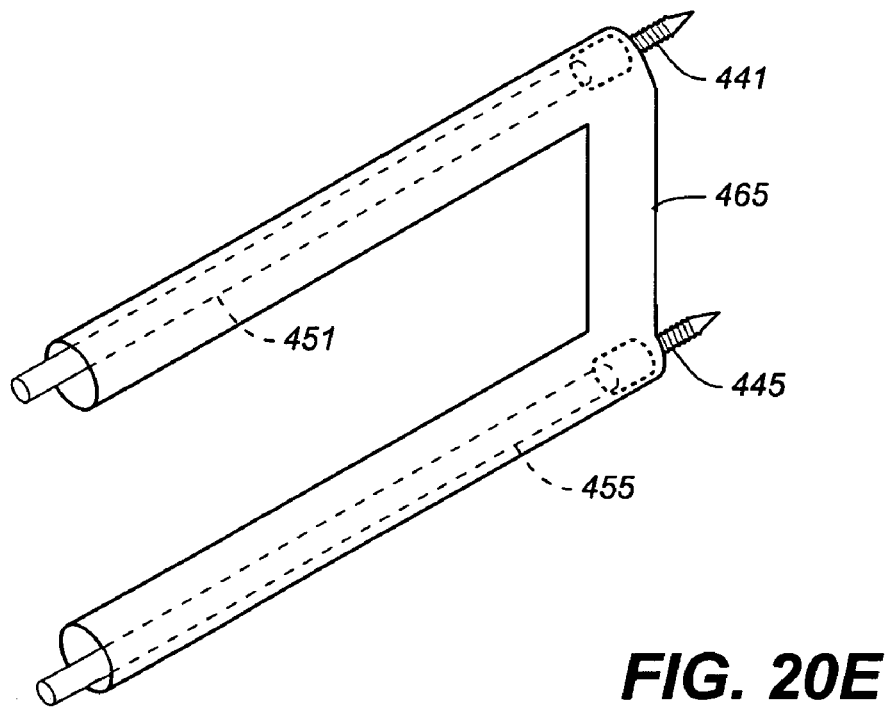
Figure 20F:
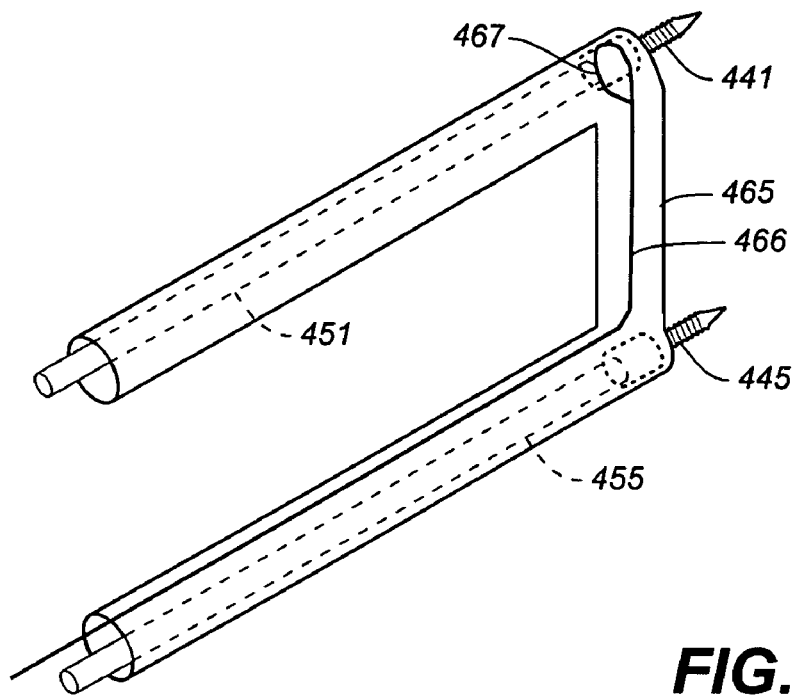
Figure 20G:
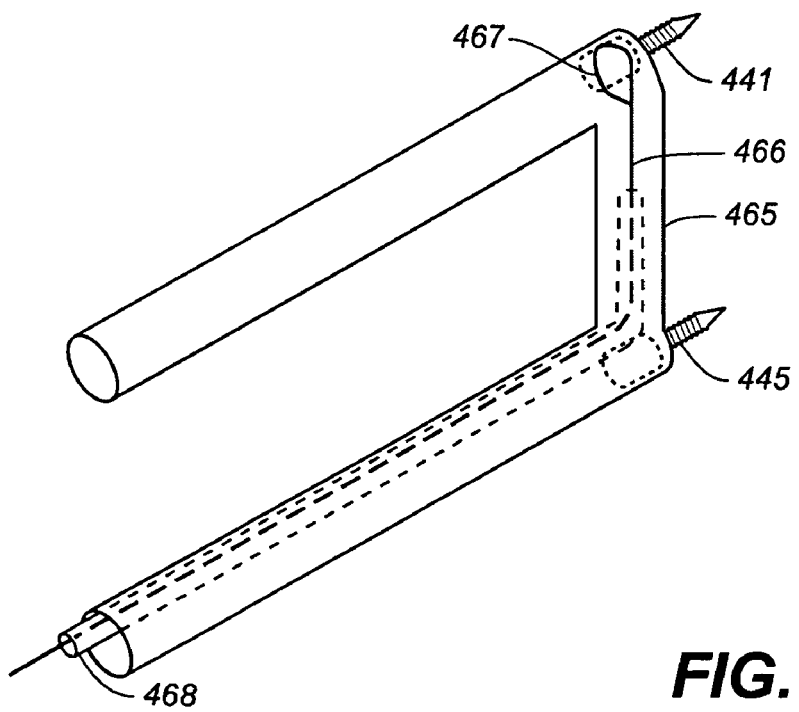

Referring to FIGS. 20B-20J a method of placing distraction bars 457, 458 is illustrated. With screw extenders 451, 455 in place, dilators 459, 460 are placed over the screw extenders 451, 455 to create an access channel to the pedicle screws 441, 445. (FIG. 20B) The dilators 459, 460 are then removed and balloon catheters 461, 462 are inserted over the extenders 451, 455. (FIG. 20C) The balloon catheters 461, 462 each have a lumen therethrough for receiving the extenders 451, 455, and inflatable balloons 463, 464 on one side of each of the catheters 461, 462 so that when the balloons are position opposite each other, they may be inflated to form contiguous canal when they meet each other (FIG. 20D). The extenders 451, 455 and balloon catheters 461, 462 may be keyed so that the balloon catheters are appropriately aligned with the balloons 463, 464 facing each other so that a contiguous passageway may be formed. The balloons 463, 464 are deflated and the balloon catheters 461, 462 are removed leaving a tunneled region 465 between the pedicle screws 441, 445. (FIG. 20E).

Figure 20H:
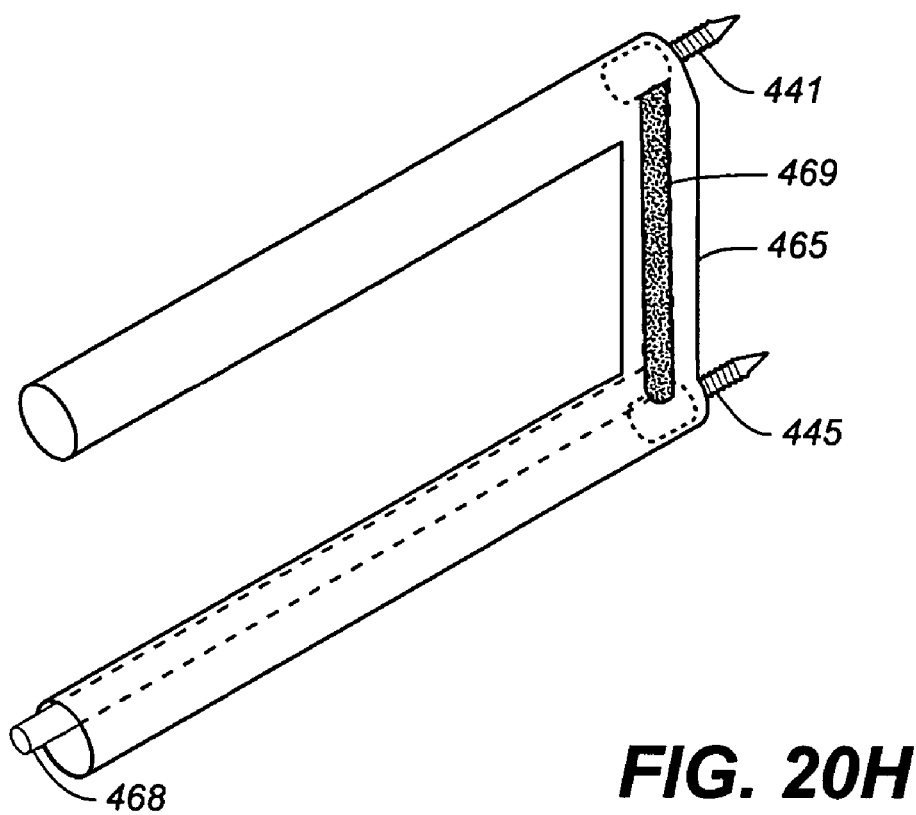
Figure 20:
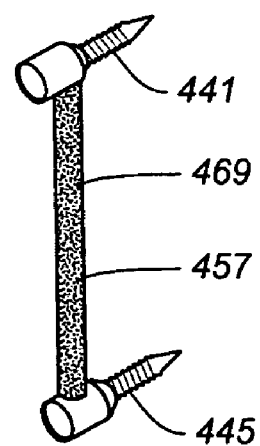

A guidewire 466 having a wire loop 467 at the end is introduced through the channel adjacent the extender 455 and is directed through the tunneled region 465 where the loop 467 is used to capture the threaded head 441a of the pedicle screw 441. (FIG. 20F) Various imaging techniques such as fluoroscopic imaging may be used to guide the loop 467 to the proper location at the head 441a of the pedicle screw 441. A flexible tube 468 is guided over the guide wire (FIG. 20G) to a position through the tunneled region 465 and to the pedicle screw 441 (FIG. 20H). The guidewire 466 is removed and a curable polymer 469 is injected through flexible tube 468 preferably using a flexible needle that can be positioned at the end of the flexible tube 468 where it sits in the tunneled region 465. (FIG. 20I) The polymer cures and the portion of the tube that is not in the tunneled region is cut away and removed, leaving a hardened tube between the pedicles that holds the pedicle screws 441, 445 in a distracted position with respect to each other. Alternatively, a device such as the Sexant™ device manufactured by Medtronic, Inc. may be used to create a tunnel between adjacent pedicle screws and to connect them with a curved rod.

Figure 21:
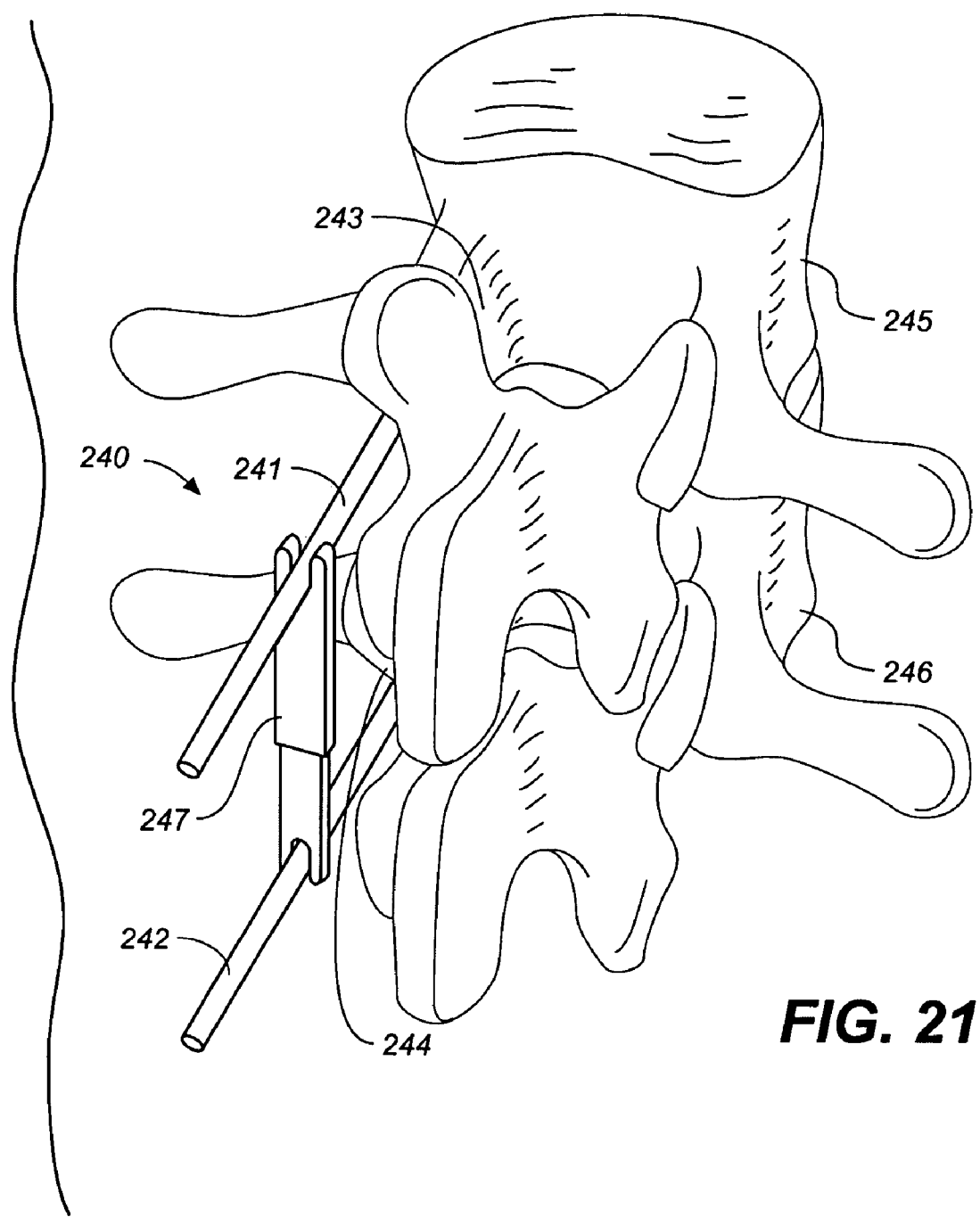
FIG. 21 is a posterior lateral view of a distraction system in accordance with the invention.

FIG. 21 illustrates an internal fixator for distraction of a motion segment of a spine. The fixator 240 comprises rods 241, 242 placed percutaneously through the skin and muscle to the pedicles 243, 244 of adjacent spinal vertebrae 245, 246 where they are screwed in, or otherwise secured to the pedicles, e.g. via multi-axial pedicle screws. The rods 241, 242 are spread apart to distract the adjacent spinal vertebrae 245, 246 from each other to relieve pressure on the spine and associated tissue at the motion segment between the vertebrae 245, 246. A subcutaneous securing element 247 is placed between the rods 241, 242 in a subcutaneous location between the skin and the muscles, to secure the rods 221, 222 in the distracted position. After positioned, the device may be distracted, e.g. at a physician's office while patient provides feedback to the provider concerning pain or discomfort. This would allow for just enough distraction to relieve symptoms of stenosis, while avoiding unnecessary over-distraction. The securing element 247 may be selected from a plurality of securing elements of different lengths or may itself be distracted. The appropriate length may be selected depending on the amount of distraction of the device. The securing device may replaced at a later time when, for example, further distraction is needed.

Figure 14A:
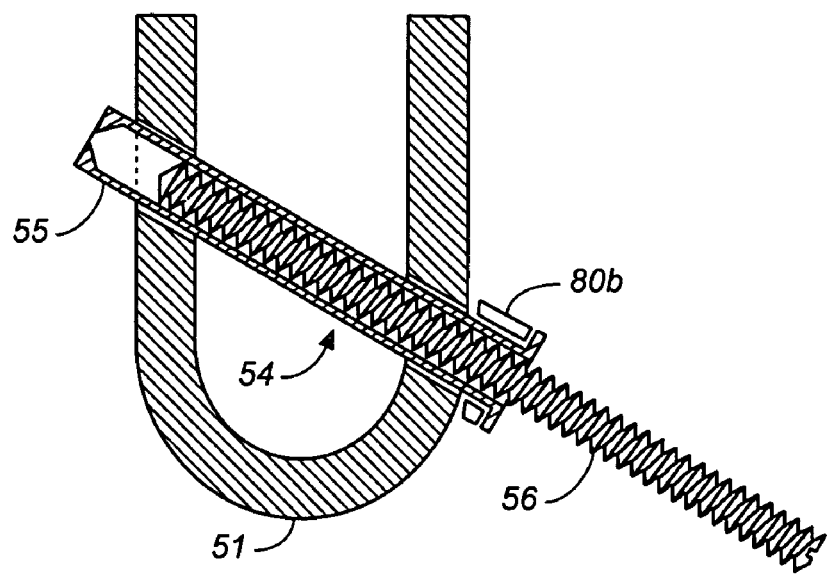
FIG. 14A is a schematic partial cross sectional view of an implant in accordance with the invention in a first position.
Figure 14B:
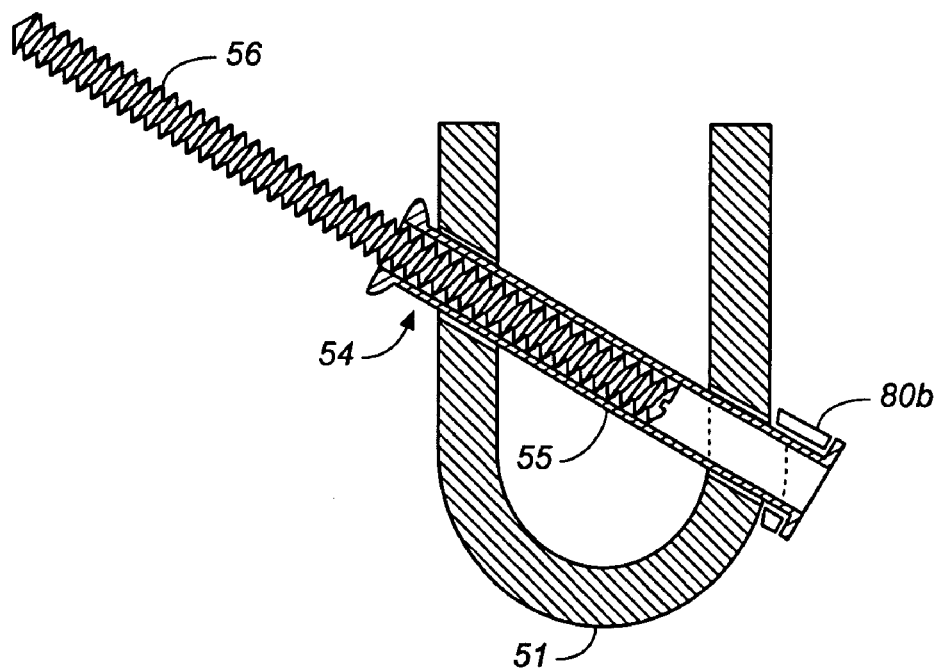
FIG. 14B is a schematic partial cross sectional view of the implant of FIG. 14A in a second position.

FIGS. 14A and 14B illustrate a spinous process rod or screw 54 in accordance with the invention. The spinous process rod or screw 54 comprises an elongate outer tube portion 55 and an inner rod portion 56. The inner rod portion 56 is configured to move longitudinally within the tube portion 55 to lengthen or shorten the spinous process screw or rod 54. The inner wall of the tube portion 55 may include a threaded inner wall that mates with a threaded outer wall of the rod 54 so that the rod may be screwed to advance the rod 56 and thereby lengthen or shorten the spinous process screw or rod 54. Once the outer rod 55 and screw 56 are positioned within a spinous process or hood 51 the spinous process screw or rod 54 may then be lengthened as shown in FIG. 14B to extend through the reinforcement hood 51. The lengthened spinous process screw may be used to distract the spinal segment or segments as well.

The pedicle attachment devices herein may include a sensor that may be used to sensor one or more parameters e.g., strain, pressure, motion, position change, that provides information about possible screw failure. The sensor may communicate the information to an external device, e.g. telemetrically, and may be passively powered by an external device.

According to another aspect of the invention a rod is provided that is anchored to with pedicle screws with screw heads made of or attached to swivel collars, polyaxial heads, or other movable fasteners to allow for near physiologic levels of motion of the spinal motion segment. Angular movement may be provided where a distracting element attaches on either side of a motion segment so that when distracting or lengthening the device, there is accommodation in the device for the change of angle that occurs.

Figure 32:
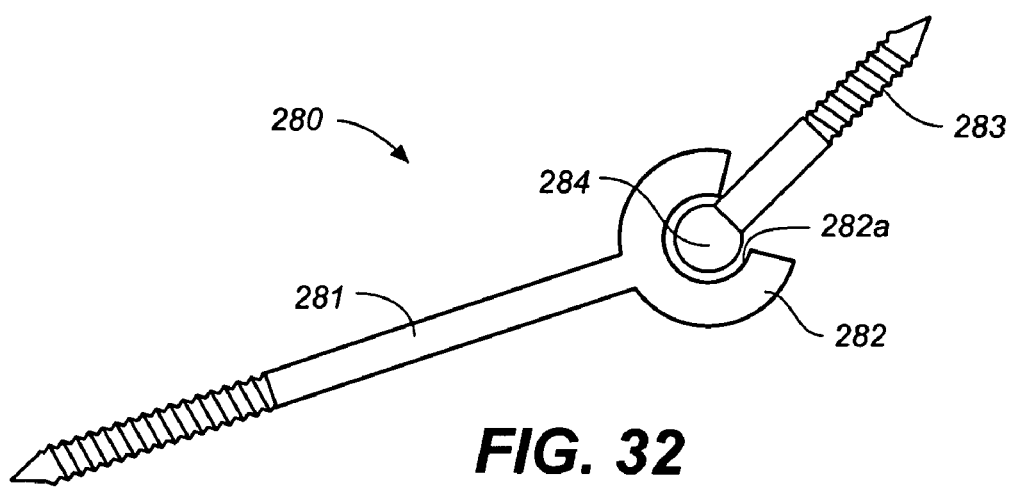
FIG. 32 is a schematic side view of a connector of an implant in accordance with the invention.

FIG. 32 illustrates an enlarged portion of a spinal prosthesis. The prosthesis 280 may provide support of the load on the spine where a facet has been removed or may provide other support or distraction. The prosthesis 280 comprises a distraction bar 281 used to distract a motion segment of the spine in a number of manners including the distraction devices described herein. A pedicle screw 283 is screwed into a pedicle of the spine or other anatomical location. The distraction bar 281 includes and articulating cup 282 having an inner surface 282a. The pedicle screw 283 has a ball 284 received by and coupled to the cup 282 of the distraction bar 281. In addition to shock absorbing capabilities described in various embodiments herein, the distraction bar 281 also articulates with a portion of the spine to which the pedicle screw 283 is attached.

Figure 33:
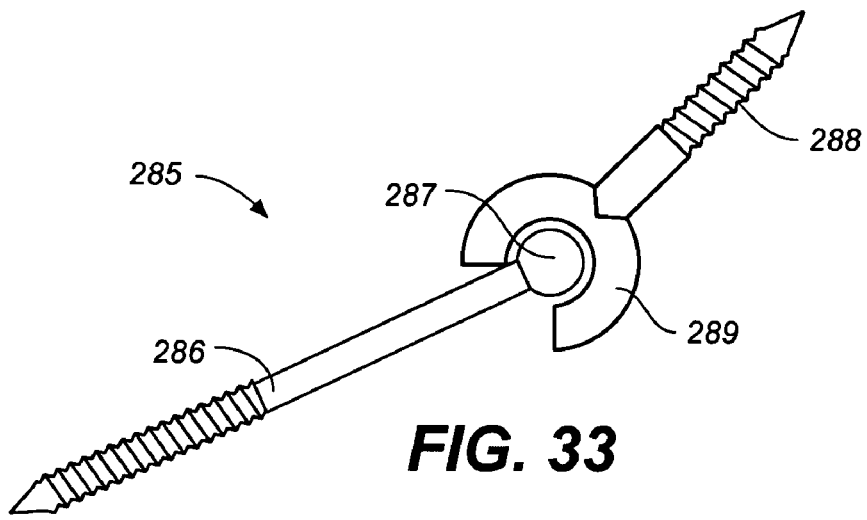
FIG. 33 is a schematic side view of a connector of an implant in accordance with the invention.

FIG. 33 illustrates a variation of the prosthesis 280 described with respect to FIG. 32. The prosthesis 285 comprises a distraction bar 286 and an articulating ball 287 configured to engage and couple with an articulation cup 289 of a pedicle screw 288. The prosthesis 285 operates in a similar manner as prosthesis 280.

Figure 34:
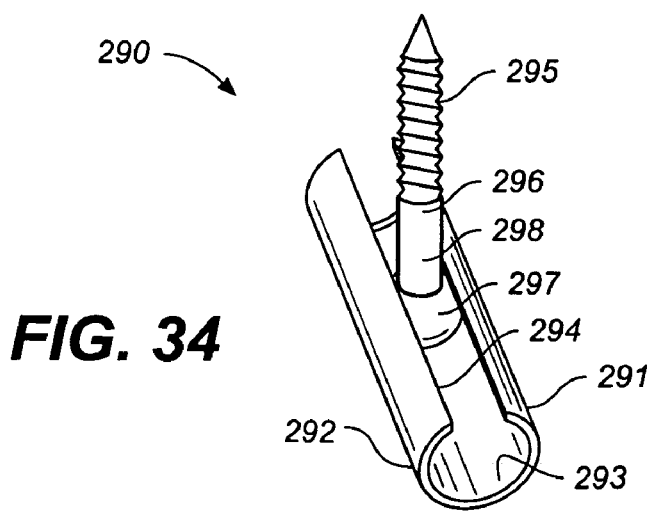
FIG. 34 is a schematic perspective view of a connector in accordance with the invention.
Figure 35:
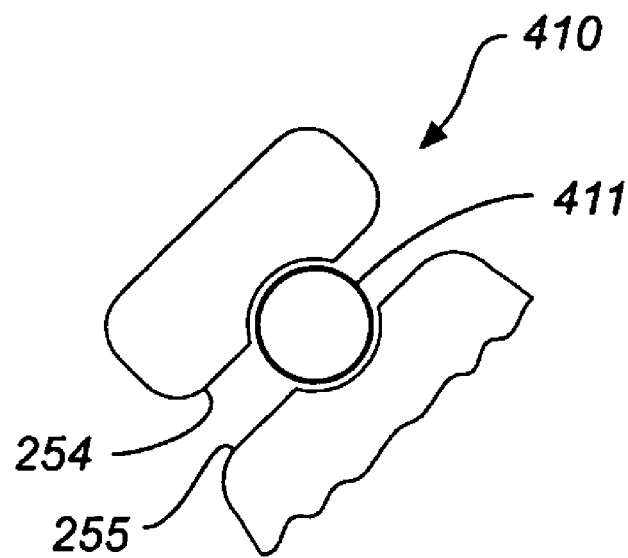
FIG. 35 is a schematic side view of a facet implant in accordance with the invention.

FIG. 34 illustrates a variation of the prostheses 280, 285 described herein respectively with respect to FIGS. 33 and 32. The prosthesis 290 comprises a distraction bar 291 having an end 292 with a lumen 293 for slidably receiving the end 296 of a pedicle screw 295. The end 296 of the pedicle screw 295 comprises a ball portion 297 attached to a neck 298. The ball 297 portion is configured to slide within the lumen 293 of the distraction bar 291 which contains the ball portion 297. The neck 298 of the pedicle screw 295 extends out of the distraction bar 291 through a longitudinal slit 294 that slidably receives the narrower neck portion 298 of the pedicle screw 295.

One embodiment of the invention is a rod anchored at each end across a motion segment that can be "switched" between dynamic stabilization and rigid fixation in a minimally invasive, percutaneous, or non-invasive fashion. One way for this to occur is injection of a flowable material within the lumen of the device, which would cure, and immobilize the components which allow for motion. Electrical current, heat, mechanical energy, or other techniques could also be used to render movable components fixed. Another method is insertion of a rigid implant axially along the length of the dynamic implant. This method of rendering a flexible prosthesis rigid may be applied to the design of other combination motion/fixation prostheses, including disc, facet hip, knee, fingers shoulder, elbows, and ankle prostheses, etc.

Figure 40:
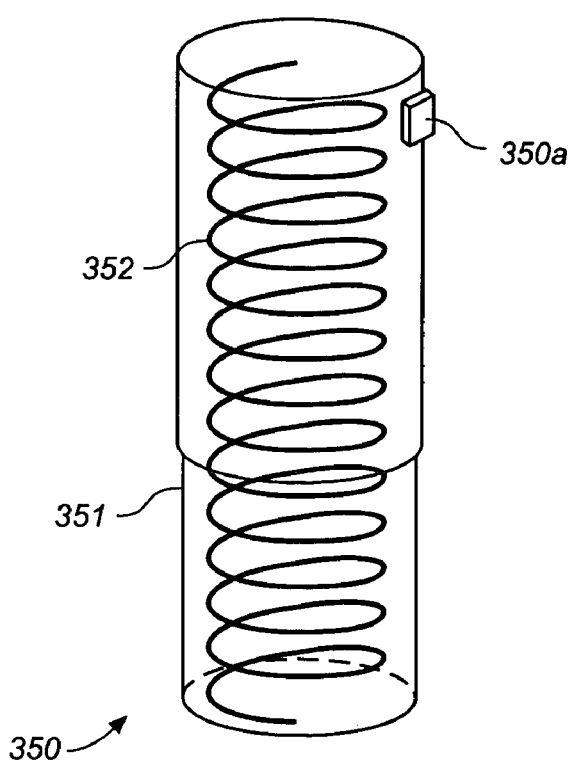
FIG. 40 is a schematic side perspective view of a dynamic element in accordance with the invention.
Figure 41:
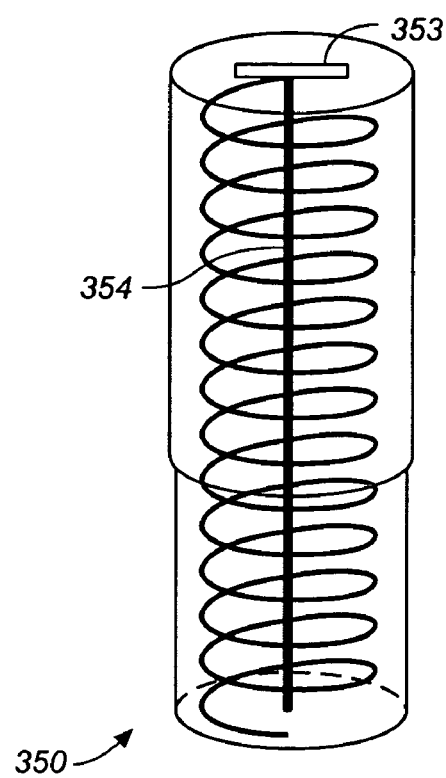
FIG. 41 is a schematic side perspective view of an adjustable implant element in accordance with the invention.

FIGS. 40-43 illustrate convertible or adjustable dynamic stabilization devices for joints. The stiffness or flexibility of the device may be altered or titrated after implantation to adapt the stiffness to a particular patient, and/or to adjust the stiffness over time, for example when laxity of the joint increases with age. Referring to FIG. 40 illustrates a dynamic stabilization prosthesis 350. The prosthesis comprises a flexible coil 352 contained in a tube member 351 comprising telescoping tubes. The prosthesis 350 may be used in a number of manners affixed across a joint motion segment to dynamically stabilize the joint. The coil 352 may be energy absorbing. The coil 352 may also be configured to exert a distracting force on the joint when implanted. FIG. 41 illustrates the dynamic stabilization prosthesis 350 of FIG. 40 converted to a rigid or more rigid prosthesis. The prosthesis 350 includes a slit 353 for receiving a rigid wire member 354. In FIG. 41 the rigid wire member 354 is inserted into the slit 353 to form the prosthesis from a dynamic prosthesis into a rigid prosthesis. As an alternative to a rigid wire member, a flexible coil of a selected stiffness may be inserted to change the stiffness of the dynamic prosthesis. The tube may alternatively comprise a ferromagnetic material contained therein and an electromagnetic field is applied that causes the prosthesis to become stiffer. The field may be varied to provide a variety of gradients in stiffness. The device may also include a sensor that operates as sensor 170a described herein. Feedback may be provided and the stiffness of the prosthesis adjusted accordingly. The stiffness may be varied when implanted using patient feedback so that the implant is more or less flexible depending upon an individual patient's needs. In addition the stiffness may be changed at different times during the course of the implants lifetime. For example, the stiffness may be increased when an increased amount of stabilization is required.

Figure 42:
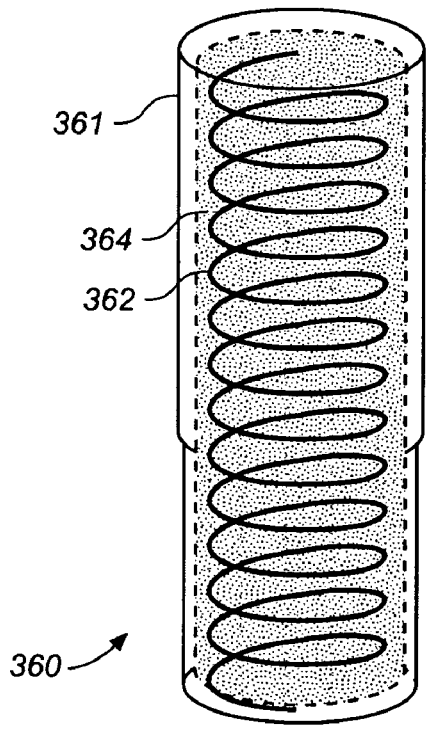
FIG. 42 is a schematic side perspective view of an adjustable implant element in accordance with the invention.

FIG. 42 illustrates an alternative prosthesis 360 also comprising a flexible coil 362 contained in a tube member 361. The tube member is configured to receive a fluid material such as a curable polymer 364 that cures in the tubular member to create a rigid prosthesis. As illustrated in FIG. 42 a rigid prosthesis is formed from a dynamic prosthesis by injecting the polymer material 364 into the tubular member 361. The flexibility/stiffness properties of the prosthesis may be selected by selecting such properties of the polymer to be injected.

Figure 43:
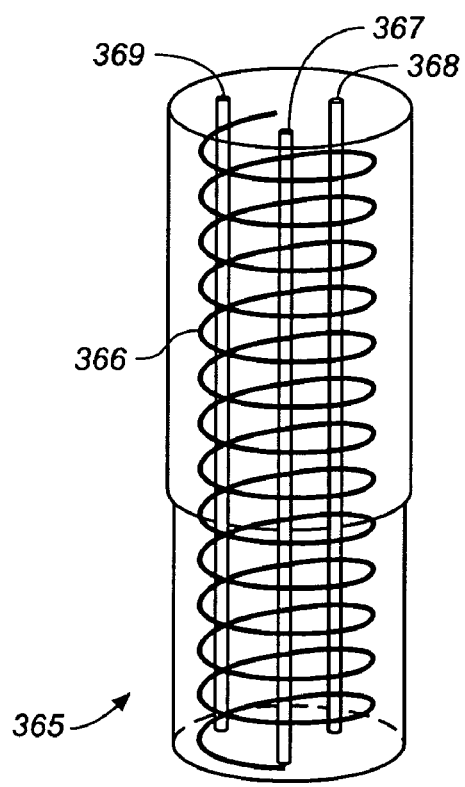
FIG. 43 is a schematic side perspective view of an adjustable implant element in accordance with the invention.

As illustrated in FIG. 43 a flexible prosthesis 365 is illustrated. The flexibility of the prosthesis 365 is adjustable by injecting a polymer material into one or more of the columnar cavities 367, 368, 369. The polymer may be injected into each cavity at a different time so the stiffness of the prosthesis may be increased gradually over time. The stiffness/flexibility properties of the polymer injected may also be selected according to a desired stiffness/flexibility of the implant.

According to an embodiment of the invention, the dynamic stabilizer may comprise a shock absorber that has both energy absorbing and energy dissipating properties. The tension band effect of the posterior columns may also offload the pressures borne by anterior column of the spine. So in addition to helping to protect the facet joints, other aspects of the invention would help slow the progression of degenerative disc disease, annular degradation, disc herniation, and vertebral compression fractures.

FIGS. 35-39 illustrate facet repair prostheses in accordance with an embodiment of the invention. Prosthesis 410 comprises a ball bearing 411 implanted between the caudal and the cephalic facets 412, 413 of the zygapopyhseal joint 414. (FIG. 35) The joint 414 is prepared by removing soft tissue between the joints and creating a concavity on adjacent facet plates for receiving the ball bearing.

Figure 36:
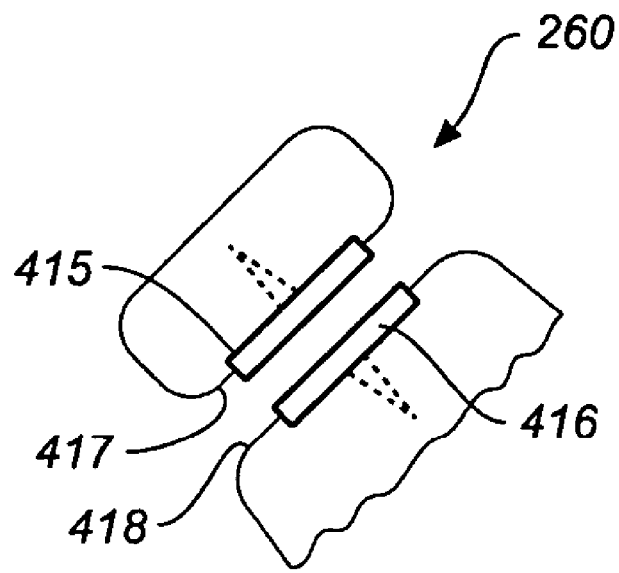
FIG. 36 is a schematic side view of a facet implant in accordance with the invention.

In FIG. 36, magnets 415, 416 including smooth interacting bearing surfaces are respectively screwed into the cephalic and caudal facets 417, 418 of the zygapopyhseal joint 419. The magnets 415, 416 are oriented so that like poles face each other (e.g. North-North or South-South) to provide a distraction force at the joint. The magnets may have a center hole through which a rod is inserted to resist the tendency of one magnet to move relative to the other. Each end of the rod may have a diameter larger than the center holes. This system may be used in other joints in the body to maintain separation between the joints.

Figure 37:
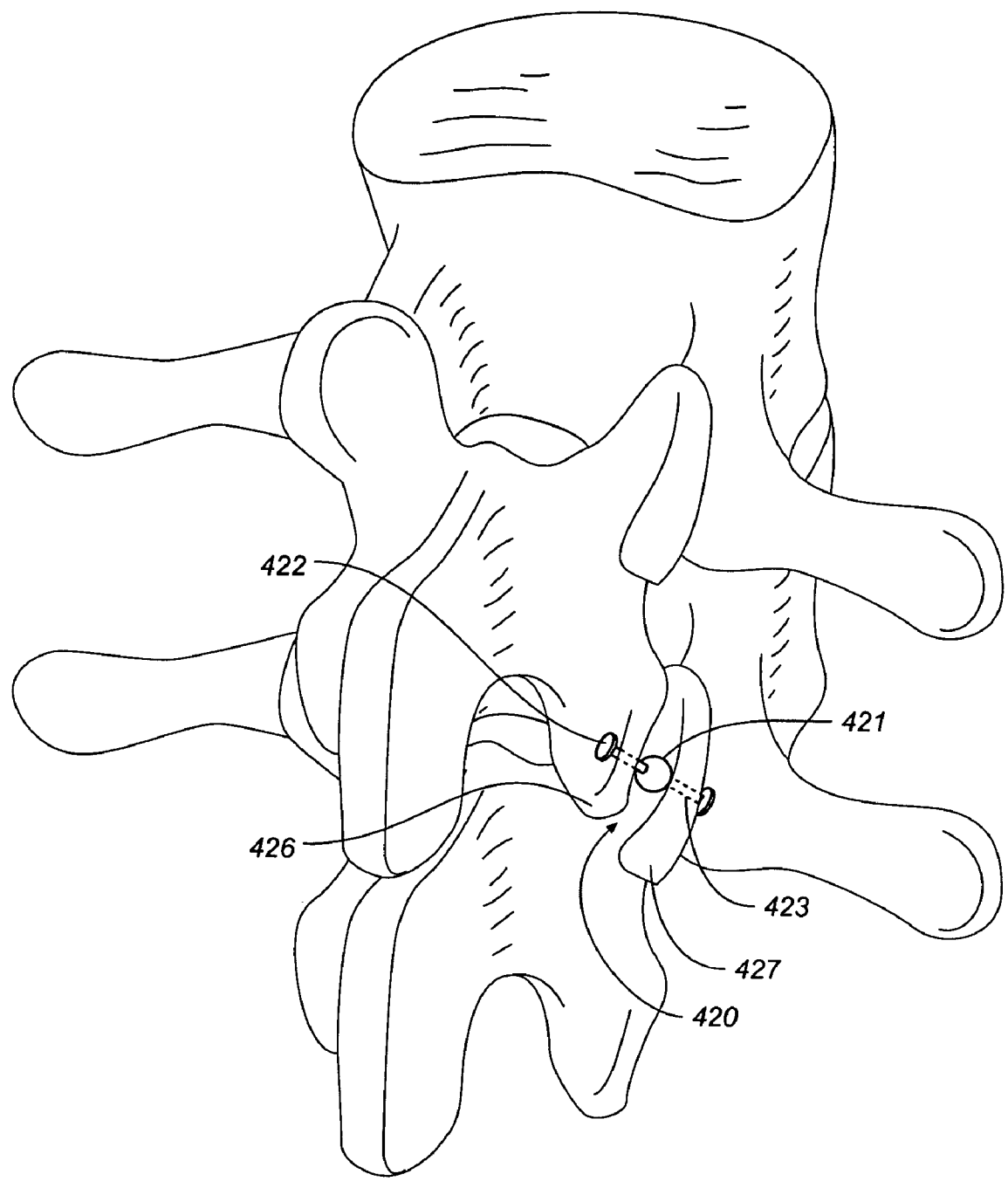
FIG. 37 is a schematic posterior lateral perspective view of a facet implant in accordance with the invention.

Referring to FIG. 37, a joint prosthesis 420 is positioned between the cephalic and caudal facets 426, 427. The prosthesis comprises a ball 421 providing a bearing surface for the motion of the facets 426, 427, and opposing posts 422, 423 screwed in or otherwise implanted in the facets 426, 427, respectively for securing the ball 421 within the joint 428. The ball 421 may include openings for receiving the posts, e.g., in a tapered interference type fitting, to secure the posts 422, 423 to the ball 421 and to secure the ball 421 within the joint 428.

This facet repair may be performed percutaneously or via minimally invasive surgical techniques, for example using percutaneously positioned distracting instruments to distract the joint, for example, an expanding balloon or forceps like distractors. Using a hollow needle percutaneously positioned into the joint, an expandable or self-expanding facet distraction implant may be placed in position through the hollow lumen of the needle into the joint. A polymer material may be injected into the joint through a percutaneously inserted needle.

Figure 38:
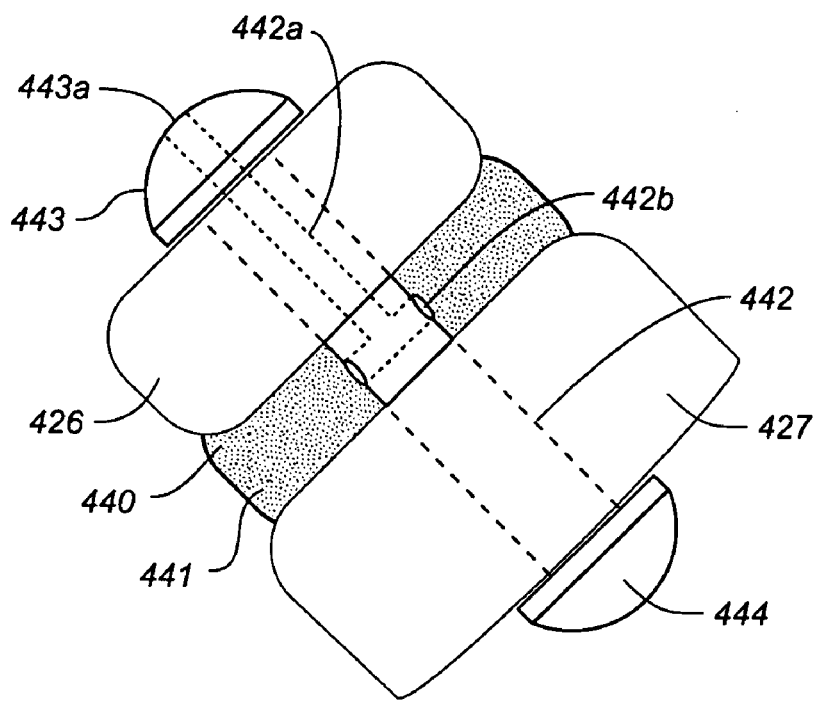
FIG. 38 is a side partial cross section of a facet implant in accordance with the invention.

FIG. 38 illustrates a material 440 such as a polymer injected between the cephalic and caudal facets 426, 427. The material 440 forms a flexible member 441 that allows some movement of the joint due to the flexible properties and/or the shape that permit articulation of the joint. A securing member 442 extends through the facets 426, 427 and the material 440 to further hold the member 441 in place in the joint capsule and/or to prevent implant extrusion. The securing member 442 includes anchors 443, 444 that anchor to the outside or within the facets 426, 427 to hold the securing member 442 in place while permitting some motion for example through spacing at or in the joint. The securing member 442 may for example, comprise a screw, or may be constructed of a flexible material such as a flexible polymer. The securing member may also comprise a band constructed of fibers strands such as Kevlar™, polypropylene or polyethylene, or constructed of a fiber reinforced polymer. The anchors 443, 444 may be of a material such as titanium, or PEAK that may be screwed or crimped on to the securing member 442. The polymer may be injected into the joint capsule into opening 443a in the anchor 443, through a lumen 442a in the securing member 442 and through holes 442b or pores in the securing member 442. This may be done when the joint is distracted or otherwise positioned as desired.

Figure 39:
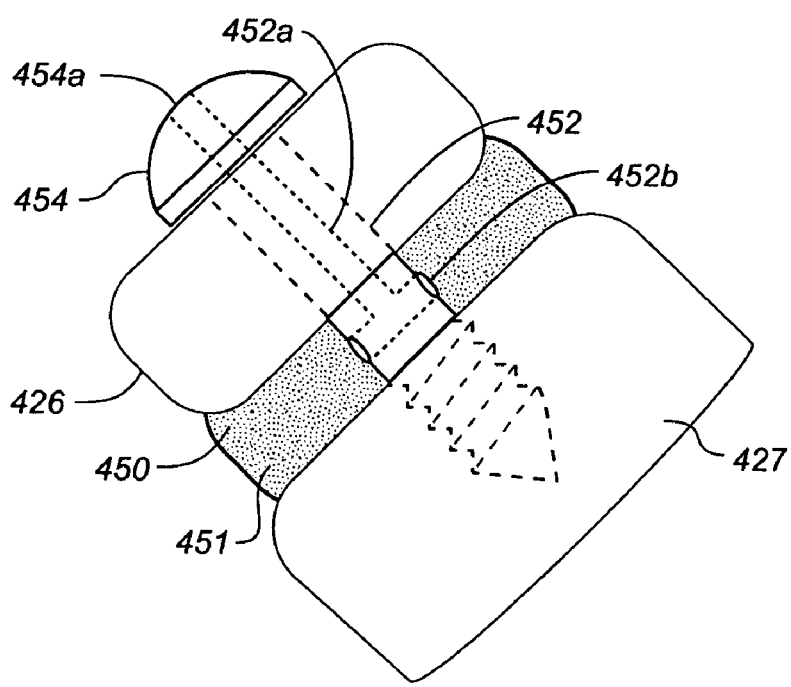
FIG. 39 is a side partial cross section of a facet implant in accordance with the invention.

FIG. 39 illustrates a material 450 such as a polymer injected between the cephalic and caudal facets 426, 427. The material 450 forms an implant 451 that allows some movement of the joint due to the flexible properties and/or a shape that permits articulation of the joint. A securing member 452 extends through the facets 426, 427 and the material 450 to further hold the implant 451 in place in the joint capsule. The securing member 452 includes anchor 453 that anchors the member to the outside or within the facet 426, (or alternatively to the outside or within the facet 427) to hold the securing member 452 in place. The securing member further 452 includes tapered end that allows the securing member 452 to be inserted through the joint capsule and anchored into facet 427. The securing member may be a screw with threaded tip 454 that screws into the bone. The threaded tip may be fixed to the flexible portion 455 that may be constructed in a similar manner as securing member 442 described with reference to FIG. 38. The securing member 452 further includes a flexible portion 455 that allows some movement of the securing member 452 and joint. The anchor 453 may include an opening 453a into a lumen 452a in the securing member 452, for injecting a polymer into a lumen 452a in the member and then through holes 452b into the joint capsule to form the implant 451.

According to the invention, a facet joint device as described herein may be used in combination with an artificial disc or other spinal implants, e.g., to maintain the integrity of the facets. The facet joint distraction or replacement devices and procedures described herein may be used in conjunction with anteriorly placed implants, e.g., in a load sharing arrangement. The facet joint resurfacing, distraction or augmentation as well as the anterior implants may be used with a process to pedicle distraction or stabilizing device as described herein. Various spinal implants may also be used with facet resurfacing, facet distraction or augmentation procedures.

In accordance with one aspect of the invention, narrowing or stenosis of the neural foramen may be treated using a device configured to distract the facet joint. Accordingly, a distraction system is provided for distracting the facet joint.

Figure 23:
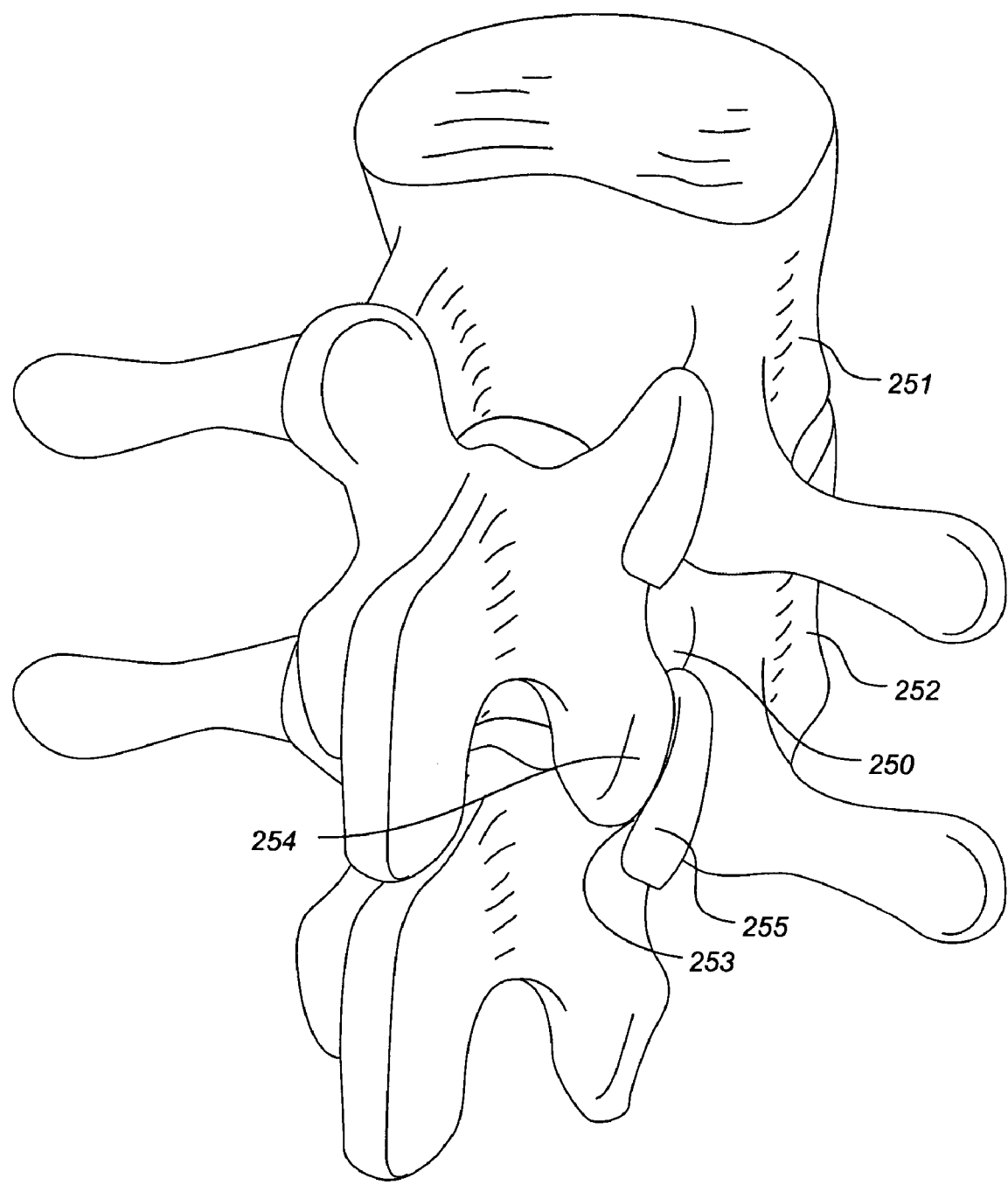
FIG. 23 is a schematic posterior lateral perspective view of a stenotic neural foramen of a posterior spine.

Referring to FIG. 23, a portion of the spine is illustrated with adjoining vertebrae prior to distraction. The neural foramen 250 between a first vertebra 251 and a second vertebra 252 is stenotic. At the zygapophyseal joint capsule 253, there is no gap between the cephalic and caudal facets 254, 255.

Figure 24:
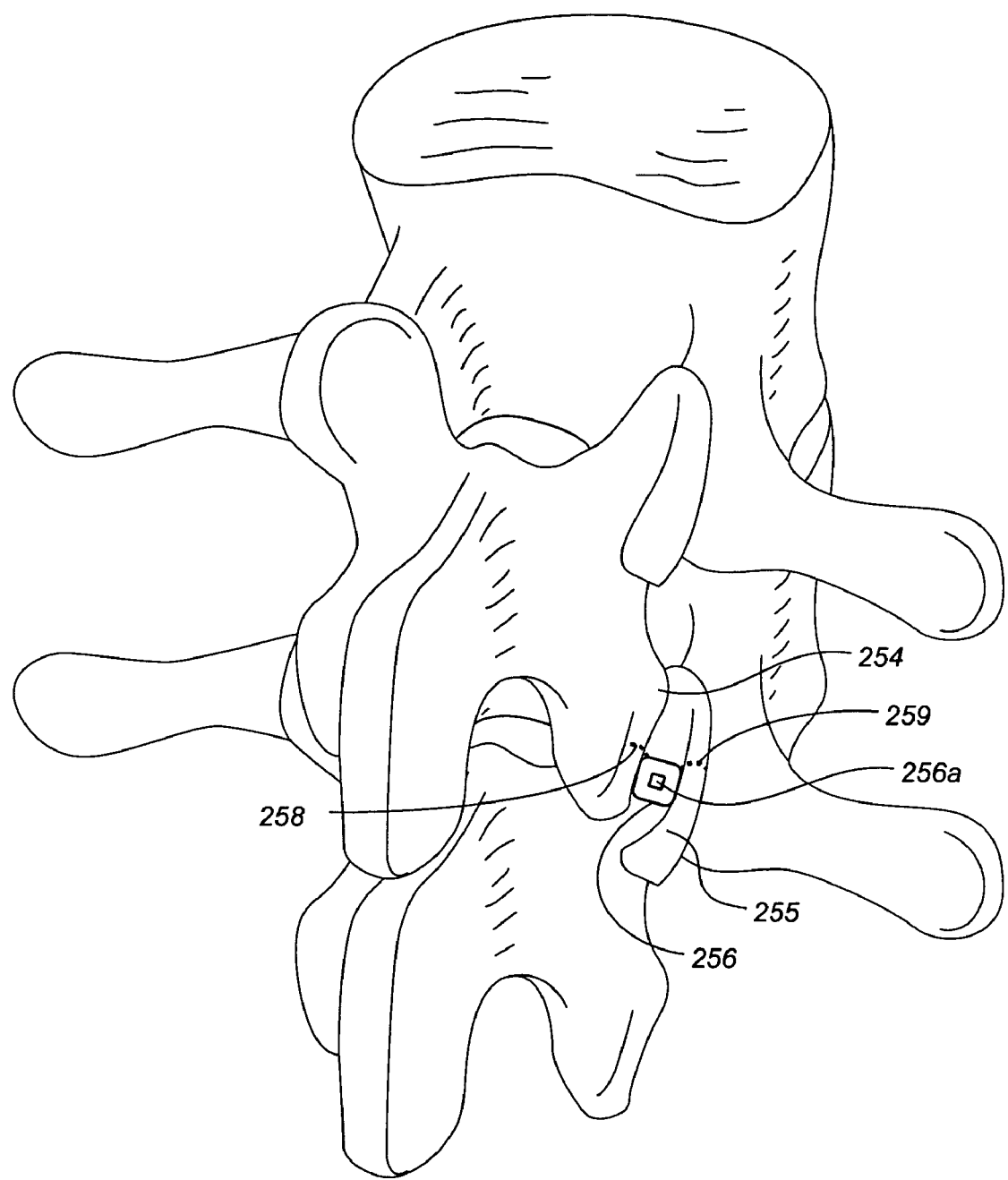
FIG. 24 is a schematic posterior lateral view of a facet implant in accordance with the invention.

Referring to FIG. 24, the portion of the spine of FIG. 23 is illustrated with a facet distracter implant 256 in place between the cephalic facet 254 and the caudal facet 255. The implant 256 comprises a distracting portion 257 and anchors 258, 259 comprising barbs or bone anchors. The distracting portion may include a distracting element as described with respect to FIGS. 16A-16E herein. The anchor 258 is positioned in bone above the cephalic facet 254 while the anchor 259 is positioned in the bone below the caudal facet 255. The facet distracter implant 256 includes a sensor 256a, the type of which may be selected to sense one of a number of different parameters. Pressure sensors, strain gauges, or other sensors may be used to sense load seen by the facet joint. This information may be used to monitor the condition of the facet joint or determine if fusion may be necessary. The other facet joint implants described herein may also include similar sensors.

The procedure for implanting the device generally includes opening the zygapophyseal joint capsule with a scalpel. Then the adjacent vertebrae are distracted by one of a number of known distraction methods or by distracting the joint mechanically using devices such as a wedge or expanding rod or balloon between adjacent spinous processes, or between other parts of adjacent vertebrae. The tissue between the facets 254, 255 is then debrided and/or denervated. The implant is then inserted between the facets 254, 255 after the joint is distracted. The anchors 258, 259 engage the interfacing portions of the bone of the facets 254, 255.

Figure 25:
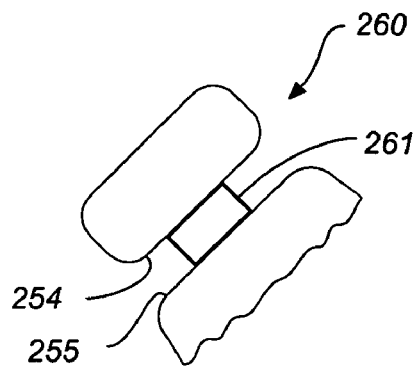
FIG. 25 is a side schematic view of a facet implant in accordance with the invention.
Figure 26:
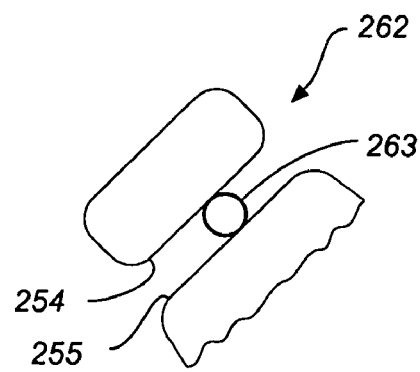
FIG. 26 is a side schematic view of a facet implant in accordance with the invention.
Figure 27:
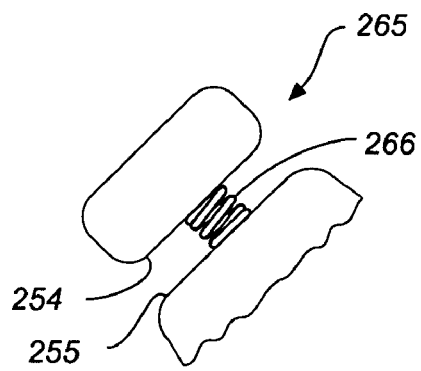
FIG. 27 is a side schematic view of a facet implant in accordance with the invention.
Figure 28:
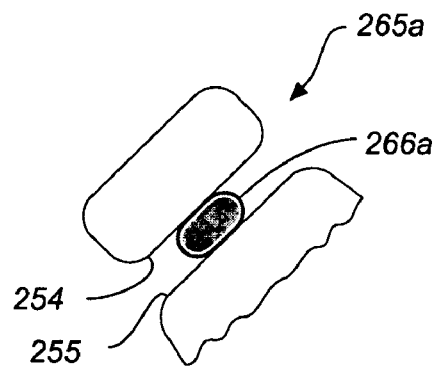
FIG. 28 is a side schematic view of a facet implant in accordance with the invention.
Figure 29:
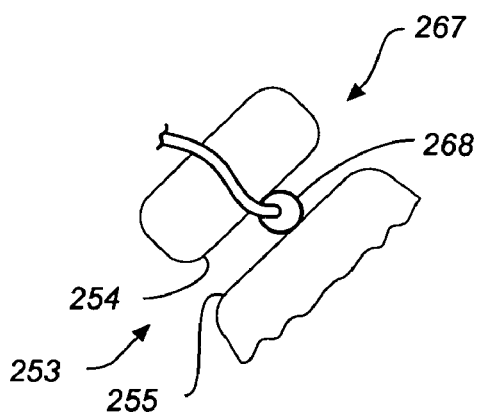
FIG. 29 is a side schematic view of a facet implant in accordance with the invention.
Figure 30:
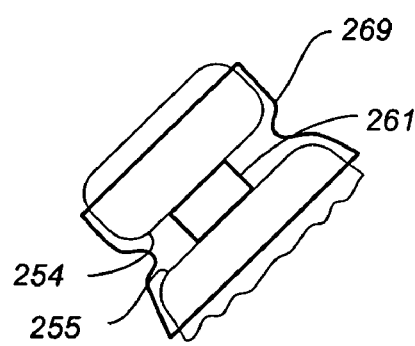
FIG. 30 is a side schematic view of a facet implant in accordance with the invention.

FIG. 25 illustrates a distracter implant 260 positioned between facets 254, 255. The distracter implant 260 comprises a block wedged 261 between the facets 254, 255. In FIG. 26 an alternative distracter 262 implant comprises a ball 263. In FIG. 27 an active distracter implant 265 comprise a coiled spring 266. In FIG. 28, the distracter implant 265a comprises an expandable polymer 266a, e.g., a hydrogel or expandable gel foam. In FIG. 29 the distracter implant 267 comprise an expandable member 268 that may be expanded to distract the joint 253 by inflating with a curable polymer, a liquid, gas or other material. The distraction may occur after implantation to adjust the level of distraction. The expandable member may also be adjusted after implanting by increasing or removing the inflation medium, e.g. using a needle or accessing the member through a one-way valve. FIG. 30 illustrates a shrink-wrap 269 placed partially around the joint 253. The shrink-wrap or other material comprises, e.g., a Dacron material that holds the block 261 or other implant in place between facets 254, 255. The material may encourage ingrowth of tissue. The material may be coated with a material that reduces tissue ingrowth to permit the joint to move or reduces adhesions to prevent pain. The material may include burrs or barbs that secure the material to the bone or it may be secured, e.g. with suture anchors. The implants may be constructed, for example, of a metal, polymer or ceramic, may be coated or imbedded with therapeutic agents (e.g. a steroid or lidocaine) or other material.

Another aspect of the invention is to allow for partial or complete removal of a facet or facet joint in the treatment of spinal stenosis, or for aggressive laminectomy in the treatment of spinal stenosis. A device in accordance with the invention may serve as a shock absorber that allows for partial or complete removal of degenerative facets. Accordingly a device is provided that shares some of the spinal column's axial, torsional, and shear loads, replacing the native painful, deformed, or dysfunctional facet.

In accordance with one aspect of the invention, a distraction system is provided where the system is anchored on opposite sides of a motion segment of a facet joint that would benefit from distraction. On opposite lateral sides of the motion segment, an expandable rod, screw, or other columnar support structure is attached. The length of the support structure may be adjusted to determine the degree or amount of distraction. Additionally, a spring or shock-absorbing element may be included in the distraction device.

Another aspect of the invention is to supplement implants or repair procedures of the anterior column with a posterior shock absorber device (rod, screw, plate). Examples of these implants or procedures include total disc replacements, annular repair, artificial nucleus, and vertebroplasty/kyphoplasty.

Another aspect of the invention is to supplement implants or repair procedures of the posterior column with a shock absorber rod. Examples of these implants or procedures include interspinous distraction wedges, facet joint replacements, and posterior arch replacements.

Another aspect of the invention provides a posterior support implants with shock absorbing properties, to decrease or remove the load experienced by the facets. Implant components may include springs, coils, hydraulic or fluid filled piston chambers, or elastic materials. Each end of the device could be anchored in such a fashion so the rod bridges the facet joint, reducing the loads borne by the joint. This is believed to reduce wear of the facets and resulting pain and altered spinal biomechanics An improved device is provided that utilizes the spinous process, the pedicle, adjacent ribs and/or a transverse process or a combination including one or more of these anatomical structures, to correct or stabilize a deformed spine. The device may be used to correct scoliosis using one or more of these anatomical structures and multiple points at a plurality of spine segments. The correction may be made incrementally over time and may or may not include a fusion process.

In one embodiment, a percutaneously and obliquely placed rigid or dynamic stabilizer is provided. Stabilizer segments are anchored to base of spinous process at one end and a pedicle screw at the other end, as a unilateral temporary stabilizer. The dynamic stabilizers described herein may be adjusted over time to gradually bring the spine in alignment. The stabilizer may be used to derotate (untorque) and correct the spine. A stabilizer placed across a motion segment, i.e., not at the same vertebral level may be used to create overgrowth where desired, i.e. on the non-instrumented side of the motion segment. Such overgrowth may help stabilization or correction of the spine.

FIGS. 44A-46 illustrate an explantable, temporary scoliosis stabilization device. The system is configured to be manipulable once it is installed. The systems illustrated are configured to alter the orientation of a vertebral body and in particular to untorque the spine about the axis of the spinal column as well as applying a corrective straightening or translation force with respect to a vertical rod. According to one aspect of the invention, a device for correcting deformities of the spine is provided where the device may be adjusted over time to direct the corrective forces as needed over time. According to another aspect, a multipoint stabilizing device is coupled to the posterior portions of the spine.

Figure 44A:
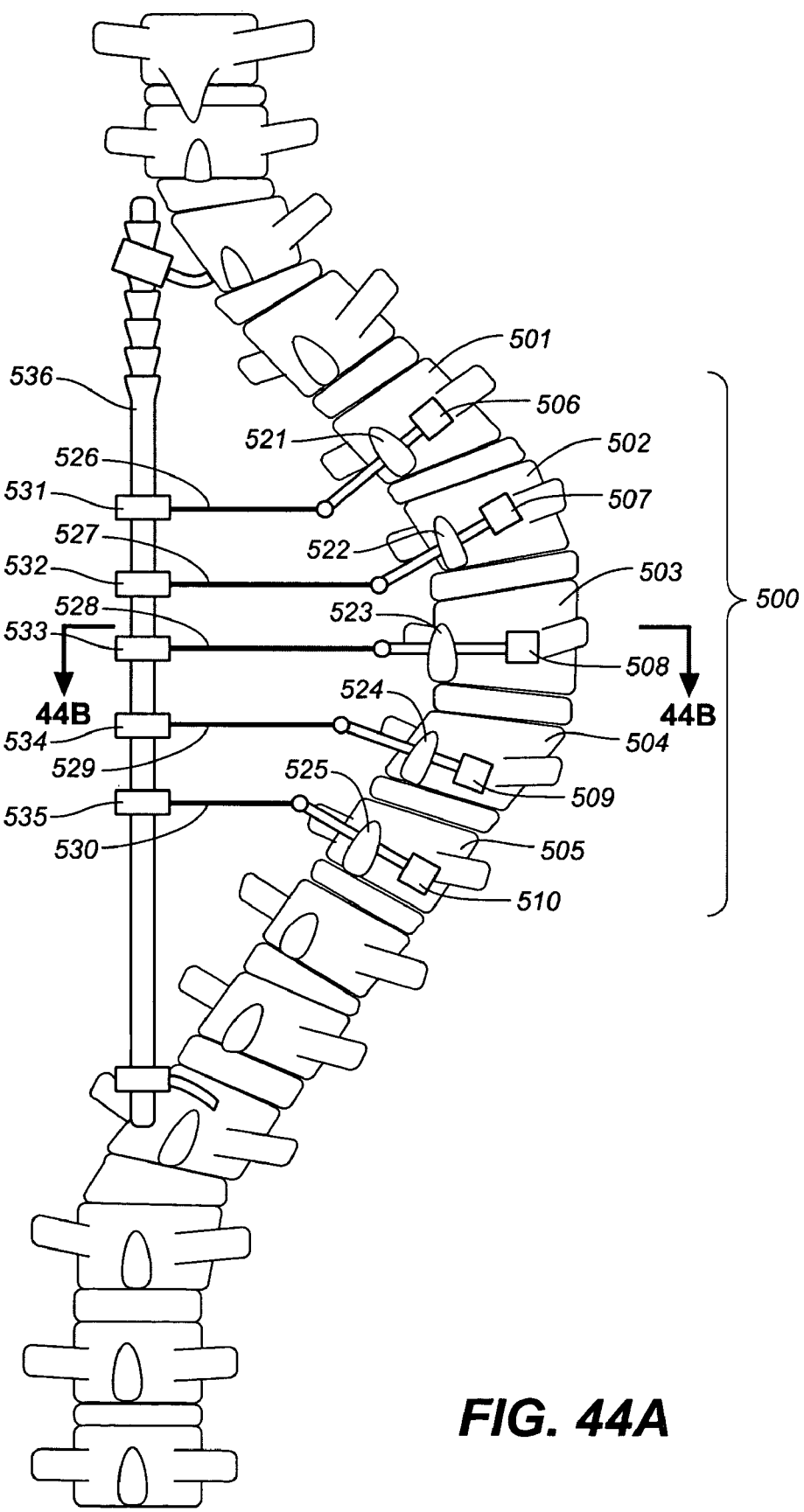
FIG. 44A is a schematic view of a spine deformity correction device in accordance with the invention.
Figure 44B:
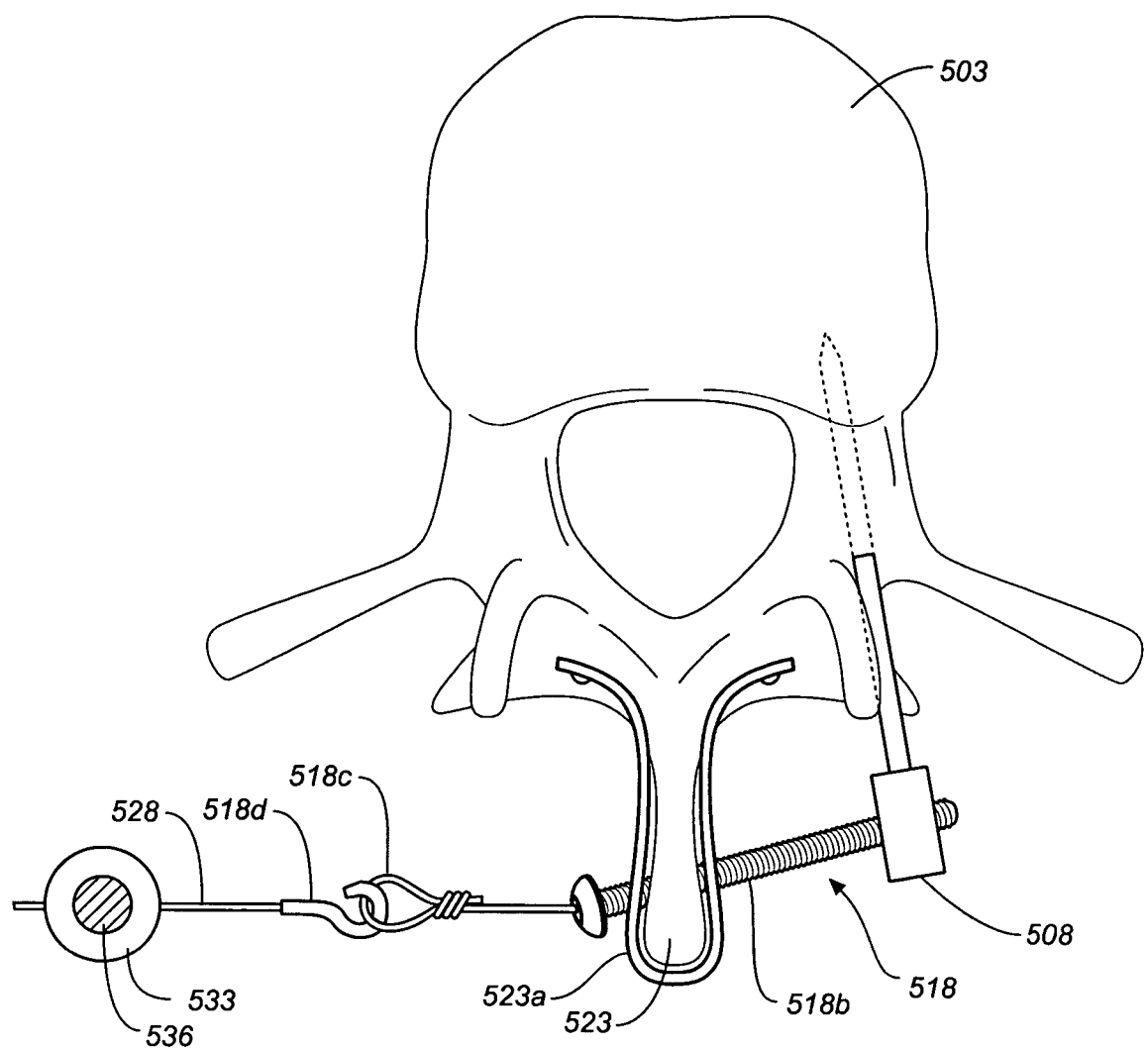
FIG. 44B is a cross section of FIG. 44A along the lines 44B-44B.
Figure 44C:
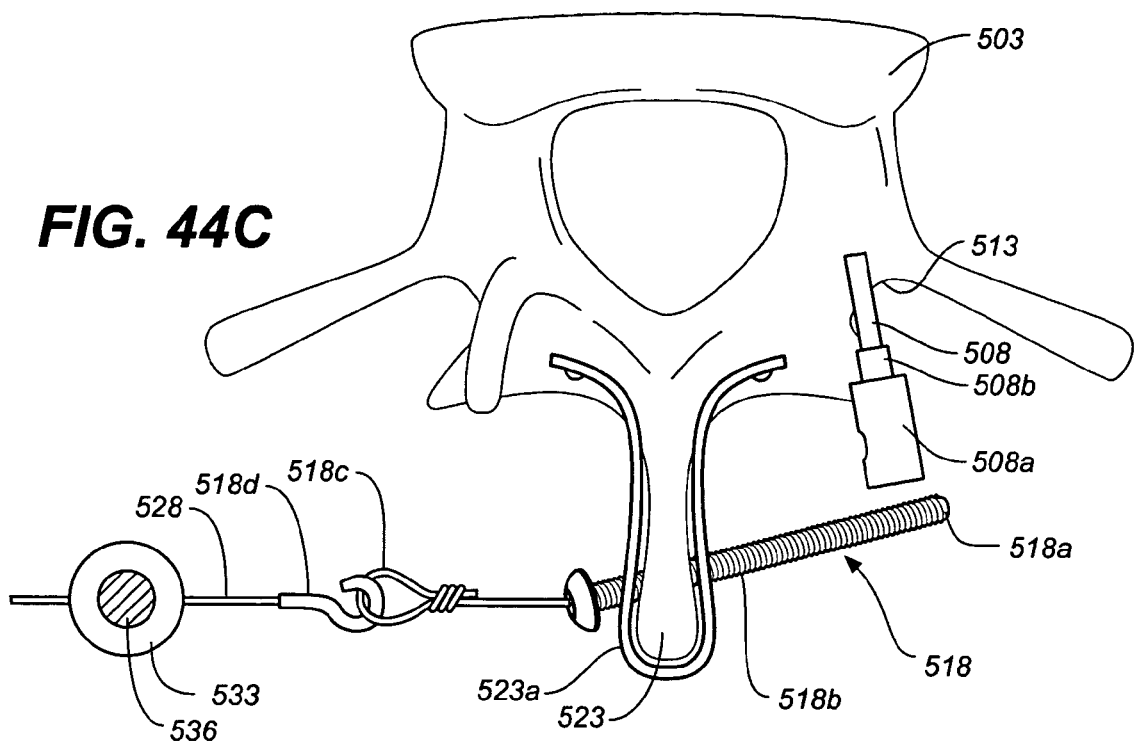
FIG. 44C is a schematic view of an adjustable pedicle attachment device in a first position in accordance with the invention.
Figure 44D:
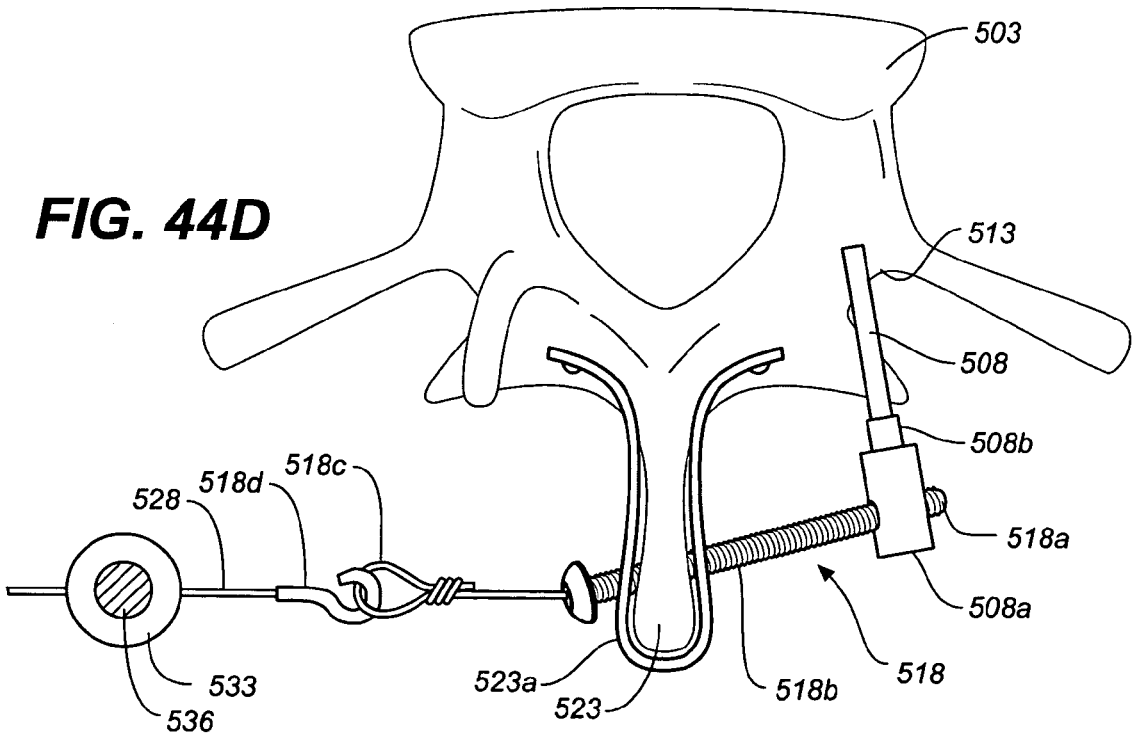
FIG. 44D is a schematic view of the adjustable pedicle attachment device of FIG. 45C in accordance with the invention.
Figure 44E:
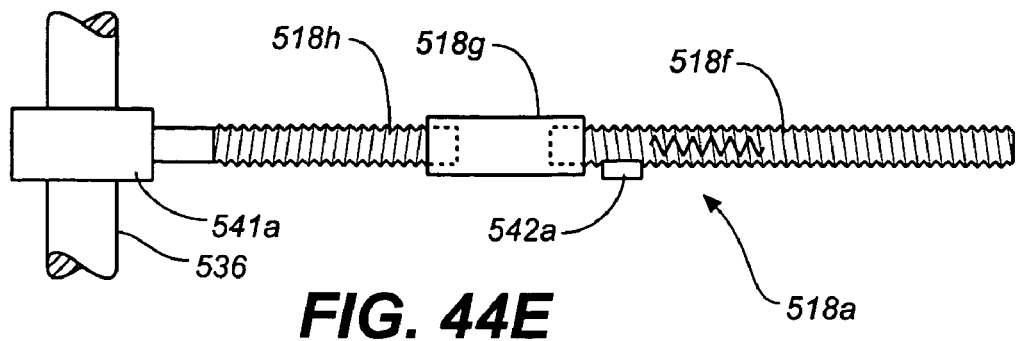
FIG. 44E is a schematic side partial cross sectional view of an alternative connector of the spine deformity device of FIG. 44A.
Figure 44F:
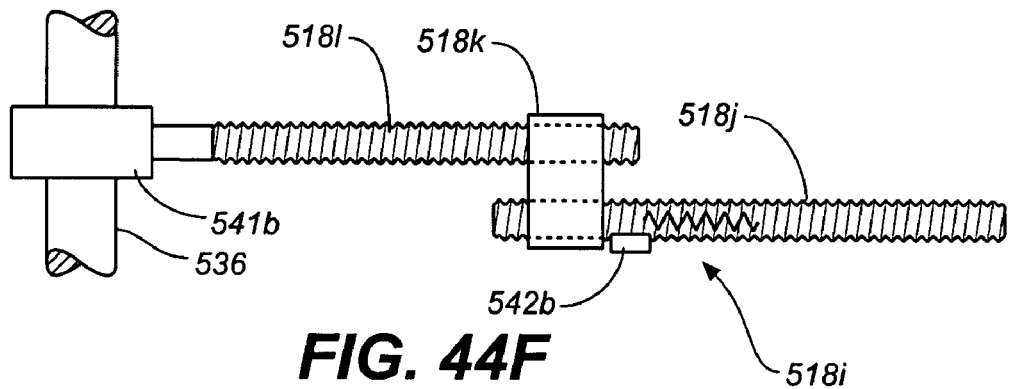
FIG. 44F is a schematic side partial cross-sectional view of an alternative connector of the spine deformity device of FIG. 44A.
Figure 44G:
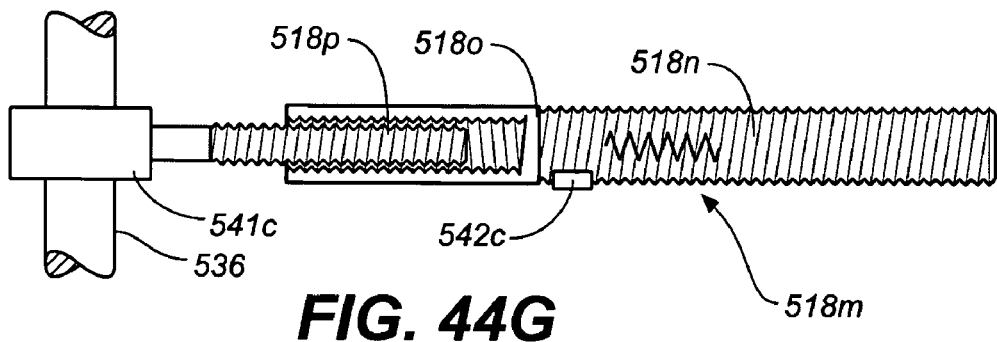
FIG. 44G is a schematic side partial cross sectional view of an alternative connector of the spine deformity device of FIG. 44A.
Figure 44H:
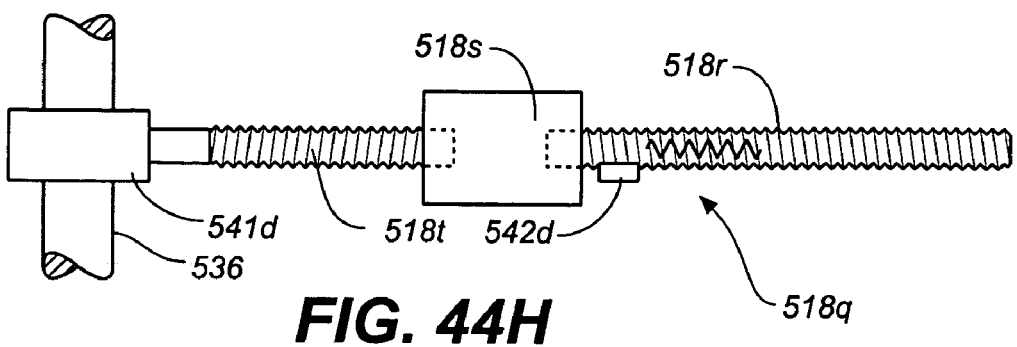
FIG. 44H is a schematic side partial cross sectional view of an alternative connector of the spine deformity device of FIG. 44A.
Figure 45A:
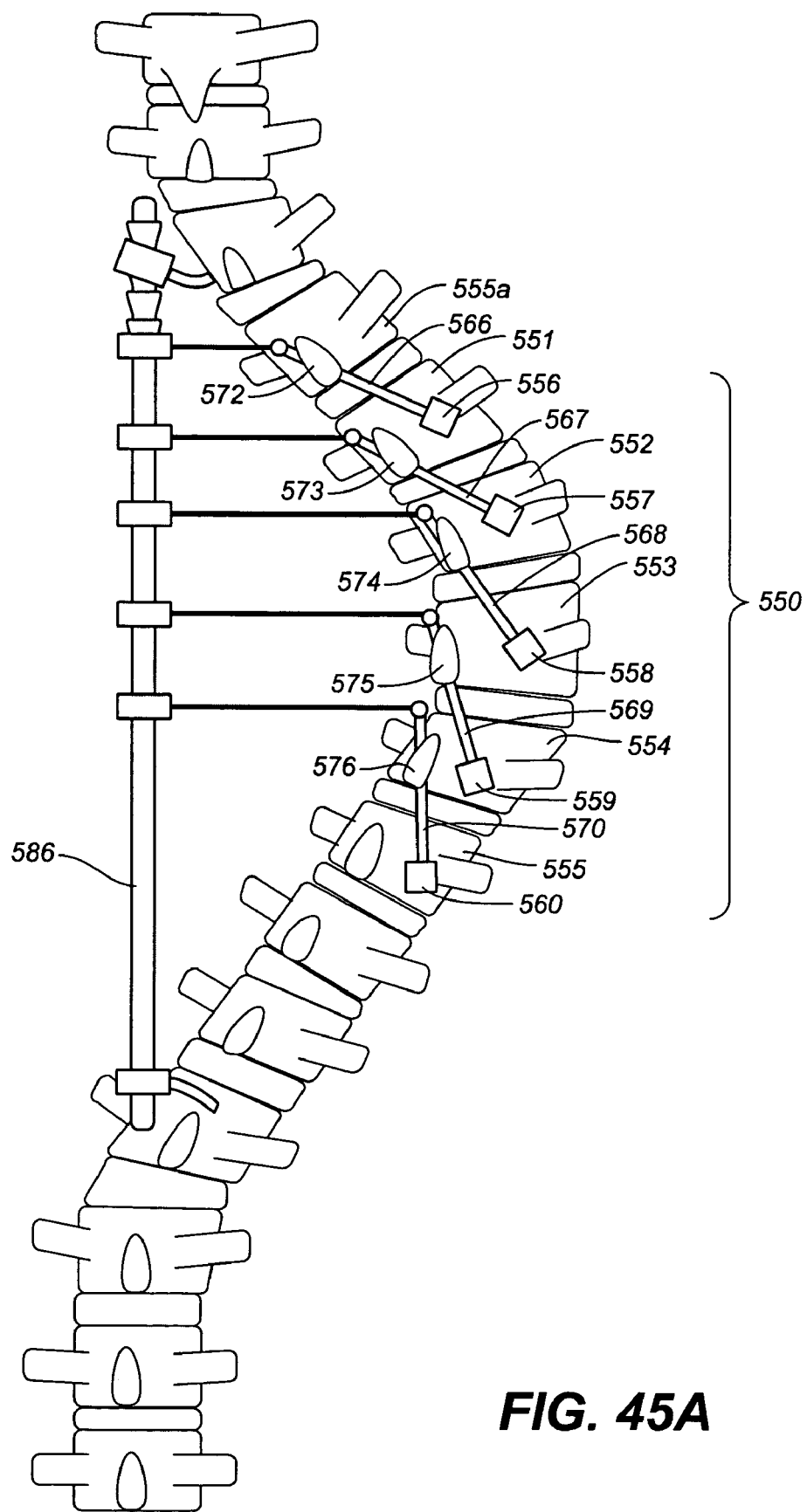
FIG. 45A is a schematic side view of a spine deformity correction device in accordance with the invention.
Figure 45B:
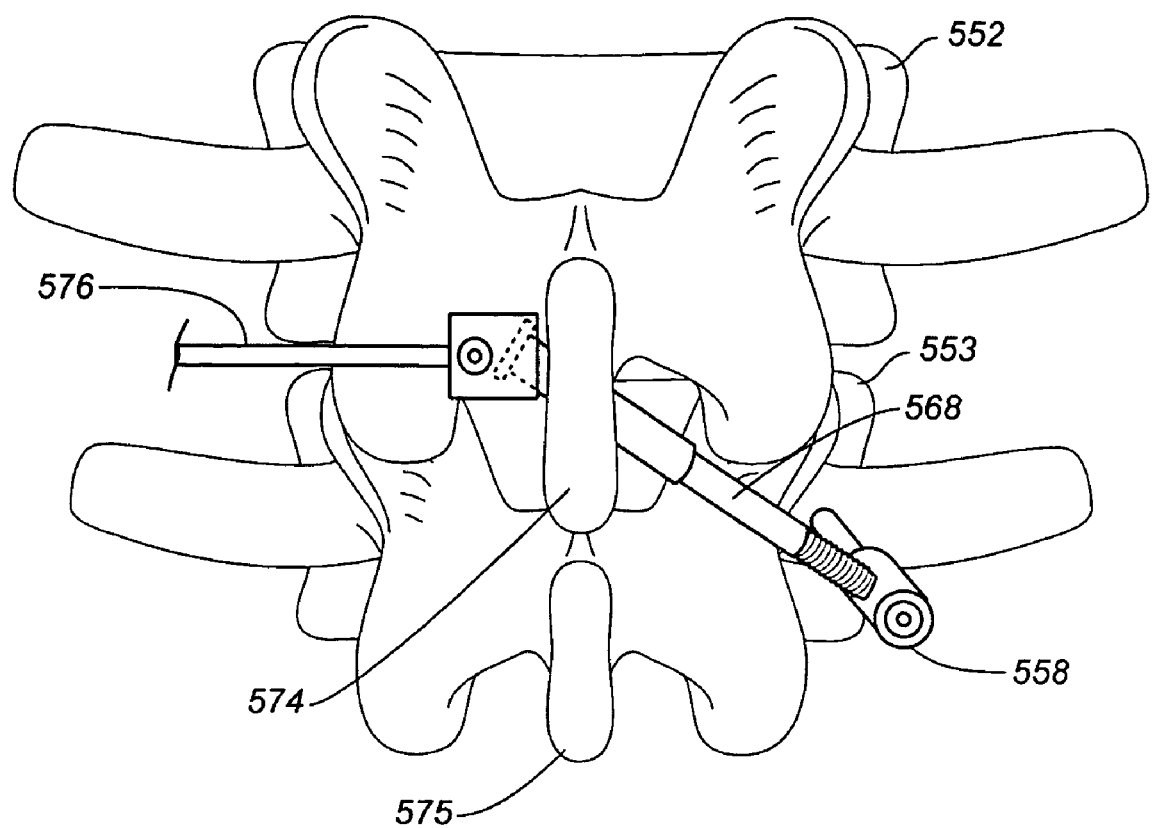
FIG. 45B is a cross section of FIG. 45A along the lines 45B-45B.
Figure 46:
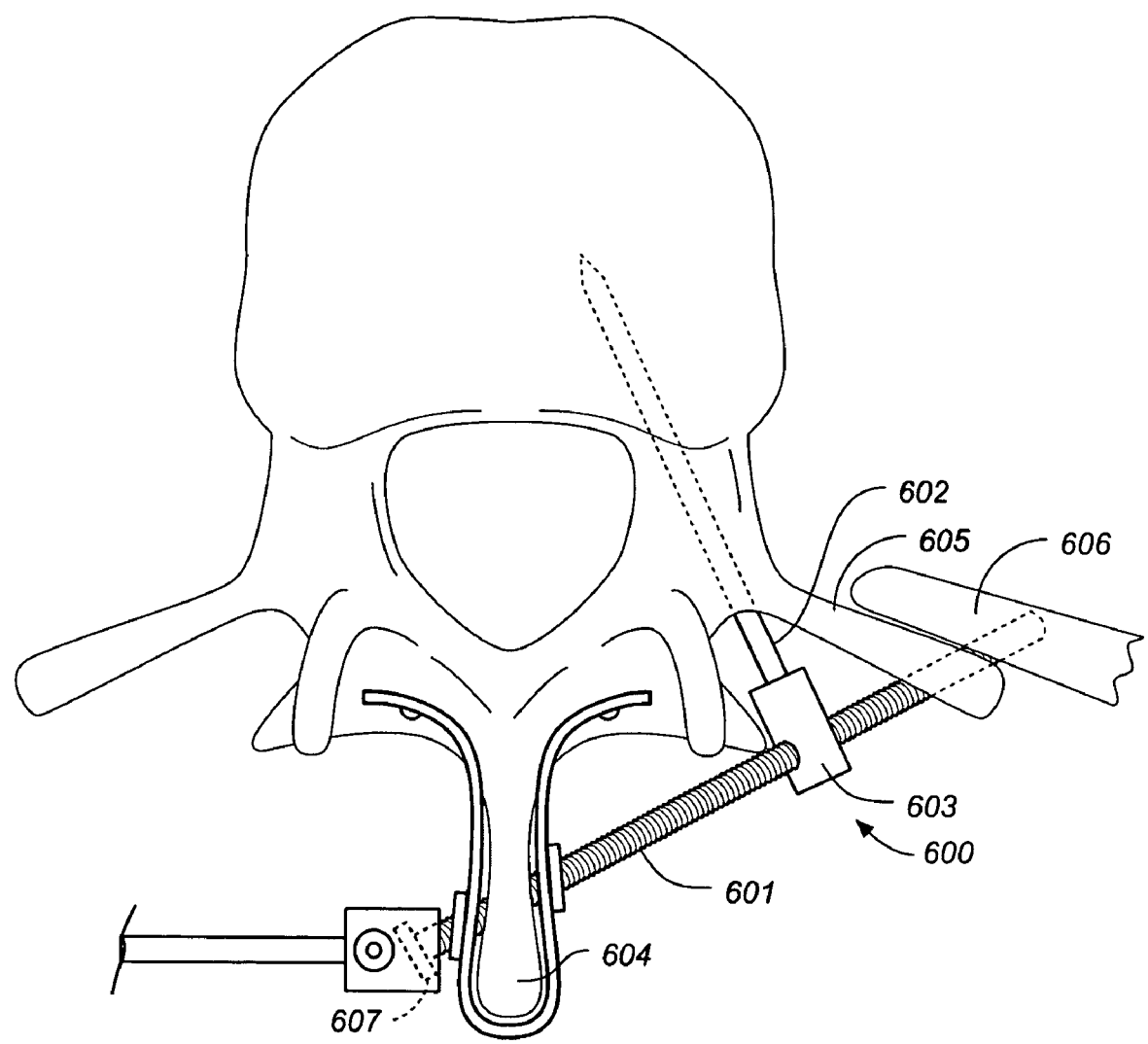
FIG. 46 is a schematic top view of an implant in accordance with the invention.

The systems illustrated in FIGS. 44A-46 comprise a multipoint anchoring mechanism that provides for multidimensional correction of the spinal or spinal segments by positioning the anchor at a plurality of locations on a spine. As illustrated for example in FIGS. 44A-44H, the multiple locations include the spinous process and pedicle of a particular vertebra. A bar is attached between the spinous process and pedicle. A force directing device couples the bar to a vertical rod. As illustrated in FIGS. 45A-45B, the multiple locations include the spinous process of one level and the pedicle of another level (e.g. an adjacent level). As illustrated in FIG. 46, the multiple locations include the spinous process, through a transverse process 605 into a costal aspect of a rib 606. The vertical rod in these figures is attached or coupled to the spine at neutral and balanced vertebra, typically only at the most upper and most lower positions.

The device comprises a telescoping rod (or plate) 536 to which various segments of the spinal column are to be fixed. The rod 536 telescopes to adjust the height to accommodate particular segments or a height of the spine. As illustrated in FIG. 44A a portion 500 of the spine comprises a plurality of adjacent segments 501, 502, 503, 504, 505, (additional adjacent segments may also be corrected). The portion 500 of the spine exhibits a concave curvature between segments 501 and 505. Pedicle screws 506, 507, 508, 509, 510 are attached to pedicles of segments 501, 502, 503, 504, 505, respectively. Dynamic stabilizers 516, 517, 518, 519, 520 are attached to pedicle screws 506, 507, 508, 509, 510 and to spinous processes 521, 522, 523, 524, 525 respectively of segments 501, 502, 503, 504, 505. Wires 526, 527, 528, 529, 530 attached to the rod 536 via hooks 531, 532, 533, 534, 535 attached to the rod 536. The wires 526, 527, 528, 529, 530 are used to tension the portion of the spine 500 to pull on the concavity. If the portion has a convexity, rods may be used in place of wires to push on the convexity to straighten the spine.

FIG. 44B is a cross section of FIG. 44A along the lines 44B-44B. The pedicle screw 508 includes a screw capture device 508a for receiving a screw head or rod of a dynamic stabilizer, in this case, a spinous process screw 518. The capture device may be a hole, a threaded screw hole with a washer or cap. The pedicle screw 508 may be configured to telescope outwards or inwards to be positioned to receive the screw head or rod of a dynamic stabilizer 518 as shown in FIGS. 44C and 44D. The spinous process screw 518 is shown in 44C where, given the trajectory of the spinous process screw 518, its end does not intercept the capture device 508a of the pedicle screw 508. As shown in FIG. 22D the pedicle screw's trunk 508b is lengthened with a telescoping or other similar lengthening mechanism so that the end of the spinous process screw 518 may be positioned in the capture device 508a.

The spinous process screw 518 is anchored through the reinforced spinous process 523 (having a reinforcement hood 523a or is otherwise reinforced as described herein. Note that the reinforcement hood may have a single lamina wing where a single screw is attached as opposed to bilateral screws.) with a head portion 518a engaging the pedicle screw 503 and a rod portion 518b extending through a reinforced spinous process 523. The dynamic stabilizer 518 includes a loop connector end 518c for receiving a hook 518d of a wire (or a telescoping rod) 528 that is attached to the rod 536 with a ratcheted connector 533. The wire may also be a rod, spring, elastic band or other force-directing device. The loop connector end 518c may also be a poly axial connector that allows translation in a variety of directions or places, i.e., so that an oblique angle rod can be captured. (for example, similar to pedicle screw 503 and capture device 503a) The wire 528 may be adjusted or tightened at various times with the ratcheted connector 533, e.g., during a period of time where the spine is being corrected. As the spine is straightened, excess wire may be trimmed off. This procedure may be done percutaneously, e.g. by accessing wire near the skin. Each dynamic stabilizer is similarly constructed.

FIGS. 44E-44H illustrate various dynamic stabilizers that may be used to correct spinal deformity. Dynamic stabilizers 518e, 518i, and 518m are coupled by coupling mechanisms 541a-c to the telescoping rod 536. The coupling mechanisms 541a-c may be positioned on or through the plate or telescoping rod 536. Dynamic stabilizer 518e includes rod 518f that will extend through a reinforced spinous process and is coupled by a coupling mechanism 518g to rod 518h in an end-to-end fashion. Rod 518h slidably extends through opening in coupling mechanism 541a attached to the telescoping rod 536. The rod 518h is adjustable within the coupling mechanism 541a to lengthen or shorten the distance of the dynamic stabilizer 518e between the spinous process and the telescoping rod 536. The coupling mechanism 541a is configured to clamp down on the rod 518h to secure it in place once the distance has been adjusted. The coupling mechanisms 541a-c may include a screw, cam or clamp mechanism to clamp or lockably engage rods 518h, l, and p as described in use herein.

Similarly, dynamic stabilizer 518i includes rod 518j that will extend through a reinforced spinous process and is coupled by a coupling mechanism 518k to rod 518l in an end to side fashion. Rod 518l slidably extends through opening in coupling mechanism 541b attached to the telescoping rod 536. The rod 518l is adjustable within the coupling mechanism 541b to lengthen or shorten the distance of the dynamic stabilizer 518*i* between the spinous process and the telescoping rod 536. The coupling mechanism 541*b* is configured to clamp down on the rod 518*l* to secure it in place once the distance has been adjusted.

Dynamic stabilizer 518*m* includes a rod 518*n* that will extend through a reinforced spinous process and is coupled by a threaded coupling 518*o* to rod 518*p*. The rod 518*p* is slidably and rotatably positioned within a cylindrical hole in coupling mechanism 541*c* attached to the telescoping rod 536. The rod 518*p* may be rotated, i.e., screwed or unscrewed so that the stabilizer lengthens or shortens at the threaded coupling 518*o*. The rotation or screwing may be actuated at or near the skin where the rod 518*p* is positioned in the coupling mechanism 541*c*.

Dynamic stabilizer 518*q* includes a rod 518*r* that will extend through a reinforced spinous process and is coupled by a multiaxial coupling 518*s* similar to a multiaxial screw head type coupling, to rod 518*t*. The rod 518*t* is a telescoping rod and is coupled by coupling mechani8sm 541*d* to the vertical rod 536.

Each of the dynamic stabilizers may include sensors located thereon to sense data corresponding to a parameter of the dynamic stabilization device or the spine. FIG. 44E-44H illustrate sensors 542*a*-542*d* located on the dynamic stabilizer. The sensors may comprise, e.g., a strain, stress, pressure, position or motion sensor. Such sensors may include a variety of sensors that are generally know. For example, strain gauges, accelerometers or piezo electric sensors may be employed to sense parameters that correspond, e.g., to the position of the spine, a vertebra, a dynamic stabilizer, as well as the parameters relating to the forces or mechanical loads that are effecting the device. Each of the sensors may individually sense information or information relative to each of the other sensors may be sensed and compared. The information may be used to set tension on the device, to identify when repositioning is necessary or to otherwise provide information as to the status of the device or portions thereof, or status of the spine that is being treated. The sensors may include some level or circuitry including, e.g. a telemetry circuit that transmits information concerning the sensors to an external device. The sensors may be battery powered or may use passive circuits that are powered by an external device. The information may be used to identify when one of the stabilizers no longer has tension associated with the stabilizer thus identifying when the tension needs to be modified in the device. Accordingly, each segment may be moved separately, monitored separately and adjusted separately form the other segments. Each segment may be moved to a different degree and in different directions or at different angles with varying forces.

FIG. 45A illustrates an alternative configuration of the correction device according to the invention. A portion 550 of the spine comprises a plurality of adjacent segments 551, 552, 553, 554, 555, 555*a* (additional adjacent segments may also be corrected). The portion 550 of the spine exhibits a concave curvature between segments 551 and 555*a*. Pedicle screws 556, 557, 558, 559, 560 are attached to pedicles of segments 551, 552, 553, 554, 555, respectively. Dynamic stabilizers 566, 567, 568, 569, 570 are attached to pedicle screws 556, 557, 558, 559, 560 and through spinous processes, 572, 573, 574, 575, 576 respectively of adjacent segments 555*a*, 551, 552, 553, 554. Thus, the dynamic stabilizers are positioned across the motion segments between the corresponding adjacent segments. The dynamic stabilizers 566, 567, 568, 569, 570 attached to the telescoping rod 576 in one or more manners such as, for example, the dynamic stabilizers 518, 518*e*, 518*i*, 518*m*, 518*q* as illustrated in FIGS. 44A-44H, herein.

The dynamic stabilizers 566, 567, 568, 569, 570 are used to tension the portion of the spine 500 to pull on the concavity, or if the portion has a convexity, to push , pull on, or translate the convexity to straighten the spine. Thus each of the dynamic stabilizers are attached a plurality of locations on the spine and operate to stabilize adjacent segments with respect to each other.

FIG. 45B illustrates a pedicle screw and dynamic stabilizer in greater detail. The pedicle screw 558 is screwed into pedicle 563 of vertebra 553. The pedicle screw 558 includes a screw hole 558*a* for receiving a screw head or rod of a dynamic stabilizer 568. A screw capture device 568*b* such as a nut or a threaded portion of the pedicle screw is configured to capture and receive the dynamic stabilizer screw or rod portion 568*a*. The capture device 568*b* of the stabilizer engages the pedicle screw 558 and a rod portion 568*b* extends through a reinforced spinous process 574. The dynamic stabilizer 568 includes a connector end 580 for receiving a wire 578 or a hook of a telescoping rod that is attached to the telescoping rod 576. The dynamic stabilizer 568 is anchored through the reinforced spinous process 574 of an adjacent vertebra 554 (FIG. 17A) thus immobilizing or stabilizing the motion segment between the vertebra 553, 554. This device may also be used in fusion, i.e. to fuse the motion segments across vertebra of a multipoint connector. The device may also be used to encourage overgrowth at certain locations. In particular it may encourage overgrowth on the non-fused lateral side of a vertebra (opposing the fused lateral side) stabilized with the multipoint connector between two vertebrae.

FIG. 46 illustrates a device for treating a deformity such as scoliosis. The device includes a dynamic stabilizer 600 comprising a spinous process screw 601 and a pedicle screw 602 including a spinous process screw capture device 603. The spinous process screw is configured to be positioned through a reinforced spinous process 604 and through a transverse process 605 into a costal aspect of a rib 606. The dynamic stabilizer 600 includes a connector portion 607 configured to be connected to a telescoping rod as described herein with reference to FIGS. 44A-H and 45A-45B. Similar to FIGS. 44A-H and 45A-45B, a plurality of segments may be secured to a telescoping rod with a plurality of dynamic stabilizers. The pedicle screw in this and all other embodiments described in this application may include a telescoping portion that can adjust the length of the screw head from the anchoring point where the pedicle screw is anchored into the bone. The pedicle screw 602 also includes a sensor 608 located thereon (or incorporated therewith). The sensor may comprise, for example, a motion detector, a position detector, a pressure sensor, a strain gauge, and ultrasonic transducer/ sensor. The sensor may sense a change in strain on the screw that may be due to loosening or repositioning of the screw. The sensor may also sense a change in position of the screw that indicates a change in alignment and corresponding loosening or repositioning of the screw. The sensor may also sense a change in pressure due to loosening or repositioning of the screw. The sensor may also include an ultrasonic transducer and transmitter that can determine change in positioning of the screw, e.g. loosening of the screw indicated by a change in interfaces of materials or characteristic property change indicating screw loosening or repositioning. The sensor may include some electronics such as a telemetry circuit that allows it to communicate with an external device. The sensor may also be powered by an external device e.g., in a manner generally known in the art.

The various embodiments of the invention described herein may include sensors integrated with or provided on a structural spinal implant. A number of factors may be detected as described herein. Additional factors may include, e.g., local inflammation, pressure, tension, edema, motion, water content, and electrolytes or other chemicals. The sensors allow a doctor to monitor patients for response to healing, or may be used by the doctor to guide serial adjustments to the patient's treatment. For example, measurements from the sensing means could lead the doctor to change the length or tension of a distraction rod or stabilization device. Patients could adjust therapy based on measurements from the sensing device, or could be alerted to notify their doctor should certain measurements be of concern. The sensor is configured to be adjustable to sensed stresses. The sensor may for example, be a strain gauge, a pressure sensor accelerometer, position sensor, imaging device, etc. The sensor may be used in the initial adjustment of the prosthesis or may be monitored over time. The sensor may sense shear/torsion tension/compression. Sensors may sense stresses at various motion segments. The sensor may be used to compare stresses at various motion segments or locations. Various sensors may be selected from sensors that are known to one of skill in the art or that are commercially available.

Anchoring of Therapeutic Devices

Some patients obtain back pain relief with injections of steroids and anesthetic agents at the site of pain; however the relief is temporary requiring that patients return for repeat injections when their pain recurs.

One embodiment of the invention comprises an anchor device with a therapeutic substance or drug delivery device, e.g. a drug port and/or reservoir, or matrix attached to a vertebra. In one embodiment, the device is anchored adjacent a site near where pain is present. The port is configured to deliver steroids or anesthetic agents via a catheter to a desired location, for example, the facet joint, neural foramen, vertebral body, annulus, nucleus, back muscles, back ligaments, bone metastases, intrathecal space, epidural space, or other targets in, on, or around the spine. The catheter can direct the drug to the correct location by positioning the end of the catheter at a target location. The port is configured to be refilled periodically percutaneously, e.g. using an imaging device and a percutaneously placed needle that can inject the refill into the port, e.g. through a biocompatible polymer or rubber type port access mechanism. The device further comprises a patient actuation mechanism for patient control of drug delivery as needed for pain relief, manually or remotely using a telemetrically triggered delivery from an external telemetry control device. According one aspect of the invention such a device is attached to a boney structure of the spine. Other device that may be attached to the spine may include sensory or therapeutic devices, including nerve stimulators, bone growth stimulators and radioactive seeds.

In addition, a structural implant could be anchored to bone, to which a sensory or therapeutic device could be attached. The sensory or therapeutic device could be placed external to the bone, on the surface of the bone, or internal to the bone.

Figure 47:
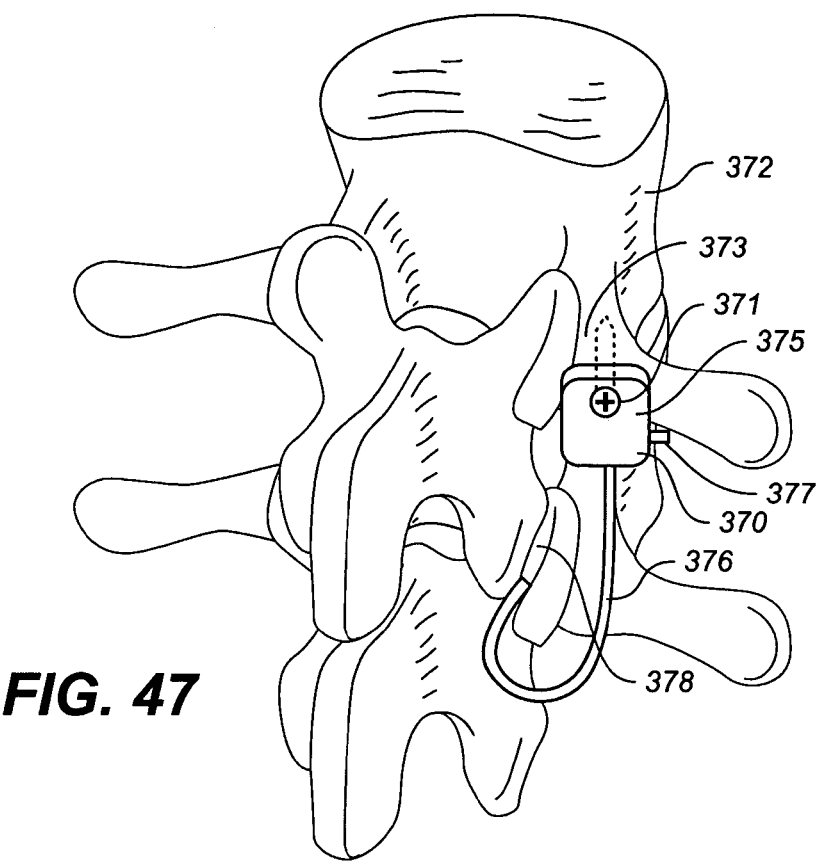
FIG. 47 is a schematic posterior lateral perspective view of a therapeutic substance delivery device in accordance with the invention.
Figure 48:
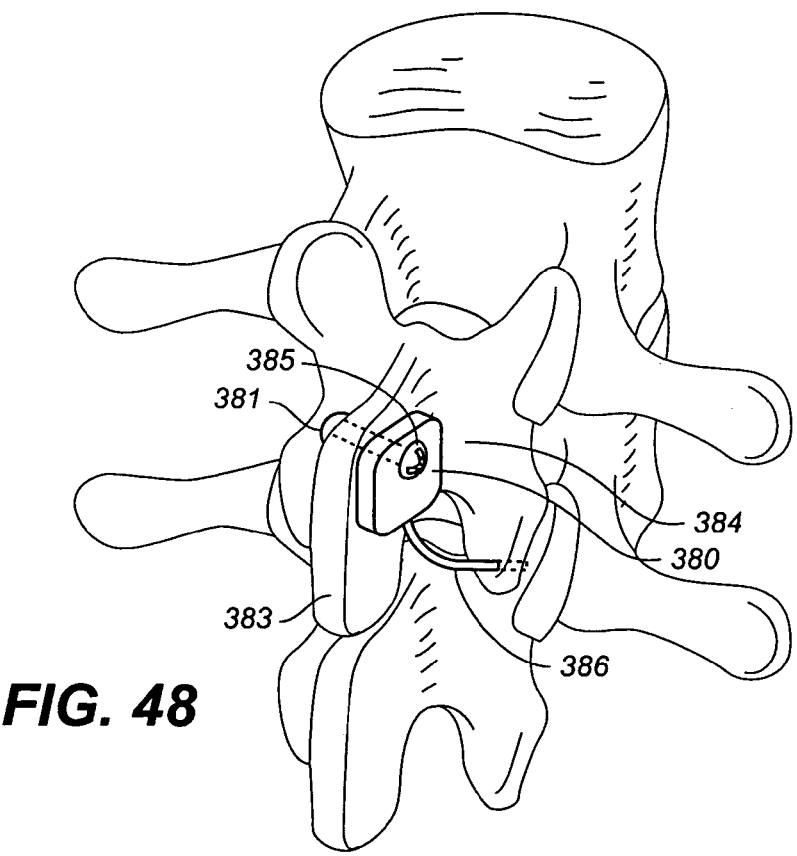
FIG. 48 is a schematic posterior lateral perspective view of a therapeutic substance delivery device in accordance with the invention.

FIGS. 47 and 48 illustrate drug delivery devices 370, 380, respectively, in accordance with the invention. The drug delivery device 370 includes a reservoir 375 attached by an anchor 371 configured to anchor the reservoir 375 to the bone of the spine. In particular, in this embodiment, the anchor 371 comprises a pedicle screw that anchors the device to the pedicle 373 of a vertebra 372. The reservoir 375 includes a catheter 376 in communication with the contents of the reservoir 375 and having an end positioned adjacent or in a zygapophyseal joint 378 where the drug is directed to have a therapeutic effect on the joint 378. The device may include a telemetrically actuable pump mechanism for delivering the drug to the joint upon telemetric actuation by an external control device. The device 370 further comprises a port 377 for receiving (e.g. via a percutaneously introduced needle) into the reservoir 375, refills of the therapeutic substance or drug. Device 380 comprises a similar catheter 386, and reservoir 385 attached by an anchor 381 to the spinous process 383 or alternatively an adjacent lamina 384. The spinous process 383 or lamina 384 may be reinforced prior to attachment of the anchor 381 or may be attached to a reinforcement device positioned at the posterior arch of the spine, as described herein with reference to FIGS. 1A-7B.

The invention claimed is:

1. A spine implant system comprising:
a spinous process reinforcement system extending generally along a first plane, the first plane adapted to be generally coplanar with a median plane of a first vertebra, the spinous process reinforcement system being configured to provide structural reinforcement to a spinous process of the first vertebra; and
a force exertion device coupled to the spinous process reinforcement system and extending generally along a longitudinal axis from the spinous process reinforcement system, the longitudinal axis intersecting the first plane at an oblique angle, the force exertion device having a connecting portion sufficiently spaced apart from the spinous process reinforcement system to allow the connecting portion to connect to a second vertebra at a location lateral to the first plane, the force exertion device being configured to exert a force between the spinous process and the second vertebra, the spinous process reinforcement system being configured to distribute the force applied by the force exertion device onto the spinous process of the first vertebra, the force exertion device comprising a first engaging surface and the spinous process reinforcement system comprising a second engaging surface wherein when deployed, the first engaging surface engages the second engaging surface to thereby indirectly engage the force exertion device with the spinous process.

2. The spine implant system of claim 1 wherein the force exertion device comprises an elongate member.

3. The spine implant system of claim 1 wherein the force exertion device further comprises a dynamic element configured to permit limited relative movement of the first and second vertebrae.

4. The spine implant system of claim 1 wherein the spinous process reinforcement system comprises a reinforcement structure inserted into cancellous bone of the spinous process.

5. The spine implant system of claim 4 wherein the reinforcement structure comprises a curable polymer.

6. The spine implant system of claim 4 wherein the reinforcement structure comprises a member having a first unexpanded position and a second expanded position wherein the reinforcement structure is configured to be inserted into a cavity in the bone in the first position and is configured to expand into the second expanded position when implanted in the cavity.

7. The spine implant system of claim 4 wherein the reinforcement structure comprises at least one strut.

8. The spine implant system of claim 1 wherein the reinforcement system comprises an external hood configured to be positioned over a portion of the spinous process.

9. The spine implant system of claim 8 wherein the hood comprises a malleable material configured to be shaped about the portion of the spinous process.

10. The spine implant system of claim 8 wherein the hood further comprises wings configured to be positioned adjacent lamina of the vertebra.

11. The spine implant system of claim 8 wherein the hood further comprises at least one opening configured to accurately locate a position of the force exertion device.

12. The spine implant system of claim 1 wherein the force exertion device is configured to exert a distracting force between the spinous process and the second vertebra.

13. The spine implant system of claim 1 wherein the force exertion device is configured to exert a compressive force between the spinous process and the second vertebra.

14. The spine implant system of claim 1 wherein the force exertion device is configured to exert a derotating force between the spinous process and the second vertebra.

15. The spine implant system of claim 12 wherein the force exertion device is further configured to exert a derotating force between the first vertebra and the second vertebra.

16. The spine implant system of claim 1 wherein the force exertion device is configured to fail upon application of a predetermined force.

17. A spine distractor system comprising:
an implantable distraction device configured to exert a distraction force across at least one joint between vertebrae of the spine, the distraction device comprising:
  a first portion configured to couple the distraction device to a location on a spinous process of a first vertebra of a spine;
  a second portion configured to be coupled to a bony portion of a second vertebra; and
  an elongate structure having a first end and a second end, the elongate structure attached at the first end to the first portion and adapted to extend across the at least one joint between the first portion and the second portion;
the first portion comprising a spinous process reinforcement system configured to provide structural reinforcement to the spinous process to support the distraction device, the reinforcement system comprising a plate and being attachable to the vertebra that the plate can contact at least one side of a spinous process of the vertebra, whereby a force applied to the first portion by the elongate structure is distributed by the plate across at least a portion of the spinous process, wherein the distraction device comprises a spring member.

18. The spine distractor of claim 17 wherein a median plane intersects the first vertebra, and a horizontal plan intersects the first vertebra, and wherein the elongate portion is configured to extend across the median plane at an oblique angle with respect to the median plane and across the horizontal plane at an oblique angle with respect to the horizontal plane.

19. The spine distractor of claim 17 wherein a median plane intersects the first vertebra, and wherein the elongate portion is configured to extend across the median plane at an oblique angle with respect to the median plane.

20. The spine distractor system of claim 17 wherein the first portion comprises a first engaging surface and wherein the spinous process reinforcement system comprises a second engaging surface wherein when deployed, the first engaging surface engages the second engaging surface to thereby indirectly engage the distraction device with the spinous process.

21. The spine distractor system of claim 17 wherein the spinous process reinforcement system comprises a reinforcement structure inserted into cancellous bone of the spinous process.

22. The spine distractor system of claim 21 wherein the reinforcement structure comprises a curable polymer.

23. The spine distractor system of claim 21 wherein the reinforcement structure comprises at least one strut.

24. The spine distractor system of claim 17 wherein the reinforcement system comprises an external hood configured to be positioned over a portion of the spinous process.

25. The spine implant of claim 24 wherein the hood further comprises at least one opening configured to accurately locate a position of the spine implant device.

26. The spine distractor system of claim 24 wherein the hood comprises a malleable material configured to be shaped about the portion of the spinous process.

27. The spine distractor system of claim 24 wherein the hood further comprises wings configured to be positioned adjacent lamina of the vertebra.

28. The spine distractor system of claim 17 wherein the distraction device comprises a dynamic element configured to permit limited movement across the joint.

29. A spine implant system comprising:
a spinous process reinforcement system extending generally along a first plane, the first plane adapted to be generally coplanar with a median plane of a first vertebra, the spinous process reinforcement system being configured to provide structural reinforcement to a spinous process of the first vertebra; and
a force exertion device coupled to the spinous process reinforcement system and extending generally along a longitudinal axis from the spinous process reinforcement system, the longitudinal axis intersecting the first plane at an oblique angle, the force exertion device having a connecting portion sufficiently spaced apart from the spinous process reinforcement system to allow the connecting portion to connect to a second vertebra at a location lateral to the first plane, the force exertion device being configured to exert a force between the spinous process and the second vertebra, the spinous process reinforcement system being configured to distribute the force applied by the force exertion device onto the spinous process of the first vertebra, wherein the force exertion device has a length which is adjustable after implantation, and wherein the force exertion device comprises a remotely actuatable length adjusting member.

* * * * *

UNITED STATES PATENT AND TRADEMARK OFFICE
Certificate

Patent No. 7,611,526 B2                                        Patented: November 3, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Allen L. Carl, Slingerlands, NY (US); Dan Sachs, Minneapolis, MN (US); and Meir Rosenberg, Newton, MA (US).

Signed and sealed this Eighth Day of June 2010.

EDUARDO C. ROBERT
*Supervisory Patent Examiner*
Art Unit 3733

UNITED STATES PATENT AND TRADEMARK OFFICE
CERTIFICATE OF CORRECTION

PATENT NO. : 7,611,526 B2 Page 1 of 2
APPLICATION NO. : 11/197573
DATED : November 3, 2009
INVENTOR(S) : Allen L. Carl et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 620 days.

should read (*) Notice: Subject to any disclaimer, the term of this patent is extended or adjusted under 35 U.S.C. 154(b) by 1,005 days.

In Column 1, Line 28, please delete "boney" and insert --bony--, therefor.

In Column 2, Line 9, after "foramen", please insert --.--.

In Column 3, Line 66, please delete "and or" and insert --and/or--, therefor.

In Column 4, Line 31, please delete "boney" and insert --bony--, therefor.

In Column 4, Line 53, please delete "and or" and insert --and/or--, therefor.

In Column 6, Line 63, after "invention", please insert --.--.

In Column 8, Line 52, please delete "45C" and insert --44C--.

In Column 9, Line 42, please delete "and or" and insert --and/or--.

In Column 10, Line 67, after "120", please insert --.--.

In Column 11, Line 25, please delete "pedical" and insert --pedicle--, therefor.

In Column 14, Line 66, please delete "may provided" and insert --may be provided--, therefor.

In Column 16, Line 5, after "locking", please delete "features".

In Column 16, Line 59, please delete "features features." and insert --features.--, therefor.

In Column 17, Line 43, before "piezo-", please delete "a".

Signed and Sealed this

Fourteenth Day of September, 2010

David J. Kappos
*Director of the United States Patent and Trademark Office*

CERTIFICATE OF CORRECTION (continued)
U.S. Pat. No. 7,611,526 B2

In Column 18, Line 32, please delete "force." and insert --force--, therefor.

In Column 21, Line 41, please delete "Sexant" and insert --Sextant--, therefor.

In Column 21, Line 66, please delete "may replaced" and insert --may be placed--, therefor.

In Column 24, Line 9, please delete "zygapopyhseal" and insert --zygapophyseal--, therefor.

In Column 24, Line 15 (approx.), please delete "zygapopyhseal" and insert --zygapophyseal--, therefor.

In Column 27, Line 3, after "biomechanics", please insert --.--.

In Column 28, Line 34, after "captured", please delete ".".

In Column 28, Line 35, after "503a)", please insert --.--.

In Column 29, Line 19, please delete "mechani8sm" and insert --mechanism--, therefor.

In Column 29, Line 27, please delete "know" and insert --known--, therefor.

In Column 31, Line 49, please delete "boney" and insert --bony--, therefor.